(12) United States Patent
Friedman et al.

(10) Patent No.: US 8,404,639 B2
(45) Date of Patent: Mar. 26, 2013

(54) METHODS AND KITS FOR TREATING DISEASE BY ADMINISTERING INSULIN-LIKE GROWTH FACTOR BINDING PROTEIN-2

(75) Inventors: Jeffrey Friedman, New York, NY (US); Kristina Hedbacker, New York, NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 13/126,492

(22) PCT Filed: Oct. 29, 2009

(86) PCT No.: PCT/US2009/062604
§ 371 (c)(1),
(2), (4) Date: Jul. 15, 2011

(87) PCT Pub. No.: WO2010/096125
PCT Pub. Date: Aug. 26, 2010

(65) Prior Publication Data
US 2011/0263495 A1  Oct. 27, 2011

Related U.S. Application Data

(60) Provisional application No. 61/109,417, filed on Oct. 29, 2008.

(51) Int. Cl.
  *A61K 38/00* (2006.01)
  *A61K 38/28* (2006.01)
  *A61P 3/10* (2006.01)
(52) U.S. Cl. ............................ 514/8.7; 514/6.9; 514/7.3
(58) Field of Classification Search .................. None
  See application file for complete search history.

(56) References Cited

U.S. PATENT DOCUMENTS

| | | | |
|---|---|---|---|
| 6,040,292 | A | 3/2000 | Sommer |
| 7,071,160 | B2 * | 7/2006 | Yamano et al. ............... 514/1.9 |
| 2002/0028764 | A1 | 3/2002 | Grofte et al. |
| 2003/0087806 | A1 | 5/2003 | Danko et al. |
| 2008/0090765 | A1 | 4/2008 | Schmidt-Ott et al. |

FOREIGN PATENT DOCUMENTS

| | | |
|---|---|---|
| WO | 0023469 A2 | 4/2000 |
| WO | 2006034832 A2 | 4/2006 |
| WO | WO 2009/019254 * | 2/2009 |
| WO | 2010096125 | 8/2010 |

OTHER PUBLICATIONS

International Search Report and Written Opinion for PCT/US2009/062604 dated Jun. 28, 2010.
Firth et al., "Cellular Actions of the Insulin-Like Growth Factor Binding Proteins", Endocrine Reviews, Dec. 2002, pp. 824-854, vol. 23(6), The Endocrine Society.
Wheatcroft et al., "IGF-Binding Protein-2 Protects Against the Development of Obesity and Insulin Resistance", Diabetes, Feb. 2007, pp. 285-294, vol. 56(2).
Hedbacker et al., "Antidiabetic Effects of IGFBP2, a Leptin-Regulated Gene", Cell Metabolism, Jan. 2010, pp. 11-22, vol. 11(1).
Hedbacker et al., "Antidiabetic Effects of IGFBP2, a Leptin-Regulated Gene", Cell Metabolism, Mar. 3, 2010, p. 239, vol. 11(3).
Silha et al., "Minireview: Insights from Insulin-Like Growth Factor Binding Protein Transgenic Mice", Endocrinology, Oct. 2002, pp. 3711-3714, vol. 143(10).
Grarup et al., "Studies of Association of Variants Near the HHEX, CDKN2A/B, and IGF2BP2 Genes With Type 2 Diabetes and Impaired Insulin Release in 10,705 Danish Subjects", Diabetes, Dec. 2007, pp. 3105-3111, vol. 56.
Kelley et al., "Insulin-Like Growth Factor Binding Proteins (IGFBPs) and Their Regulatory Dynamics", International Journal of Biochemistry and Cell Biology, Jun. 1996, pp. 619-637, vol. 28(6).
Supplementary European Search Report and Written Opinion for Corresponding European Application No. 09840584.8 dated Jun. 22, 2012.

* cited by examiner

*Primary Examiner* — Shulamith H Shafer
(74) *Attorney, Agent, or Firm* — Thompson Coburn LLP

(57) ABSTRACT

The present invention is directed to methods of treating Type 1-diabetes by administering a therapeutically effective amount of an Insulin-like Growth Factor-binding protein-2. The present invention is also directed to methods treating Type 2 diabetes by administering a therapeutically effective amount of Insulin-like Growth Factor-binding protein-2. The present invention is further directed to methods treating insulin resistance by administering a therapeutically effective amount of Insulin-like Growth Factor-binding protein-2. The present invention is directed to methods of treating hepatic steatosis by administering a therapeutically effective amount of an Insulin-like Growth Factor-binding protein-2. The present invention is also directed to methods lowering blood glucose and serum insulin in non-diabetic subjects by administering a therapeutically effective amount of Insulin-like Growth Factor-binding protein-2.

14 Claims, 24 Drawing Sheets

| SYMBOL | Fold increase in 25 ng/hr leptin versus PBS treated mice. | Fold increase in 12.5 ng/hr leptin versus PBS treated mice. |
| --- | --- | --- |
| Serpina1e | 30.57 | 2.4 |
| Mup4 | 5.88 | 1.6 |
| Mup5 | 5.67 | 2.0 |
| Igfbp2 | 5.28 ** | 1.6 ** |
| OTTMUSG000000 | 5.11 | 1.8 |
| Igfbp2 | 4.59 ** | 1.5 ** |
| Keg1 | 4.35 | 1.9 |
| OTTMUSG00000 | 4.18 | 1.6 |
| C6 | 4.09 | 1.5 |
| EG13909 | 3.94 | 2.0 |
| C8b | 3.91 | 1.6 |
| D0H4S114 | 3.76 | 3.2 |
| C6 | 3.41 | 1.4 |
| Xlr4a | 3.39 | 1.8 |
| Egfr | 3.36 | 1.6 |
| Egfr | 3.30 | 1.5 |
| Egfr | 3.25 | 1.5 |
| Cfd | 3.20 | 2.5 |
| C8a | 3.18 | 1.9 |
| 2810007J24Rik | 3.00 | 1.8 |
| EG13909 | 2.88 | 1.9 |
| Aatk | 2.61 | 1.2 |
| Hsd3b5 | 2.40 | 1.0 |
| F11 | 2.36 | 1.9 |
| Cyp4f14 | 2.36 | 1.2 |
| F11 | 2.35 | 1.7 |
| Cxcl9 | 2.35 | 1.8 |
| EG13909 | 2.28 | 1.5 |
| Nudt7 | 2.22 | 1.4 |
| Mup2 | 2.13 | 1.5 |
| Mcm10 | 2.11 | 1.6 |
| C730004C24Rik | 2.11 | 1.3 |
| Nudt7 | 2.08 | 1.5 |
| Bcl6 | 2.08 | 0.4 |
| Cyp7b1 | 2.08 | 1.3 |
| LOC620807 | 2.01 | 1.4 |

FIG. 8

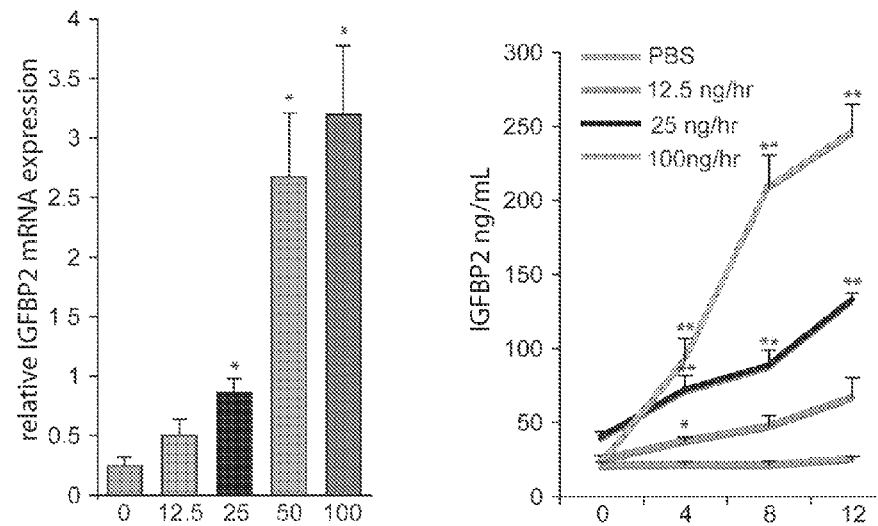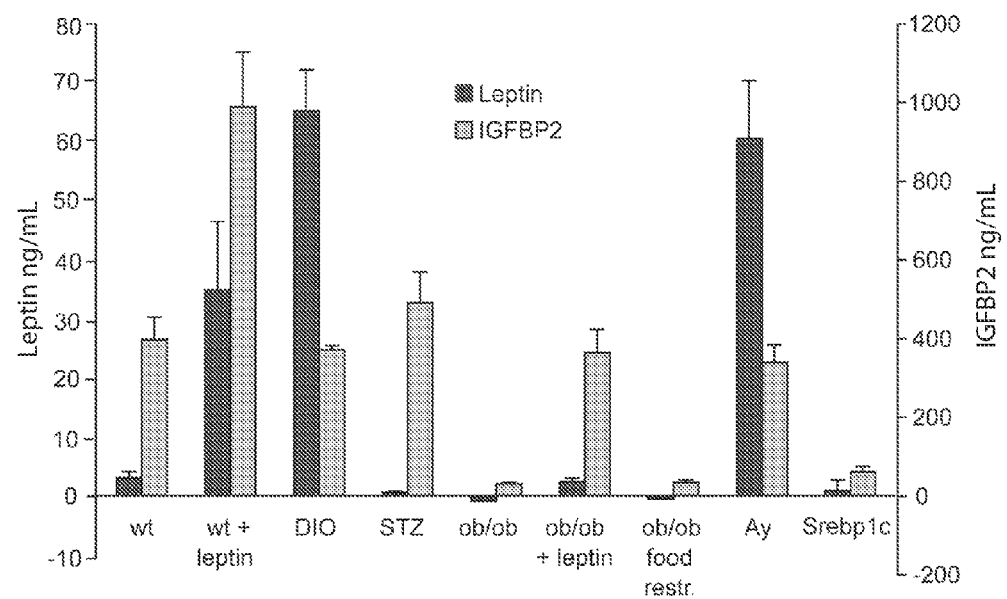
FIG. 9

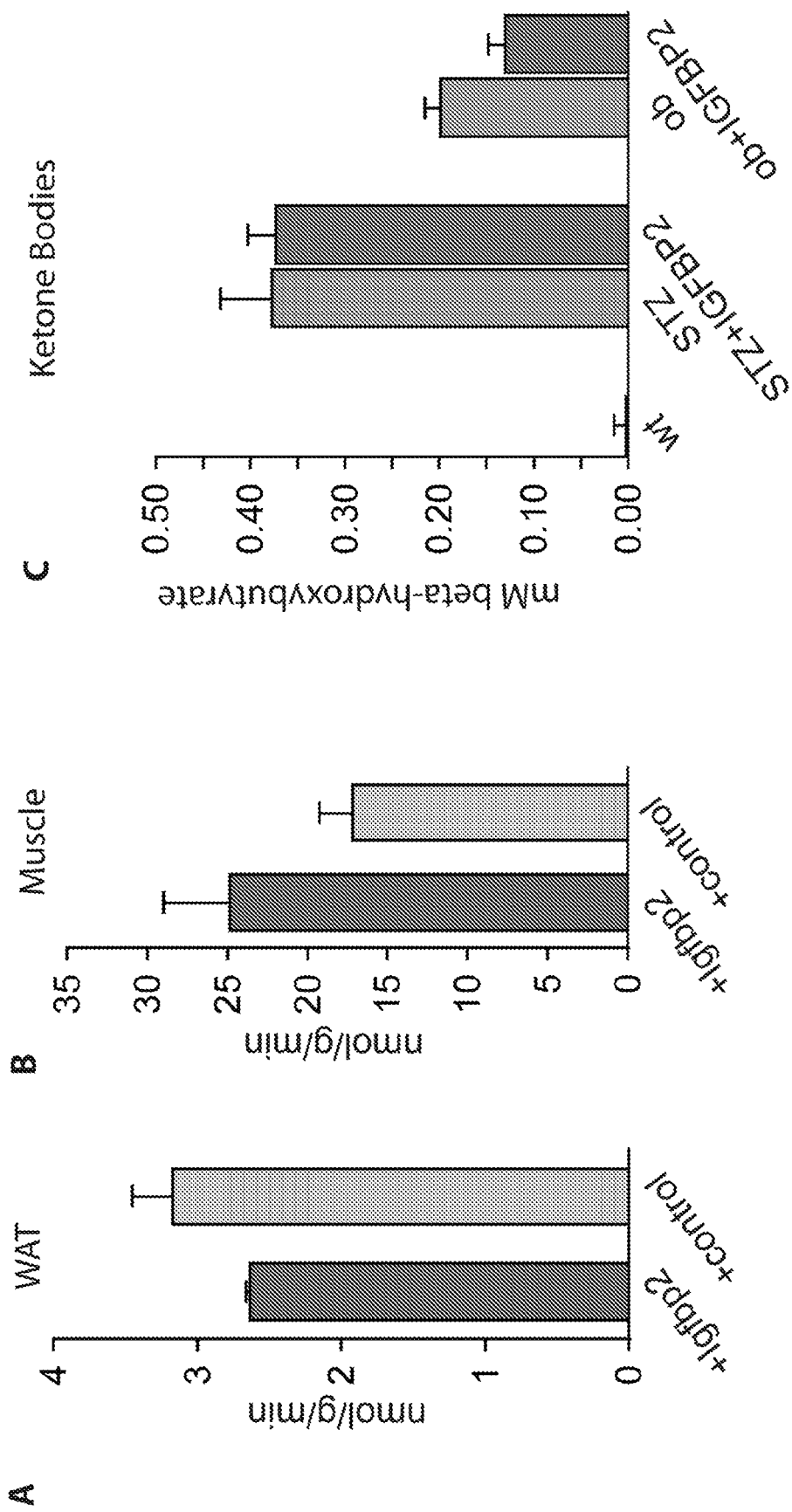
FIG. 10 (a, b, c)

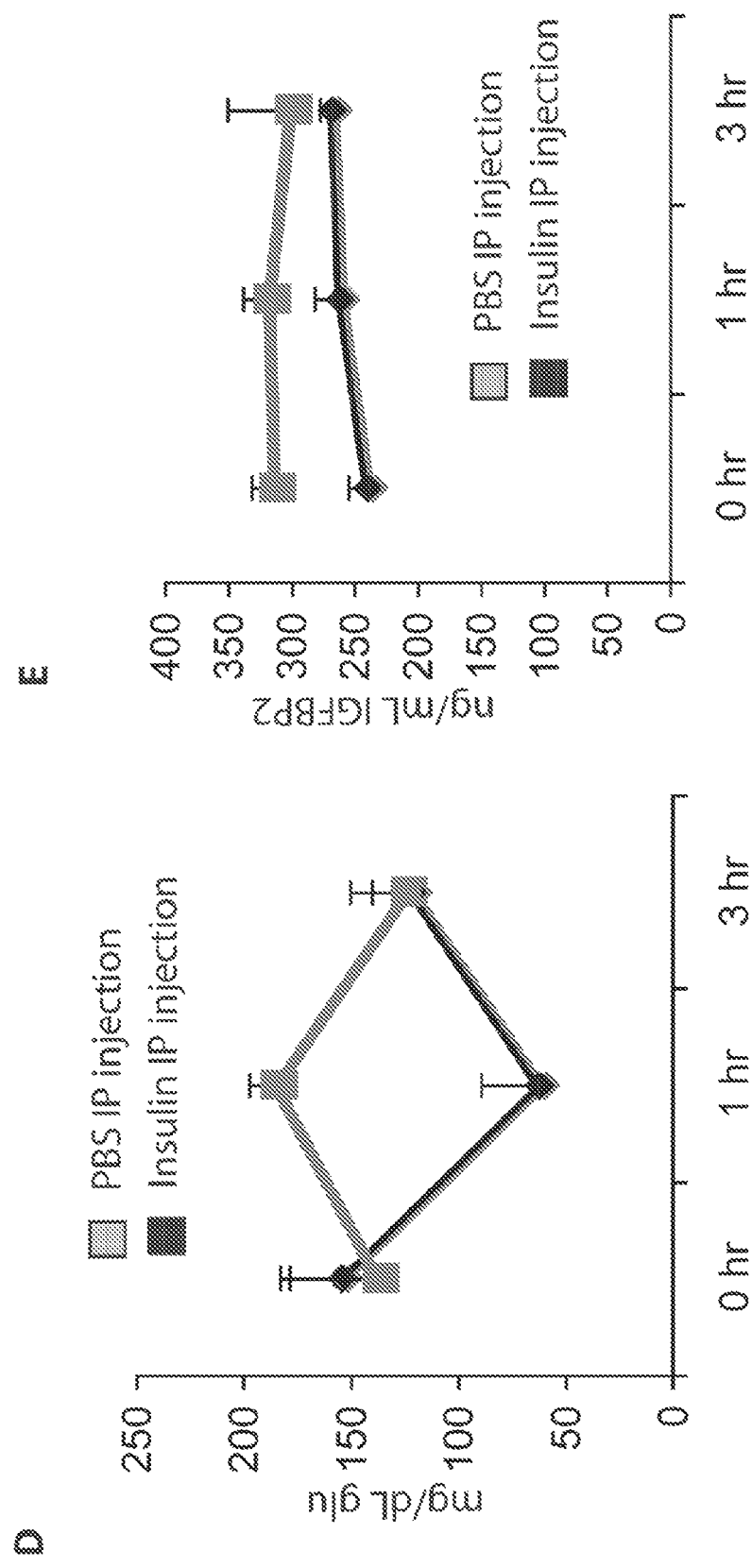
FIG. 10 (d, e)

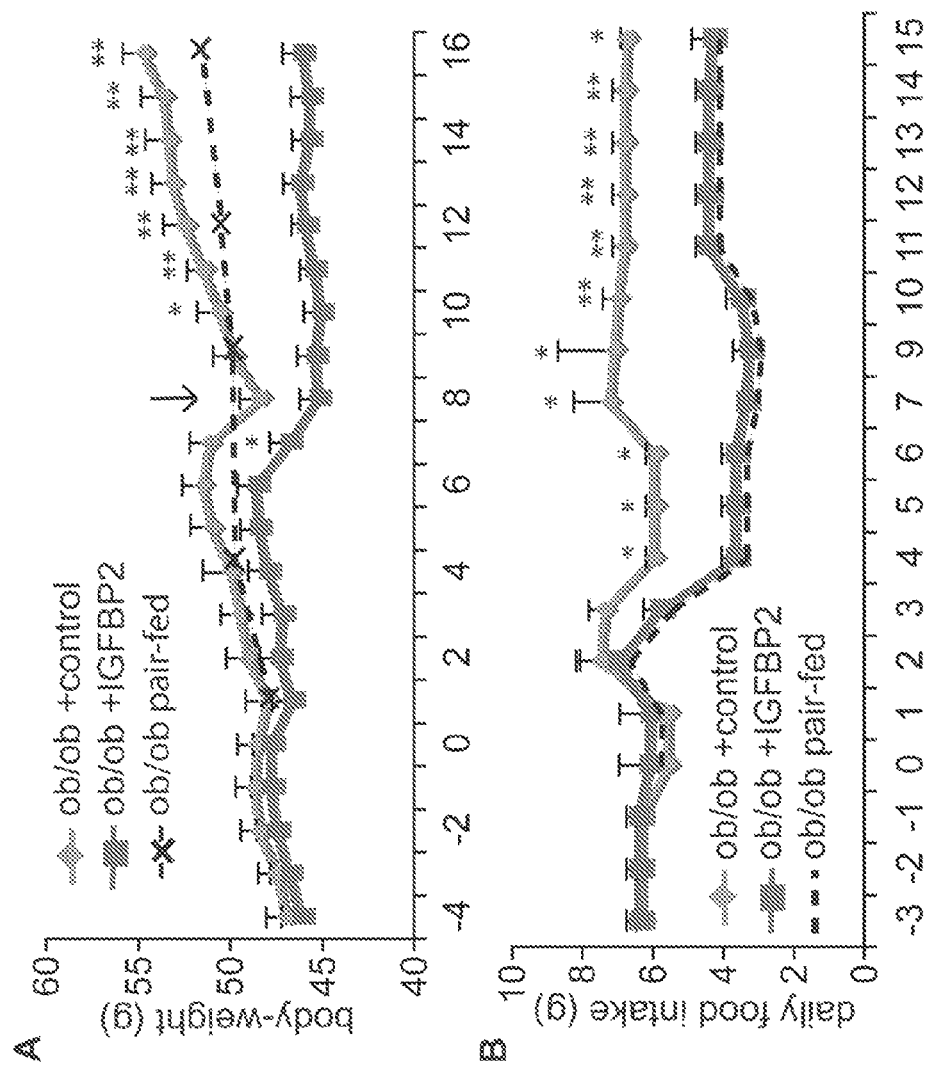
FIG. 12 (a, b)

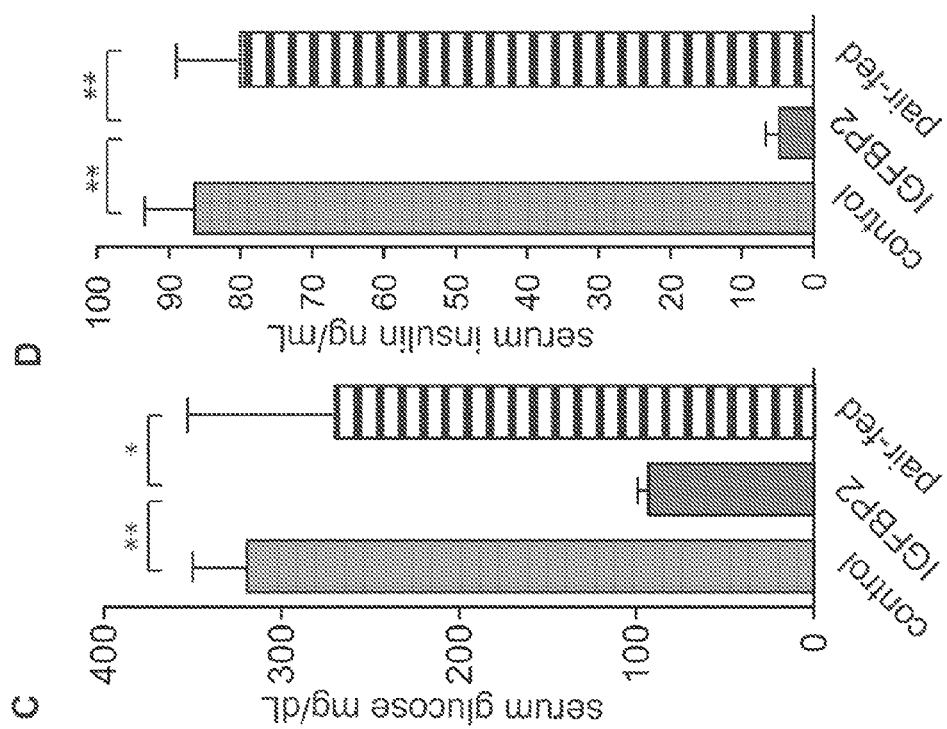
FIG. 12 (c, d)

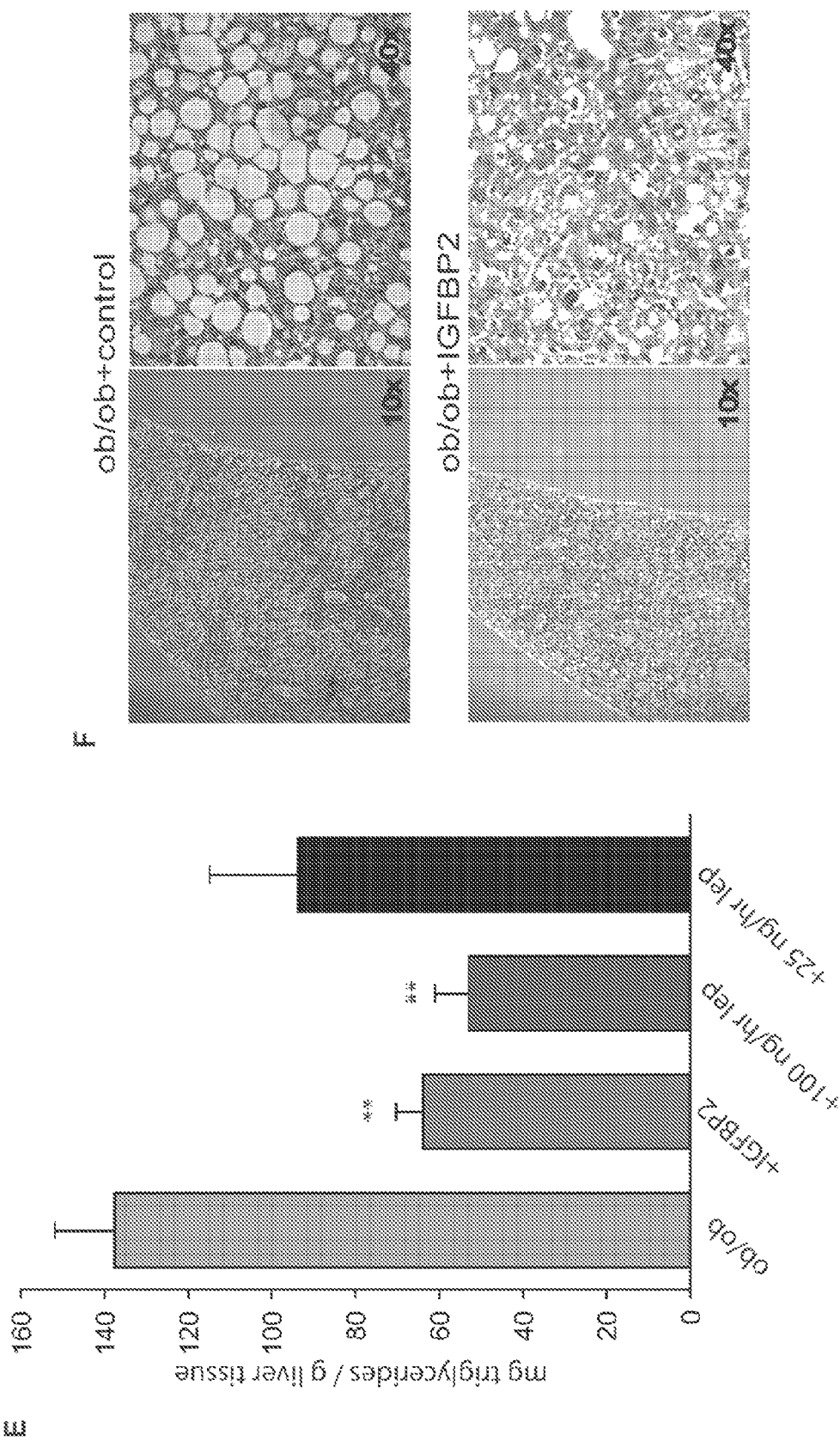
FIG. 12 (e, f)

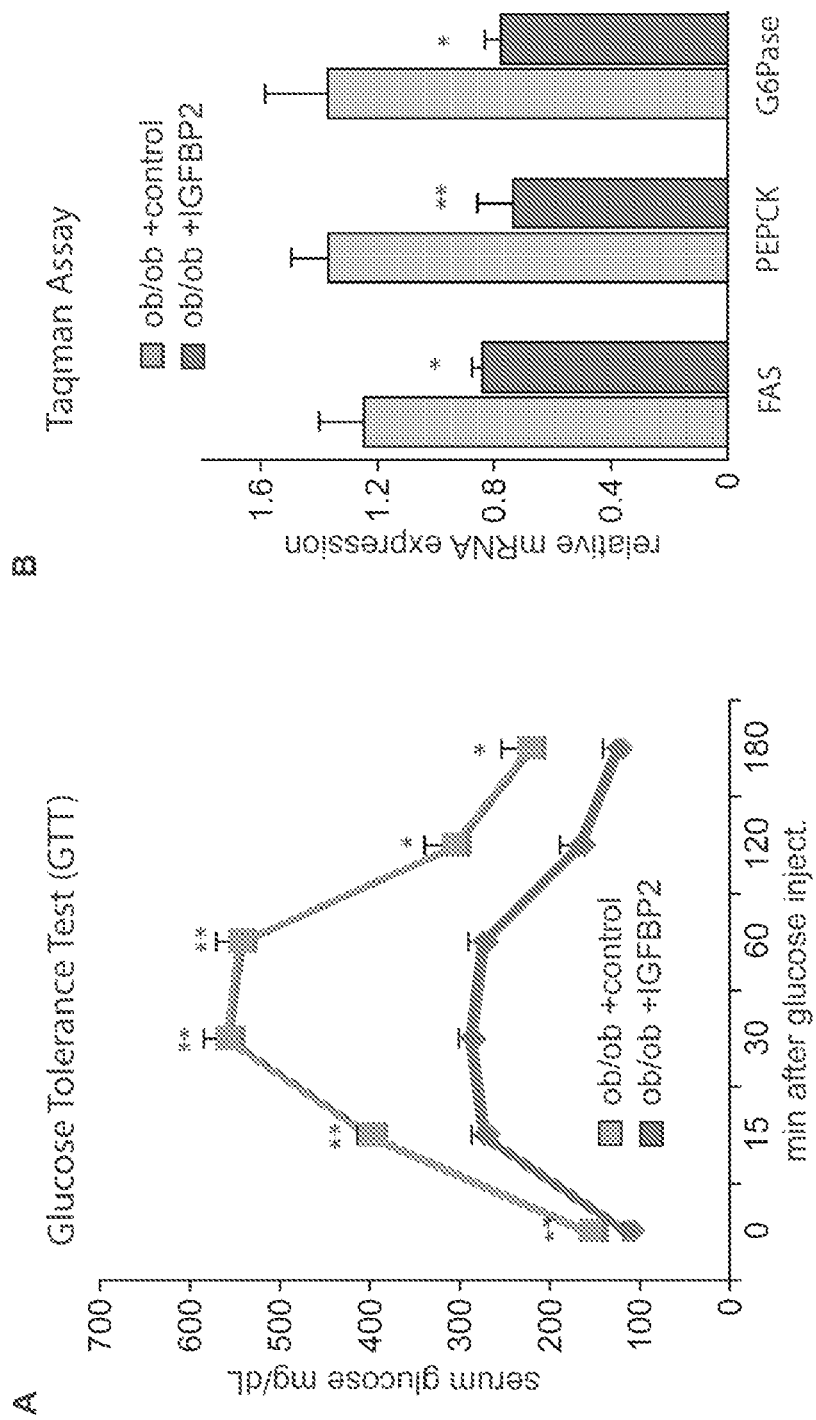
FIG. 13 (a, b)

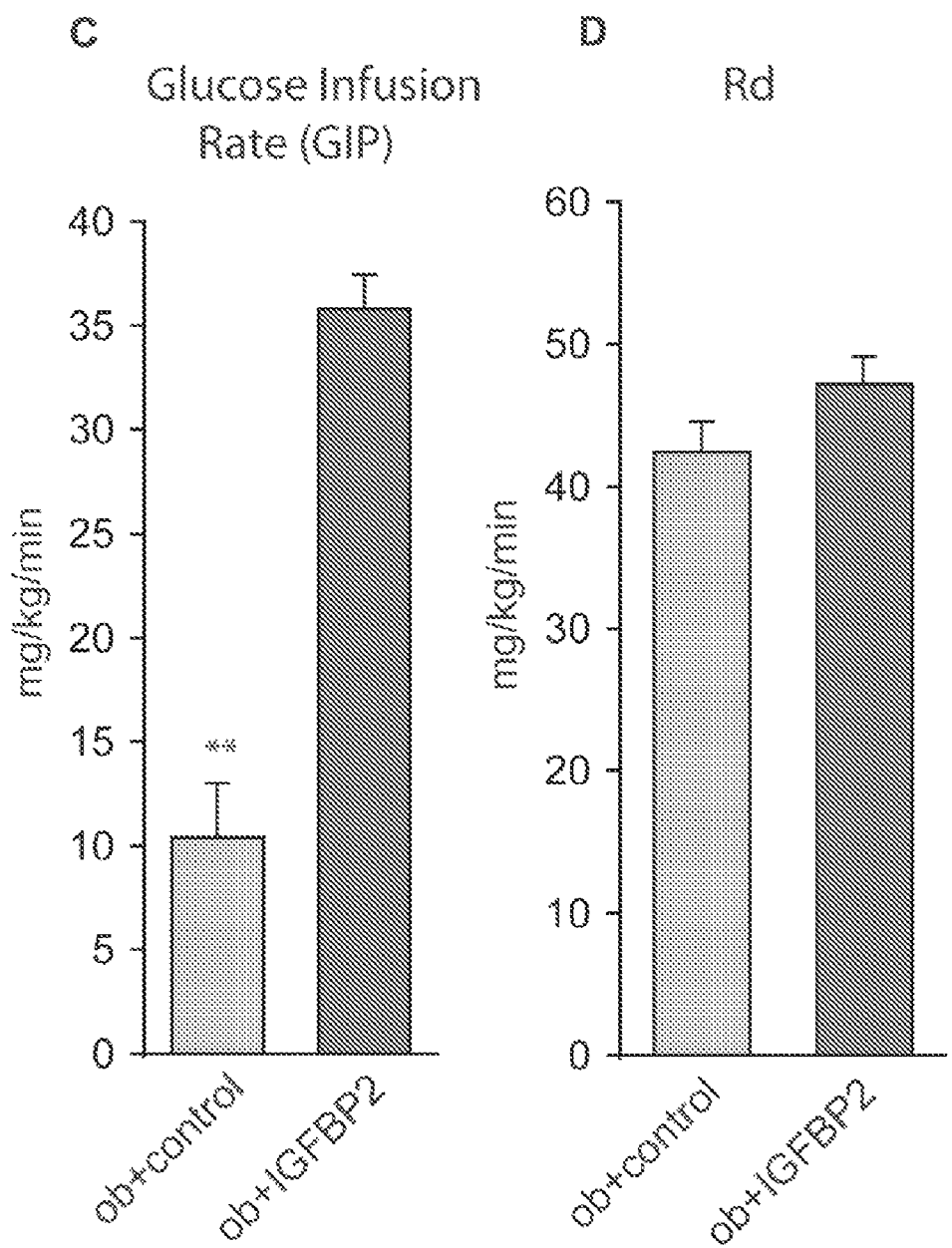
FIG. 13 (c, d)

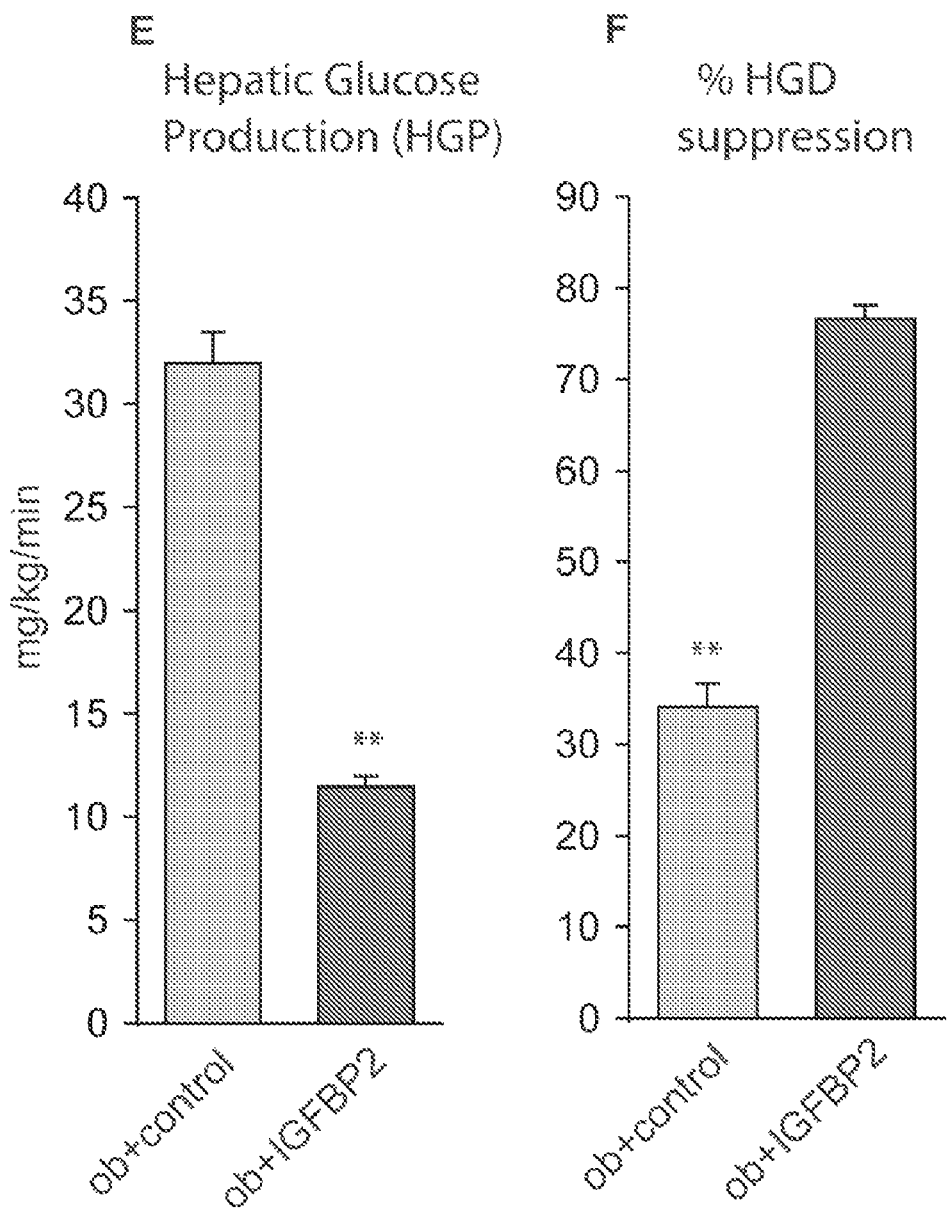
FIG. 13 (e, f)

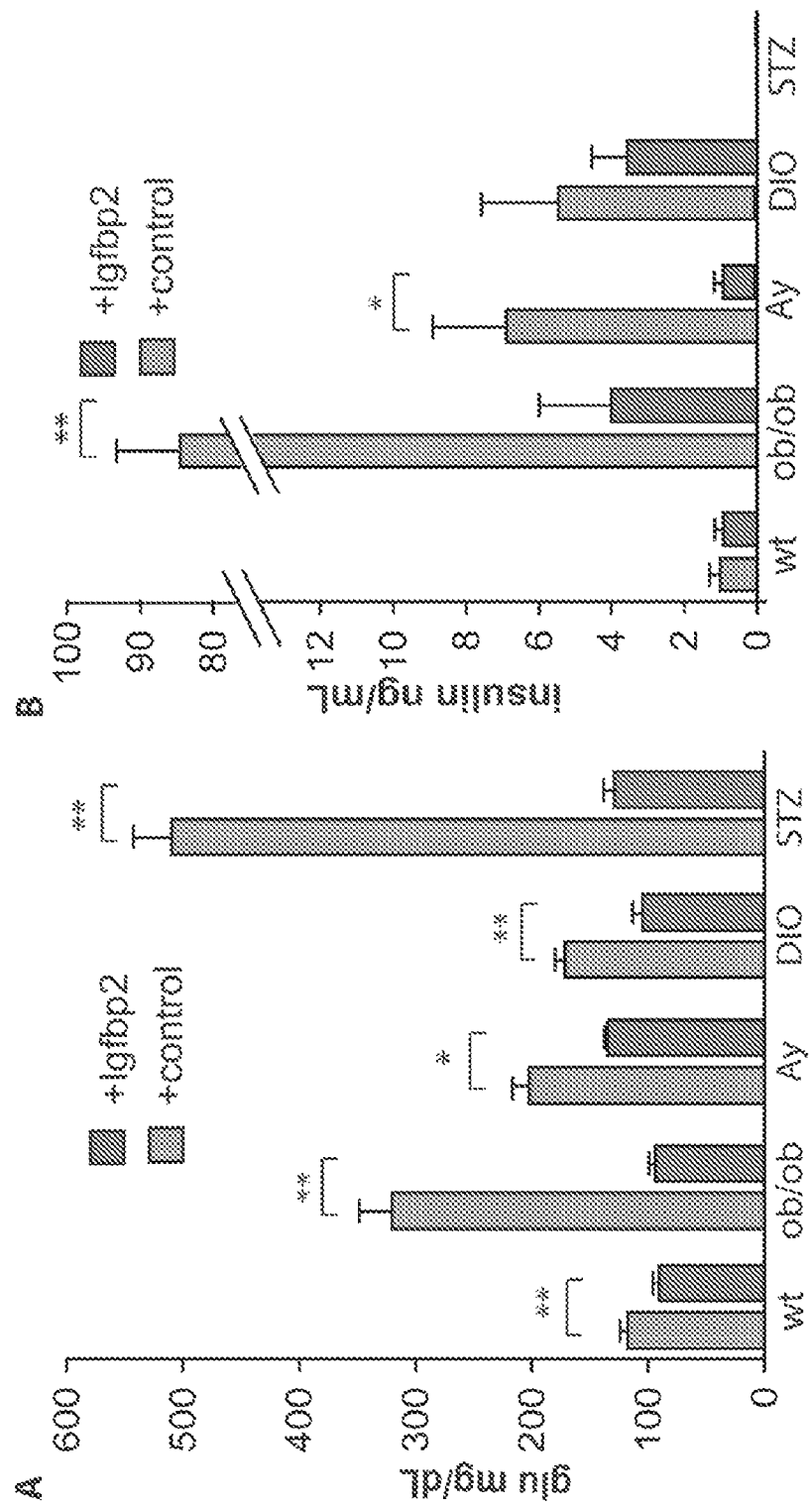
FIG. 14(a, b)

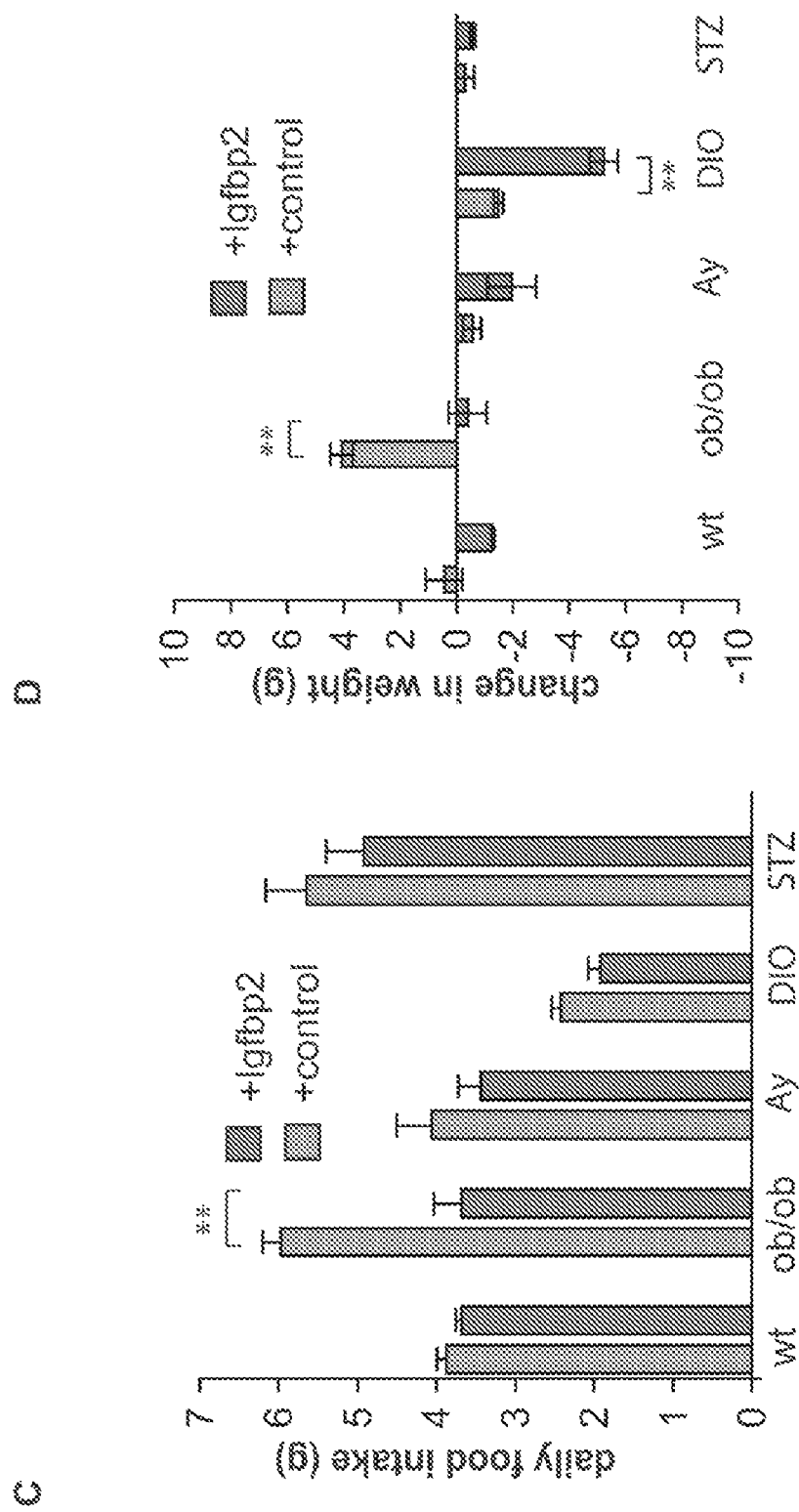
FIG. 14 (c, d)

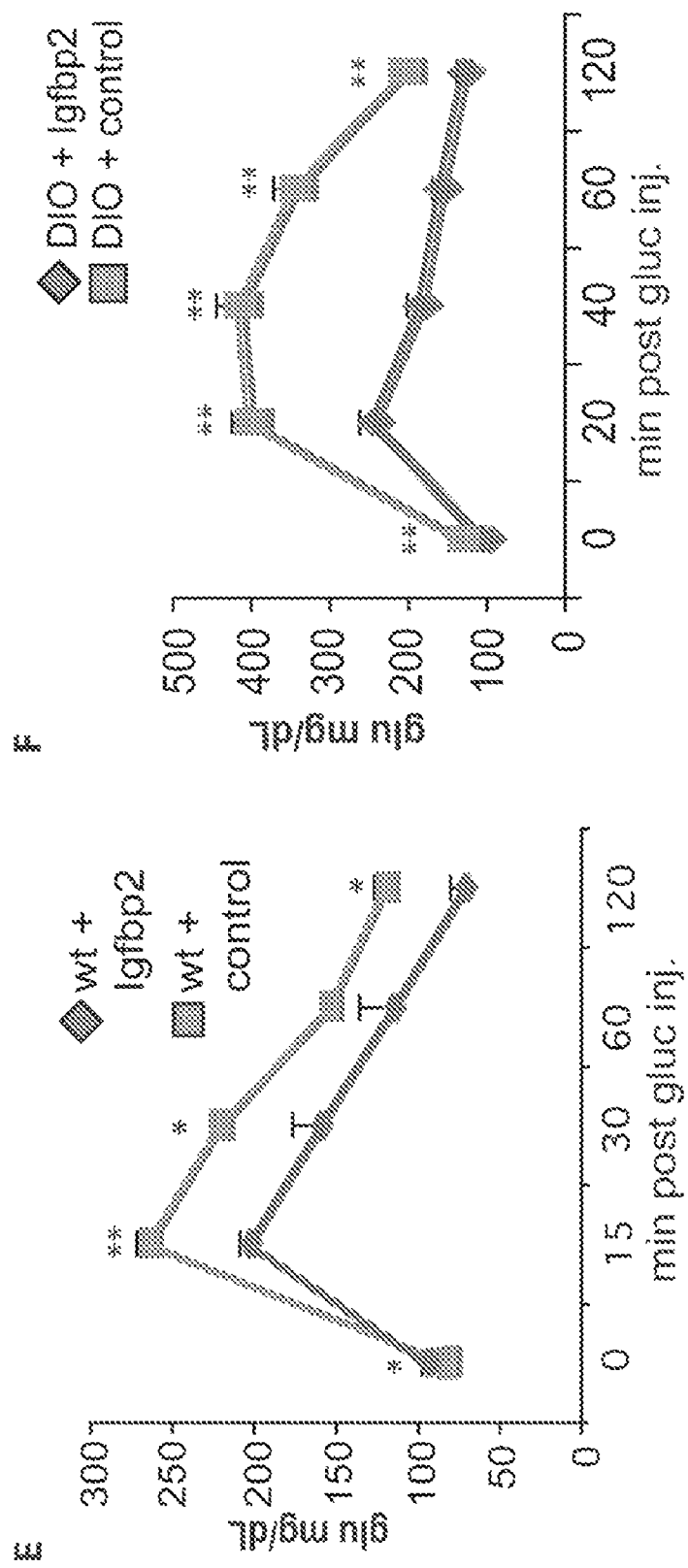
FIG. 14(e, f)

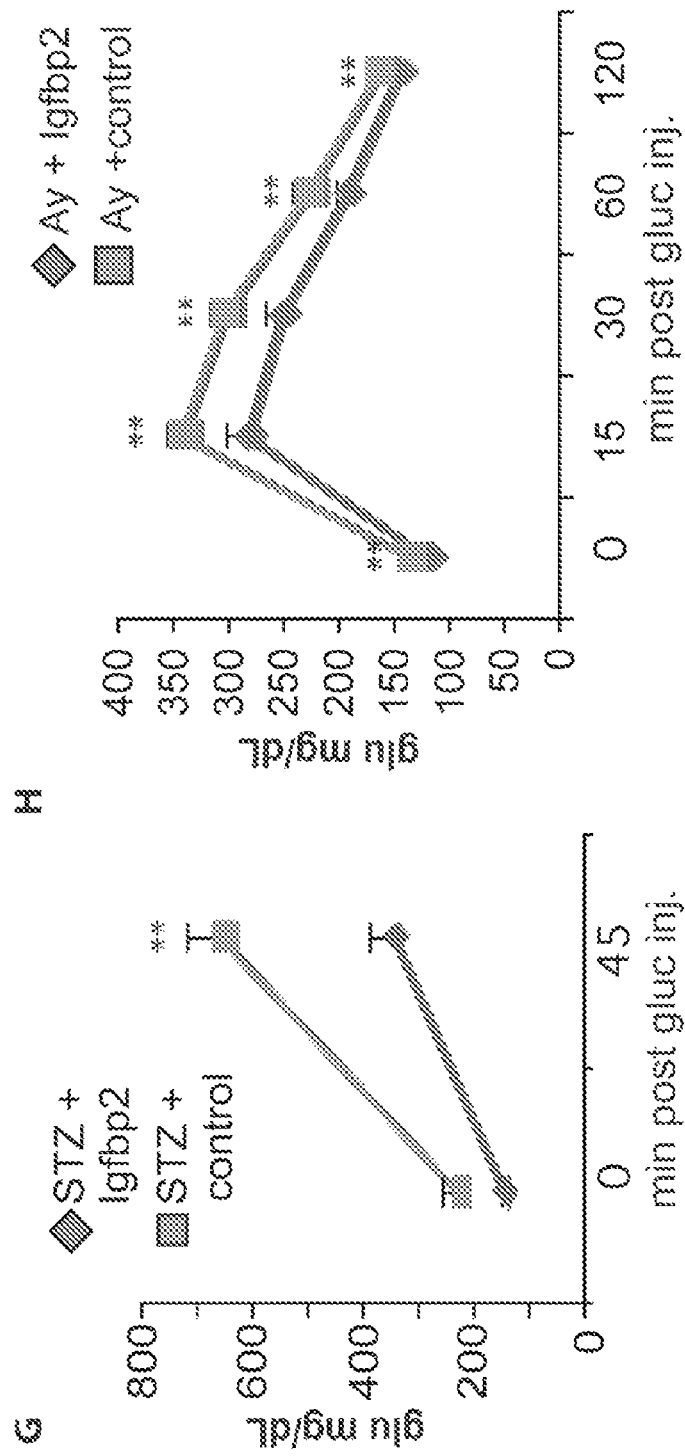
FIG. 14 (g, h)

METHODS AND KITS FOR TREATING DISEASE BY ADMINISTERING INSULIN-LIKE GROWTH FACTOR BINDING PROTEIN-2

CROSS REFERENCE TO RELATED APPLICATIONS

This application is a National Stage application of International Patent Application No. PCT/US2009/062604, filed Oct. 29, 2009, which is incorporated herein by reference in its entirety and which claims the benefit of U.S. Provisional Application Ser. No. 61/109,417 filed Oct. 29, 2008, which is incorporated herein by reference in its entirety.

INCORPORATION OF SEQUENCE LISTING

A computer readable form of the sequence listing is provided herewith, containing the file named "49248-96461_Seq_Listing_ST25.txt", which is 82790 bytes in size (measured in MS-DOS), and is herein incorporated by reference. This Sequence Listing consists of SEQ ID NOs: 1-30.

BACKGROUND OF THE INVENTION

Diabetes is a major public health epidemic in the United States. The aetiology of diabetes is hyperglycemia, which have a tremendous impact on morbidity when left untreated. Diabetes is associated with an increased risk for a number of complications including, heart disease and stroke, high blood pressure, blindness, kidney disease, nervous system disease, amputation, dental disease, and pregnancy complications.

Diabetes is classified into two types: Type 1 and Type 2. Type 1 diabetes, also known as insulin-dependent diabetes mellitus (IDDM), is believed to be caused by autoimmune destruction of pancreatic beta cells, which produce and secrete insulin. Type 2 diabetes, also known as non-insulin-dependent diabetes mellitus (NIDDM), is characterized by the failure of the body to respond normally to insulin and a gradual loss in the ability of the pancreas to produce insulin.

Insulin-like growth factor binding protein-2 ("IGFBP-2") is one of 6 homologous IGFBPs and the second most abundant IGFBP in serum (Jones, J. I. & Clemmons, D. R. Insulin-like growth factors and their binding proteins: biological actions. Endocr. Rev. 16, 3-34 (1995)). IGFBPs are thought to inhibit the action of insulin-like growth factors ("IGFs") through high-affinity binding that regulates access of IFGs to target tissues and reduce IGF bioactivity. IGFBP-2 has been linked with Type 2 diabetes in several large genome wide association studies (Grarup et al. 56 Diabetes 3105-3111 (2007)). Transgenic IGFBP-2 over-expression in mice showed reduced diet-induced obesity and associated complications (Wheatcroft et al., 56 Diabetes 285-294 (2007)). A direct role for IGFBP-2 in glucose metabolism and insulin regulation however, has not been established.

Currently therapies for diabetes tend to focus on insulin-replacement or augmentation. Accordingly, a need exists for additional treatment options.

SUMMARY OF THE INVENTION

In certain embodiments, the invention provides methods of treating Type 1 diabetes comprising the step of administering a therapeutically effective amount of an Insulin-like Growth Factor-binding protein-2 (IGFBP-2) to a subject in need thereof. In some embodiments, the subject in need thereof may be a mammal. In other embodiments, the subject in need thereof may be a human. In certain embodiments, the Insulin-like Growth Factor-binding protein-2 is administered to the subject orally, topically, rectally, percutaneously, by parenteral injection, intranasally, or by inhalation. In certain embodiments, the therapeutically effective amount of Insulin-like Growth Factor-binding protein-2 administered comprises an amount that provides for an increase of at least about 2-fold to about 5-fold in a blood serum level of IGFBP-2 in said subject. In certain embodiments, the therapeutically effective amount provides for a fasting blood serum glucose level of about 90 mg/dL to 105 mg/dL. In certain embodiments, the therapeutically effective amount provides for blood serum glucose levels of less than 300 mg/dL at 45 minutes post intraperitoneal injection administration of a glucose solution at a dose of 1 unit glucose per gram of mouse of said subject.

In certain embodiments, the invention provides methods of treating Type 2 diabetes comprising the step of administering a therapeutically effective amount of Insulin-like Growth Factor-binding protein-2 to a subject in need thereof. In some embodiments, the subject in need thereof may be a mammal. In other embodiments, the subject in need thereof may be a human. In certain embodiments, the Insulin-like Growth Factor-binding protein-2 is administered to the subject orally, topically, rectally, percutaneously, by parenteral injection, intranasally, or by inhalation. In certain embodiments, the therapeutically effective amount of Insulin-like Growth Factor-binding protein-2 administered comprises an amount that provides for an increase of at least about 2-fold to about 5-fold in a blood serum level of IGFBP-2 in said subject. In certain embodiments, the therapeutically effective amount provides for a fasting blood serum glucose level of about 80 mg/dL to 110 mg/dL. In certain embodiments, the therapeutically effective amount results in a fasting blood serum insulin level of about 3 ng/mL to about 7 ng/mL.

In certain embodiments, the invention provides methods of treating insulin resistance comprising the step of administering a therapeutically effective amount of Insulin-like Growth Factor-binding protein-2 to a subject in need thereof. In some embodiments, the subject in need thereof may be a mammal. In other embodiments, the subject in need thereof may be a human. In certain embodiments, the Insulin-like Growth Factor-binding protein-2 is administered to the subject orally, topically, rectally, percutaneously, by parenteral injection, intranasally, or by inhalation. In certain embodiments, the therapeutically effective amount of Insulin-like Growth Factor-binding protein-2 administered comprises an amount that provides for an increase of at least about 2-fold to about 5-fold in a blood serum level of IGFBP-2 in said subject. In certain embodiments, the therapeutically effective amount provides for a fasting blood serum glucose level of about 80 mg/dL to 110 mg/dL. In certain embodiments, the therapeutically effective amount results in a fasting blood serum insulin level of about 3 ng/mL to about 7 ng/mL.

In certain embodiments, the invention provides methods of treating hepatic steatosis comprising the step of administering a therapeutically effective amount of Insulin-like Growth Factor-binding protein-2 to a subject in need thereof. In some embodiments, the subject in need thereof may be a mammal. In other embodiments, the subject in need thereof may be a human. In certain embodiments, the Insulin-like Growth Factor-binding protein-2 is administered to the subject orally, topically, rectally, percutaneously, by parenteral injection, intranasally, or by inhalation. In certain embodiments, the therapeutically effective amount of Insulin-like Growth Factor-binding protein-2 administered comprises an amount that provides for an increase of at least about 2-fold to about 5-fold in a blood serum level of IGFBP-2 in said subject.

In certain embodiments, the invention provides methods of lowering blood glucose and insulin levels comprising the step of administering a therapeutically effective amount of Insulin-like Growth Factor-binding protein-2 to a subject in need thereof. In some embodiments, the subject in need thereof may be a mammal. In other embodiments, the subject in need thereof may be a human. In certain embodiments, the Insulin-like Growth Factor-binding protein-2 is administered to the subject orally, topically, rectally, percutaneously, by parenteral injection, intranasally, or by inhalation. In certain embodiments, the therapeutically effective amount of Insulin-like Growth Factor-binding protein-2 administered comprises an amount that provides for an increase of at least about 2-fold to about 5-fold in a blood serum level of IGFBP-2 in said subject. In certain embodiments, the therapeutically effective amount provides for a blood glucose level of about 80 mg/dL to 90 mg/dL. In certain embodiments, the therapeutically effective amount provides for a fasting blood serum insulin level of about 0.01 mg/dL to 0.05 mg/dL.

In certain embodiments of the aforementioned methods, the therapeutically effective amount of an Insulin-like Growth Factor-binding protein-2 (IGFBP-2) is provided by administration of a recombinant Insulin-like Growth Factor-binding protein-2 (IGFBP-2) or a PEGlyated recombinant IGFBP-2 protein to said subject. In other embodiments of the aforementioned methods, the therapeutically effective amount of an Insulin-like Growth Factor-binding protein-2 (IGFBP-2) is provided by administration of a recombinant nucleic acid vector comprising a nucleic acid sequence encoding Insulin-like Growth Factor-binding protein-2 operably linked to a heterologous expression control sequence to said subject.

In certain embodiments of the aforementioned methods, the therapeutically effective amount of an Insulin-like Growth Factor-binding protein-2 (IGFBP-2) administered provides for a blood serum IGFBP-2 protein concentration that is at least about 2-fold to about 25-fold above a blood serum IGFBP-2 protein concentration in either: i) an untreated subject; or ii) in a healthy reference subject. In certain embodiments of the aforementioned methods, the therapeutically effective amount of an Insulin-like Growth Factor-binding protein-2 (IGFBP-2) administered provides for a blood serum IGFBP-2_protein concentration that is at least about 5-fold to about 20-fold above a blood serum IGFBP-2 protein concentration in either: i) an untreated subject; or ii) in a healthy reference subject. In certain embodiments of the aforementioned methods, the therapeutically effective amount of an Insulin-like Growth Factor-binding protein-2 (IGFBP-2) administered provides for a blood serum IGFBP-2 protein concentration that is at least about 8-fold to about 15-fold above a blood serum IGFBP-2 protein concentration in either: i) an untreated subject; or ii) in a healthy reference subject. In certain embodiments of the aforementioned methods, the therapeutically effective amount of an Insulin-like Growth Factor-binding protein-2 (IGFBP-2) administered provides for a blood serum IGFBP-2 protein concentration that is at least about 2-, 5-, or 8-fold to about 15-, 18-, 20-, or 25-fold above a blood serum IGFBP-2 protein concentration in either: i) an untreated subject; or ii) in a healthy reference subject.

In certain embodiments, the invention provides kits having a pharmaceutical composition comprising (i) a therapeutically effective amount of Insulin-like Growth Factor-binding protein-2; and (ii) one or more pharmaceutically acceptable carriers; one or more containers for said pharmaceutical composition; and instructions for the use thereof in treating Type 1 diabetes.

In certain embodiments, the invention provides kits having a pharmaceutical composition comprising (i) a recombinant nucleic acid vector containing a nucleic acid sequence encoding Insulin-like Growth Factor-binding protein-2 operably linked to a heterologous expression control sequence or a therapeutically effective amount of Insulin-like Growth Factor-binding protein-2; one or more containers for said pharmaceutical composition; and instructions for the use thereof in treating Type 2 diabetes.

In certain embodiments, the invention provides kits having a pharmaceutical composition comprising (i) a recombinant nucleic acid vector containing a nucleic acid sequence encoding Insulin-like Growth Factor-binding protein-2 operably linked to a heterologous expression control sequence; one or more containers for said pharmaceutical composition; and instructions for the use thereof in treating insulin resistance.

In certain embodiments, the invention provides kits having a pharmaceutical composition comprising (i) a therapeutically effective amount of Insulin-like Growth Factor-binding protein-2; one or more containers for said pharmaceutical composition; and instructions for the use thereof in treating insulin resistance.

In certain embodiments, the invention provides kits having a pharmaceutical composition comprising (i) a recombinant nucleic acid vector containing a nucleic acid sequence encoding Insulin-like Growth Factor-binding protein-2 operably linked to a heterologous expression control sequence or a therapeutically effective amount of Insulin-like Growth Factor-binding protein-2; one or more containers for said pharmaceutical composition; and instructions for the use thereof in treating hepatic steatosis.

In certain embodiments, the invention provides kits having a pharmaceutical composition comprising (i) a recombinant nucleic acid vector containing a nucleic acid sequence encoding Insulin-like Growth Factor-binding protein-2 operably linked to a heterologous expression control sequence or a therapeutically effective amount of Insulin-like Growth Factor-binding protein-2; one or more containers for said pharmaceutical composition; and instructions for the use thereof in lowering blood glucose levels.

In certain embodiments, the invention provides kits having a pharmaceutical composition comprising (i) a recombinant nucleic acid vector containing a nucleic acid sequence encoding Insulin-like Growth Factor-binding protein-2 operably linked to a heterologous expression control sequence or a therapeutically effective amount of Insulin-like Growth Factor-binding protein-2; one or more containers for said pharmaceutical composition; and instructions for the use thereof in lowering serum insulin levels.

In certain embodiments, the invention provides kits having a pharmaceutical composition comprising (i) a recombinant nucleic acid vector containing a nucleic acid sequence encoding Insulin-like Growth Factor-binding protein-2 operably linked to a heterologous expression control sequence or a therapeutically effective amount of Insulin-like Growth Factor-binding protein-2; one or more containers for said pharmaceutical composition; and instructions for the use thereof treating hyperphagia and consequential weight gain.

BRIEF DESCRIPTION OF THE DRAWINGS

FIG. 8 is a table showing fold increases in expression of various genes with indicated leptin treatments relative to PBS treated controls.

FIG. 9 provides data on leptin regulation of IGFBP2. A) Relative IGFBP2 mRNA expression in liver samples from ob/ob mice leptin-treated for 12 days as indicated. B) Plasma IGFBP2 levels in ob/ob mice during treatment with leptin at the indicated concentrations. C) Plasma leptin (left y-axis) and plasma IGFBP2 (right y-axis) in mice as follows: wt=wild type, wt+leptin=wildtype after 8 days of 1 ug/hr leptin, DIO=diet-induced obese (high-fat diet for 15 weeks), STZ=streptozotocin diabetic, ob/ob mice, ob/ob+leptin=ob/ob after 12 days of 100 ng/hour leptin treatment, ob/ob food restr.=ob/ob after 12 days of food restriction to 0.5 g/day (insulin levels 1/10th of free-feeding—data not shown), Ay=agouti, Srebp-1c. Grey bars indicate IGFBP2. Black bars indicate leptin levels in same animals. Error bars show standard error. $*p<0.05$, $**p<0.01$.

FIG. 12 shows that IGFBP2 treatment corrects hyperglycemia, hyperinsulinemia, and hepatic steatosis in ob/ob diabetic mice. ob/ob mice treated with Ad-control (diamond) or Ad-IGFBP2 (square) or untreated and pair-fed to Ad-IGFBP2. $N \geq 4$. A) and B) Body weight and food intake in grams. Food intake is average for 24 hours. Mice injected with adenovirus on day '0'. Arrow indicates 18-hour fast (for GTT). X-axis indicates day of experiment. Dotted line shows body weight and food intake of mice pair-fed to the IGFBP2 treated mice. C) and D) plasma glucose and plasma insulin in treated, control, and pair-fed mice. E) Milligrams triglycerides per gram liver tissue in ob/ob control, ob/ob+IGFBP2, ob/ob+12 days 100 ng/hr leptin and ob/ob+ 12 days of 25 ng/hr leptin. F) H&E stained liver paraffin sections of treated and control mice. 10× and 40× as indicated. $*p<0.05$, $**p<0.01$.

FIG. 13 shows that IGFBP2 treatment improves glucose metabolism in ob/ob Type 2 diabetic mice. Diamond=IGFBP2 treated ob/ob mice (lower, dark plot), square=control treated ob/ob mice (upper, light plot). $*p<0.05$, $**p<0.01$. n=7. A) Glucose tolerance test (GTT) in ob/ob mice. B) Relative IGFBP2 mRNA expression in frozen liver samples from ob/ob mice ~3 weeks after Ad-IGFBP2 or Ad-control infection. Fatty acid synthase (FAS), PEPCK, and G6Pase. C) Glucose infusion rate (GIR) in mg/kg/min necessary to keep hyperinsulinemic mice euglycemic during clamp studies. D) Rd (whole body glucose disappearance in mg/kg/min). E) Hepatic glucose production (HGP) in mg/kg/min. F) Percent suppression of hepatic glucose production in response to hyperinsulinemic clamp.

FIG. 14 shows Comparison of effect of IGFBP2 treatment on blood glucose, insulin, daily food intake, body weight and glucose tolerance in wild types, ob/ob, Ay, STZ and DIO mice. Dark=Ad-IGFBP2 treated (right bar of test pair in 14a-d), light=Ad-control treated (left bar of test pair in 14a-d). $*p<0.05$, $**p<0.01$. wt=wildtype, Ay=Agouti, DIO=diet-induced obese (15 weeks on high-fat diet), STZ=streptozytocin-induced Type 1 diabetic mice. Blood glucose and insulin taken on day 5 or 6 post-infection. Daily food intake is average of day 4-14 post-infection. Change in weight is total change in weight from day 4-14 post-infection.

DETAILED DESCRIPTION

Definitions

Figure 1:
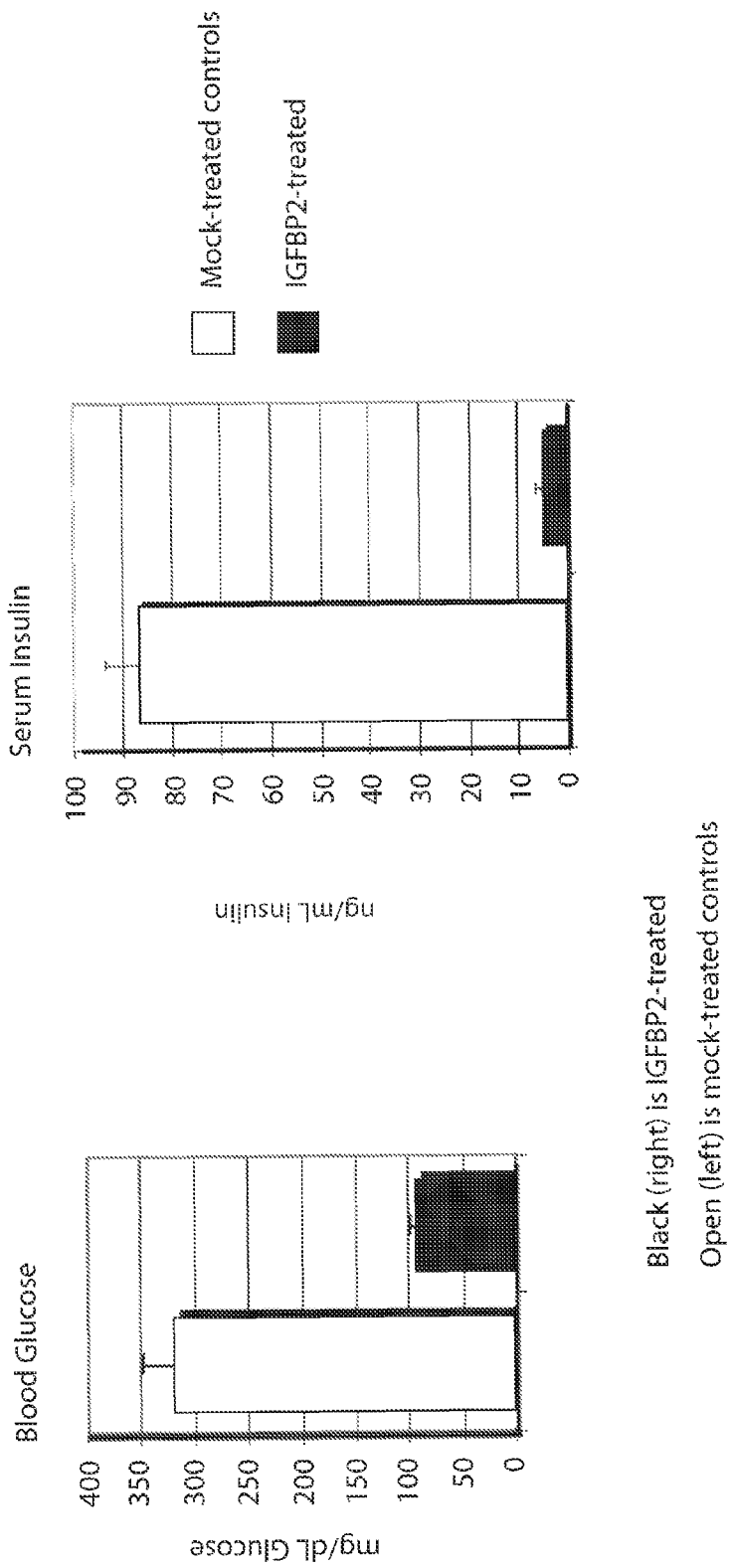
FIG. 1 is a graph showing blood glucose and serum insulin levels in ob/ob mice treated with IGFBP-2. The bar on the right side of both panels are the IGFBP-2 treated and the bar on the left side of both panels are the mock treated controls.

Unless otherwise defined, all technical and scientific terms used herein have the same meaning as commonly understood by one of ordinary skill in the art to which this invention pertains. In the case of inconsistencies between the present disclosure and the issued patents, applications, and references that are cited herein or elsewhere, the present disclosure will prevail.

As used herein, "Type 1 diabetes", refers to the disease state wherein the subject has an insulin deficiency.

The phrase "therapeutically effective amount", as used herein, refers to an amount that provides for a reduction in the severity of one or more symptoms associated with a given disease.

The phrase "deficiency", as used herein, in the context of a subject, refers to any reduction in an amount of a substance to any level that is suboptimal for the health of the subject.

The term "fasting", as used herein, in the context of various testing regimens, refers to the process whereby a subject refrains from intake of nutrients for at least eight hours.

The term "insensitivity", as used herein, refers to any reduction in sensitivity.

The terms "polypeptide," "peptide" and "protein" are used interchangeably herein, to refer to a polymer of amino acid residues of any length.

The phrase "heterologous expression control sequence", as used herein, refers to nucleic acid sequences that regulate the expression of a nucleic acid sequence to which it is operatively linked. Expression control sequences are sequences that control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); and sequences that enhance protein stability.

The phrase "operably linked", as used herein, refers to the joining of nucleic acid sequences such that one sequence can provide a required function to a linked sequence. In the context of a promoter, "operably linked" means that the promoter is connected to a sequence of interest such that the transcription of that sequence of interest is controlled and regulated by that promoter. When the sequence of interest encodes a protein and when expression of that protein is desired, "operably linked" means that the promoter is linked to the sequence in such a way that the resulting transcript will be efficiently translated. If the linkage of the promoter to the coding sequence is a transcriptional fusion and expression of the encoded protein is desired, the linkage is made so that the first translational initiation codon in the resulting transcript is the initiation codon of the coding sequence. Alternatively, if the linkage of the promoter to the coding sequence is a translational fusion and expression of the encoded protein is desired, the linkage is made so that the first translational initiation codon contained in the 5' untranslated sequence associated with the promoter and is linked such that the resulting translation product is in frame with the translational open reading frame that encodes the desired protein. Nucleic acid sequences that can be operably linked may be, for example, sequences that provide gene expression functions (i.e., gene expression elements such as promoters, 5' untranslated regions, introns, protein coding regions, 3' untranslated regions, polyadenylation sites, and/or transcriptional terminators), sequences that provide DNA transfer and/or integration functions, sequences that provide for selective functions (i.e., antibiotic resistance markers, biosynthetic genes), sequences that provide scoreable marker functions (i.e., reporter genes), sequences that facilitate in vitro or in vivo manipulations of the sequences (i.e., polylinker sequences, site specific recombination sequences) and sequences that provide replication functions (i.e., bacterial origins of replication, autonomous replication sequences, centromeric sequences).

"Operable insertion" as used herein, refers to the insertion of a sequence into a recombinant nucleic acid construct so that it is operably linked to at least one other sequence in such construct.

The term "vector", as used herein, refers to any recombinant polynucleotide construct that may be used to introduce heterologous DNA into a host cell.

As used herein, a "healthy reference subject" refers to a subject who is not afflicted with a disease or a condition. In certain embodiments, the "healthy reference subject" is a subject who is not afflicted with a disease, wherein the disease comprises Type 1 diabetes, Type 2 diabetes, insulin resistance, or hepatic steatosis. In certain embodiments, the "healthy reference subject" is a subject who is not afflicted with a condition, wherein the condition comprises: (a) blood glucose in excess of desired levels; (b) insulin levels in excess of desired levels; (c) hyperphagia; (d) consequential weight gain ; or (e) any condition in which a subject requires the increase of IGFBP-2 in the blood serum.

As used herein, an "untreated subject" refers to a subject that has either: i) not been administered Insulin-like Growth Factor-binding protein-2 (IGFBP-2); or ii) that has a blood serum IGFBP-2 protein concentration that has decreased to the blood serum IGFBP-2 protein concentration in the subject prior to administration of IGFBP-2.

Methods of Using IGFBP-2 to Treat Disease

It has been demonstrated that IGFBP-2 administration corrects hyperinsulinemia, hyperglycemia, hepatic steatosis and insulin resistance in a Type 2 diabetic mouse model. It has also been demonstrated that IGFBP-2 administration corrects severe hyperglycemia in a Type 1 diabetic mouse model. It has also been shown that IGFBP-2 administration lowers fasting blood sugar and serum insulin in normal healthy mice. Finally, IGFBP-2 prevents weight gain in treated leptin deficient ob mice suggesting that it also can act to prevent weight gain and that it also has efficacy for obesity.

Methods of Treating Type 1 Diabetes

In one aspect, methods of treating Type 1 diabetes by administering a therapeutically effective amount of an Insulin-like Growth Factor-binding protein-2 (IGFBP-2) to a subject in need thereof are provided. The subject in need thereof may be a mammal. In certain embodiments, the subject in need thereof is a human. One or more diagnostic test(s) can be conducted to identify a subject in need. Any biochemical and/or genetic test typically used to identify an individual suffering from Type 1 diabetes can be used. Examples of such diagnostic tests include, but are not limited to, a fasting plasma glucose test (FPG), an oral glucose tolerance test (OGTT), intraperitoneal injection with glucose, a measurement of serum insulin levels, and/or insulin tolerance test. According to the Center for Disease Control and Prevention, a human with a fasting blood glucose level of about 126 mg/dL or above is considered to have diabetes. (See, National Diabetes Fact Sheet, CDC, 2007). Other well established tests can then be used to determine if the individual with elevated fasting blood glucose levels is suffering from Type 1 diabetes, which is characterized by a deficiency in insulin.

Insulin-like Growth Factor-binding protein-2 (IGFBP-2) can be administered to the subject in any manner that provides a therapeutically effective dose of IGFBP-2. Administration methods include, but are not limited to, administration by oral, topical, rectal, percutaneous, by parenteral injection, intranasal, or inhalation routes. Also provided are administration of IGFBP-2 by any patch, solid formulation and/or device that would provide for the sustained release of a therapeutically effective dose of IGFBP-2 over time.

Therapeutically effective amounts administered comprise any amount that provides for a reduction in the severity of one or more symptoms associated with Type 1 diabetes. In certain embodiments, a therapeutically effective amount of IGFBP-2 administered comprises an amount that provides for an increase of at least about 2-fold to about 5-fold in a blood serum level of IGFBP-2 in said subject. Blood serum levels of IGFBP-2 can be determined by any technique that provides for a quantitative measure of IGFBP-2. Such techniques include, but are not limited to, ELISA or RIA assays. ELISA kits for determining human IGFBP-2 levels are commercially available (RayBiotech, Inc., Norcross, Ga., USA; Diagnostic Systems Laboratories Inc., Webster, Tex., USA). An RIA kit for determining IGFBP-2 levels is commercially available (Diagnostic Systems Laboratories Inc., Webster, Tex., USA). It is thus anticipated that the IGFBP-2 levels in the subject in need can be determined and that a dose that provides for a desired increase in blood serum IGFBP-2 levels can be administered. In certain embodiments where the subject is a human patient, a therapeutically effective amount of IGFBP-2 can comprise a post-administration target blood serum level range of about 1,000 ng/mL to about 2500 ng/mL (with about 500 ng/mL being the endogenous/normal amount). In certain embodiments, a therapeutically effective amount of IGFBP-2 can comprise a post-administration target blood serum level range of about 500 ng/mL to about 900 ng/mL (with 300 ng/mL being the endogenous/normal amount). It is anticipated that in certain embodiments, IGFBP-2 levels can fluctuate outside of this range either immediately after the administration of a dose, when levels of IGFBP-2 can exceed this range, or after dosing, when levels of IGFBP-2 can be below this range. Dosing regimens can be adjusted based on measurement of target IGFBP-2 levels and/or measurement of other indicia of therapeutic effectiveness that include, but are not limited to, measurements of blood glucose levels.

Measurement of blood glucose levels can be achieved by any reliable testing method and/or device. In certain embodiments, a therapeutically effective amount of IGFBP-2 can provide for a fasting blood serum glucose level of about 90 mg/dL to 105 mg/dL. In certain embodiments, a therapeutically effective amount of IGFBP-2 can provide for blood serum glucose levels of less than 300 mg/dL at 45 minutes post intraperitoneal administration of a glucose solution at a dose of about 1 unit of glucose/gram weight of said subject. A diagnostic test can be conducted to determine a therapeutically effective amount of IGFBP-2. Examples of such diagnostic tests include, but are not limited to, a fasting plasma glucose test (FPG), an oral glucose tolerance test (OGTT), and intraperitoneal injection with glucose followed by measurement of blood glucose levels.

Methods of Treating Type 2 Diabetes

Another aspect of the invention is a methods of treating Type 2 diabetes by administering a therapeutically effective amount of an Insulin-like Growth Factor-binding protein-2 (IGFBP-2) to a subject in need thereof are provided. The subject in need thereof may be a mammal. In certain embodiments, the subject in need thereof is a human. One or more diagnostic test(s) can be conducted to identify a subject in need. Any biochemical and/or genetic test typically used to identify an individual suffering from Type 2 diabetes can be used. Examples of such diagnostic tests include, but are not limited to, a fasting plasma glucose test (FPG), an oral glucose tolerance test (OGTT), intraperitoneal injection with glucose, a measurement of serum insulin levels, and/or insulin tolerance test. According to the Center For Disease Control and Prevention, a human with a fasting blood glucose level of about 126 mg/dL or above is considered to have diabetes. (See, National Diabetes Fact Sheet, CDC, 2007). Other well established tests can then be used to determine if the individual with elevated fasting blood glucose levels is suffering from Type 2 diabetes, which is characterized by a deficiency in cellular insulin action.

Insulin-like Growth Factor-binding protein-2 (IGFBP-2) can be administered to the subject in any manner that provides a therapeutically effective dose of IGFBP-2. Administration methods include, but are not limited to, administration by oral, topical, rectal, percutaneous, by parenteral injection, intranasal, or inhalation routes. Also provided are administration of IGFBP-2 by any patch, solid formulation and/or device that would provide for the sustained release of a therapeutically effective dose of IGFBP-2 over time.

Insulin-like Growth Factor-binding protein-2 (IGFBP-2) can be administered to the subject in any manner that provides a therapeutically effective dose of IGFBP-2. Administration methods include, but are not limited to, administration by oral, topical, rectal, percutaneous, by parenteral injection, intranasal, or inhalation routes. Also provided are administration of IGFBP-2 by any patch, solid formulation and/or device that would provide for the sustained release of a therapeutically effective dose of IGFBP-2 over time.

Therapeutically effective amounts administered comprise any amount that provides for a reduction in the severity of one or more symptoms associated with Type 2 diabetes. In certain embodiments, a therapeutically effective amount of IGFBP-2 administered comprises an amount that provides for an increase of at least about 2-fold to about 5-fold in a blood serum level of IGFBP-2 in said subject. Blood serum levels of IGFBP-2 can be determined by any technique that provides for a quantitative measure of IGFBP-2. Such techniques include, but are not limited to, ELISA or RIA assays. ELISA kits for determining human IGFBP-2 levels are commercially available (RayBiotech, Inc., Norcross, Ga., USA; Diagnostic Systems Laboratories Inc., Webster, Tex., USA). An RIA kit for determining IGFBP-2 levels is commercially available (Diagnostic Systems Laboratories Inc., Webster, Tex., USA). It is thus anticipated that the IGFBP-2 levels in the subject in need can be determined and that a dose that provides for a desired increase in blood serum IGFBP-2 levels can be administered. In certain embodiments where the subject is a human patient, a therapeutically effective amount of IGFBP-2 can comprise a post-administration target blood serum level range of about 1,000 ng/mL to about 2500 ng/mL (with about 500 ng/mL being the endogenous/normal amount). In certain embodiments, a therapeutically effective amount of IGFBP-2 can comprise a post-administration target blood serum level range of about 150 ng/mL to about 800 ng/mL. It is anticipated that in certain embodiments, IGFBP-2 levels can fluctuate outside of this range either immediately after the administration of a dose, when levels of IGFBP-2 can exceed this range, or after dosing, when levels of IGFBP-2 can be below this range. Dosing regimens can be adjusted based on measurement of target IGFBP-2 levels and/or measurement of other indicia of therapeutic effectiveness that include, but are not limited to, measurements of blood glucose levels.

Measurement of blood glucose levels can be achieved by any reliable testing method and/or device. In certain embodiments, a therapeutically effective amount of IGFBP-2 can provide for a fasting blood serum glucose level of about 80 mg/dL to 110 mg/dL. In certain embodiments, a therapeutically effective amount of IGFBP-2 can provide for blood serum glucose levels of less than 140 mg/dL at two hours post intraperitoneal administration of a glucose solution at a dose of about 1 unit of glucose/gram weight of said subject. A diagnostic test can be conducted to determine a therapeutically effective amount of IGFBP-2. Examples of such diagnostic tests include, but are not limited to, a fasting plasma glucose test (FPG), an oral glucose tolerance test (OGTT), and intraperitoneal injection with glucose followed by measurement of blood glucose levels.

Methods of Treating Insulin Resistance

Another aspect of the invention are methods of treating insulin resistance by administering a therapeutically effective amount of an Insulin-like Growth Factor-binding protein-2 (IGFBP-2) to a subject in need thereof are provided. The subject in need thereof may be a mammal. In certain embodiments, the subject in need thereof is a human. One or more diagnostic test(s) can be conducted to identify a subject in need. Any biochemical and/or genetic test typically used to identify an individual suffering from insulin resistance can be used. Examples of such diagnostic tests include, but are not limited to, a fasting plasma glucose test (FPG), an oral glucose tolerance test (OGTT), intraperitoneal injection with glucose, a measurement of serum insulin levels, and/or insulin tolerance test. Well established tests, such as an insulin tolerance test (ITT) can then be used to determine if the individual with elevated fasting blood glucose levels is suffering from insulin resistance, which is characterized by a inefficiency of the body to respond appropriately to insulin (by lowering blood glucose).

Insulin-like Growth Factor-binding protein-2 (IGFBP-2) can be administered to the subject in any manner that provides a therapeutically effective dose of IGFBP-2. Administration methods include, but are not limited to, administration by oral, topical, rectal, percutaneous, by parenteral injection, intranasal, or inhalation routes. Also provided are administration of IGFBP-2 by any patch, solid formulation and/or device that would provide for the sustained release of a therapeutically effective dose of IGFBP-2 over time.

Therapeutically effective amounts administered comprise any amount that provides for a reduction in the severity of one or more symptoms associated with insulin resistance. In certain embodiments, a therapeutically effective amount of IGFBP-2 administered comprises an amount that provides for an increase of at least about 2-fold to about 5-fold in a blood serum level of IGFBP-2 in said subject. Blood serum levels of IGFBP-2 can be determined by any technique that provides for a quantitative measure of IGFBP-2. Such techniques include, but are not limited to, ELISA or RIA assays. ELISA kits for determining human IGFBP-2 levels are commercially available (RayBiotech, Inc., Norcross, Ga., USA; Diagnostic Systems Laboratories Inc., Webster, Tex., USA). An RIA kit for determining IGFBP-2 levels is commercially available (Diagnostic Systems Laboratories Inc., Webster, Tex., USA). It is thus anticipated that the IGFBP-2 levels in the subject in need can be determined and that a dose that provides for a desired increase in blood serum IGFBP-2 levels can be administered. In certain embodiments where the subject is a human patient, a therapeutically effective amount of IGFBP-2 can comprise a post-administration target blood serum level range of about 1,000 ng/mL to about 2500 ng/mL (with about 500 ng/mL being the endogenous/normal amount). In certain embodiments, a therapeutically effective amount of IGFBP-2 can comprise a post-administration target blood serum level range of about 150 ng/mL to about 800 ng/mL. It is anticipated that in certain embodiments, IGFBP-2 levels can fluctuate outside of this range either immediately after the administration of a dose, when levels of IGFBP-2 can exceed this range, or after dosing, when levels of IGFBP-2 can be below this range. Dosing regimens can be adjusted based on measurement of target IGFBP-2 levels and/or measurement of other indicia of therapeutic effectiveness that include, but are not limited to, measurements of blood glucose levels.

Measurement of blood glucose levels can be achieved by any reliable testing method and/or device. In certain embodiments, a therapeutically effective amount of IGFBP-2 can provide for a fasting blood serum glucose level of about 80 mg/dL to 110 mg/dL. A therapeutically effective amount results in a fasting blood serum insulin level of about 10 ng/mL to about 1 ng/mL. In certain embodiments, a therapeutically effective amount of IGFBP-2 can provide for blood serum glucose levels of less than 140 mg/dL at two hours post intraperitoneal administration of a glucose solution at a dose of about 1 unit of glucose/gram weight of said subject. A diagnostic test can be conducted to determine a therapeutically effective amount of IGFBP-2. Examples of such diagnostic tests include, but are not limited to, a fasting plasma glucose test (FPG), an oral glucose tolerance test (OGTT), an insulin tolerance test (ITT) and intraperitoneal injection with glucose followed by measurement of blood glucose levels.

Method for Treating Hepatic Steatosis

Another aspect of the method is of treating hepatic steatosis by administering a therapeutically effective amount of Insulin-like Growth Factor-binding protein-2 to a subject in need thereof to reduce hepatic steatosis. Hepatic steatosis is characterized by excessive amounts of triglycerides and other fats inside liver cells. Hepatic steatosis may be assessed, for example, by pathology or when fat in the liver exceeds 5-10% by weight. The subject in need thereof may be a mammal. In certain embodiments, the subject in need thereof is a human. One or more diagnostic test(s) can be conducted to identify a subject in need. Any clinical test typically used to identify an individual suffering from hepatic steatosis can be used.

Insulin-like Growth Factor-binding protein-2 (IGFBP-2) can be administered to the subject in any manner that provides a therapeutically effective dose of IGFBP-2. Administration methods include, but are not limited to, administration by oral, topical, rectal, percutaneous, by parenteral injection, intranasal, or inhalation routes. Also provided are administration of IGFBP-2 by any patch, solid formulation and/or device that would provide for the sustained release of a therapeutically effective dose of IGFBP-2 over time.

Therapeutically effective amounts administered comprise any amount that provides for a reduction in the severity of one or more symptoms associated with hepatic steatosis. In certain embodiments, a therapeutically effective amount of IGFBP-2 administered comprises an amount that provides for an increase of at least about 2-fold to about 5-fold in a blood serum level of IGFBP-2 in said subject. Blood serum levels of IGFBP-2 can be determined by any technique that provides for a quantitative measure of IGFBP-2. Such techniques include, but are not limited to, ELISA or RIA assays. ELISA kits for determining human IGFBP-2 levels is commercially available (RayBiotech, Inc., Norcross, Ga., USA; Diagnostic Systems Laboratories Inc., Webster, Tex., USA). An RIA kit for determining IGFBP-2 levels is commercially available (Diagnostic Systems Laboratories Inc., Webster, Tex., USA). It is thus anticipated that the IGFBP-2 levels in the subject in need can be determined and that a dose that provides for a the desired increase in blood serum IGFBP-2 levels can be administered. In certain embodiments where the subject is a human patient, a therapeutically effective amount of IGFBP-2 can comprise a post-administration target blood serum level range of about 1,000 ng/mL to about 2500 ng/mL (with about 500 ng/mL being the endogenous/normal amount). In certain embodiments, a therapeutically effective amount of IGFBP-2 can comprise a post-administration target blood serum level range of about 30 ng/mL to about 800 ng/mL. It is anticipated that in certain embodiments, IGFBP-2 levels can fluctuate outside of this range either immediately after the administration of a dose, when levels of IGFBP-2 can exceed this range, or after dosing, when levels of IGFBP-2 can be below this range. Dosing regimens can be adjusted based on measurement of target IGFBP-2 levels and/or measurement of other indicia of therapeutic effectiveness.

Methods of Lowering Blood Glucose and Serum Insulin

Another aspect of the invention is to lower blood sugar and/or serum insulin in a patient in need of such a treatment. Patients in need of such treatment include, but are not limited, to individuals suffering from hyperglycemia and/or hyperinsulinemia. The subject in need thereof may be a mammal. In certain embodiments, the subject in need thereof is a human. Insulin-like Growth Factor-binding protein-2 (IGFBP-2) can be administered to the subject in any manner that provides a therapeutically effective dose of IGFBP-2. Administration methods include, but are not limited to, administration by oral, topical, rectal, percutaneous, by parenteral injection, intranasal, or inhalation routes. Also provided are administration of IGFBP-2 by any patch, solid formulation and/or device that would provide for the sustained release of a therapeutically effective dose of IGFBP-2 over time.

Therapeutically effective amounts administered comprise any amount that provides for a reduction in the severity of one or more symptoms associated with increased blood glucose (hyperglycemia) and/or increased insulin levels (hyperinsulinemia). In certain embodiments, a therapeutically effective amount of IGFBP-2 administered comprises an amount that provides for an increase of at least about 2-fold to about 5-fold in a blood serum level of IGFBP-2 in said subject. Blood serum levels of IGFBP-2 can be determined by any technique that provides for a quantitative measure of IGFBP-2. Such techniques include, but are not limited to, ELISA or RIA assays. ELISA kits for determining human IGFBP-2 levels are commercially available (RayBiotech, Inc., Norcross, Ga., USA; Diagnostic Systems Laboratories Inc., Webster, Tex., USA). An RIA kit for determining IGFBP-2 levels is commercially available (Diagnostic Systems Laboratories Inc., Webster, Tex., USA). It is thus anticipated that the IGFBP-2 levels in the subject in need can be determined and that a dose that provides for a desired increase in blood serum IGFBP-2 levels can be administered. In certain embodiments where the subject is a human patient, a therapeutically effective amount of IGFBP-2 can comprise a post-administration target blood serum level range of about 1,000 ng/mL to about 2500 ng/mL (with about 500 ng/mL being the endogenous/normal amount). In certain embodiments, a therapeutically effective amount of Insulin-like Growth Factor-binding protein-2 comprises a blood serum level of about 600 ng/mL to about 800 ng/mL (when untreated controls—wt—has a native blood serum level of 250-350 ng.mL ng/mL). In certain embodiments, the therapeutically effective amount provides for a blood glucose level of about 80 mg/dL to 90 mg/dL (with untreated controls having blood glucose of 110-120 mg/dL). In certain embodiments, the therapeutically effective amount provides for a fasting blood serum insulin level of about 0.01 ng/mL to 0.05 ng/mL (with untreated controls having blood insulin of 0.15-0.25 ng/mL).

It is anticipated that in certain embodiments, IGFBP-2 levels can fluctuate outside of this range either immediately after the administration of a dose, when levels of IGFBP-2 can exceed this range, or after dosing, when levels of IGFBP-2 can be below this range. Dosing regimens can be adjusted based on measurement of target IGFBP-2 levels and/or measurement of other indicia of therapeutic effectiveness that include, but are not limited to, measurements of blood glucose levels and serum insulin levels.

Measurement of blood glucose levels can be achieved by any reliable testing method and/or device. In certain embodiments, a therapeutically effective amount of IGFBP-2 can provide for a fasting blood serum glucose level of about 80 mg/dL. In certain embodiments, a therapeutically effective amount of IGFBP-2 can provide for blood serum glucose levels of less than 80 mg/dL at 2 hours post-intraperitoneal administration of a glucose solution at a dose of about 1 unit of glucose/gram weight of said subject. A diagnostic test can be conducted to determine a therapeutically effective amount of IGFBP-2. Examples of such diagnostic tests include, but are not limited to, a fasting plasma glucose test (FPG), an oral glucose tolerance test (OGTT), and intraperitoneal injection with glucose followed by measurement of blood glucose levels.

Methods of Administration of IGFBP-2 Treatments

In practicing any of the above referenced methods involving administration of IGFBP-2 treatment agents to a subject, it is contemplated that a variety of pharmaceutical or veterinary compositions comprising these active agents can be administered by a variety of techniques. Such pharmaceutical or veterinary compositions may be formulated in various ways known in the art for administration purposes. To prepare the pharmaceutical or veterinary IGFBP-2 compositions, an effective amount of the IGFBP-2 as the active ingredient is combined with one or more pharmaceutically acceptable carriers and delivery vehicles. Numerous pharmaceutically acceptable carriers and delivery vehicles exist that are readily accessible and well known in the art, which may be employed to generate the preparation desired (i.e., that permit administration of the pharmaceutical composition orally, topically, rectally, percutaneously, by parenteral injection, intranasally or by inhalation). Representative examples of pharmaceutically acceptable carriers and delivery vehicles include aluminum stearate, lecithin, serum proteins, such as human serum albumin; buffer substances such as the various phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, and zinc salts, colloidal silica, magnesium trisilicate, polyvinyl pyrrolidone, cellulose-based substances, polyethylene glycol, sodium carboxymethylcellulose, polyacrylates, waxes, polyethylene, polyoxypropylene-block polymers, polyethylene glycol and wool fat, and the like. The pharmacologic compositions described herein may further be prepared in unitary dosage form suitable for administration orally, percutaneously, by parenteral injection (including subcutaneous, intramuscular, intravenous and intradermal), topically, intranasally, by inhalation, or for application to a medical device, such as an implant, catheter, or other device. In preparing the compositions that permit administration of an oral dosage, for example, any of the pharmaceutically acceptable carriers known in the art may be used, such as water, glycols, oils, alcohols and the like in the case of carriers that permit oral delivery of liquid preparations such as suspensions, syrups, elixirs and solutions. When solid pharmaceutically acceptable carriers are desired that permit oral or rectal administration, starches, sugars, kaolin, lubricants, binders, cellulose and its derivatives, and disintegrating agents and the like may be used to prepare, for example, powders, pills, capsules and tablets. For pharmaceutically acceptable carriers that permit parenteral administration, the pharmaceutically acceptable carriers often comprise sterile water, which may be supplemented with various solutes to, for example, increase solubility. Injectable solutions may be prepared in which the pharmaceutically acceptable carrier comprises saline solution, glucose solution, or a mixture thereof, which may include certain well-known anti-oxidants, buffers, bacteriostats, and other solutes that render the formulation isotonic with the blood of the intended patient.

Kits

The invention also contemplates kits. In one aspect, a kit for the use in treating Type 1 diabetes has a therapeutically effective amount of Insulin-like Growth Factor-binding protein-2; and (i) one or more pharmaceutically acceptable carriers; one or more containers for said pharmaceutical composition; and instructions for the use thereof in treating Type 1 diabetes. The instructions of the kits may describe how to use the Insulin-like Growth Factor-binding protein-2 and/or one or more pharmaceutically acceptable carriers contained within the kit. The instructions may be provided, for example, within the packaging of the kit, on the packaging, and on a website.

In another aspect, a kit for the use in treating Type 2 diabetes has a pharmaceutical composition comprising (i) a recombinant nucleic acid vector containing a nucleic acid sequence encoding Insulin-like Growth Factor-binding protein-2 operably linked to a heterologous expression control sequence or a therapeutically effective amount of Insulin-like Growth Factor-binding protein-2; one or more containers for said pharmaceutical composition; and instructions for the use thereof in treating Type 2 diabetes. The instructions of the kits may describe how to use the recombinant nucleic acid vector containing a nucleic acid sequence encoding Insulin-like Growth Factor-binding protein-2 operably linked to a heterologous expression control sequence or a therapeutically effective amount of Insulin-like Growth Factor-binding protein-2 contained within the kit. The instructions may be provided, for example, within the packaging of the kit, on the packaging, and on a website.

In a further aspect, a kit for the use in treating insulin resistance has a pharmaceutical composition comprising (i) a recombinant nucleic acid vector containing a nucleic acid sequence encoding Insulin-like Growth Factor-binding protein-2 operably linked to a heterologous expression control sequence or a therapeutically effective amount of Insulin-like Growth Factor-binding protein-2; one or more containers for said pharmaceutical composition; and instructions for the use thereof in treating insulin resistance. The instructions of the kits may describe how to use the recombinant nucleic acid vector containing a nucleic acid sequence encoding Insulin-like Growth Factor-binding protein-2 operably linked to a heterologous expression control sequence or a therapeutically effective amount of Insulin-like Growth Factor-binding protein-2 contained within the kit. The instructions may be provided, for example, within the packaging of the kit, on the packaging, and on a website.

In a further aspect, a kit for the use in treating hepatic steatosis has a pharmaceutical composition comprising (i) a recombinant nucleic acid vector containing a nucleic acid sequence encoding Insulin-like Growth Factor-binding protein-2 operably linked to a heterologous expression control sequence or a therapeutically effective amount of Insulin-like Growth Factor-binding protein-2; one or more containers for said pharmaceutical composition; and instructions for the use thereof in hepatic steatosis. The instructions of the kits may describe how to use the recombinant nucleic acid vector containing a nucleic acid sequence encoding Insulin-like Growth Factor-binding protein-2 operably linked to a heterologous expression control sequence or a therapeutically effective amount of Insulin-like Growth Factor-binding protein-2 contained within the kit. The instructions may be provided, for example, within the packaging of the kit, on the packaging, and on a website.

In a further aspect, a kit for the use in lowering blood glucose levels has a pharmaceutical composition comprising (i) a recombinant nucleic acid vector containing a nucleic acid sequence encoding Insulin-like Growth Factor-binding protein-2 operably linked to a heterologous expression control sequence or a therapeutically effective amount of Insulin-like Growth Factor-binding protein-2; one or more containers for said pharmaceutical composition; and instructions for the use thereof in lowering blood glucose levels. The instructions of the kits may describe how to use the recombinant nucleic acid vector containing a nucleic acid sequence encoding Insulin-like Growth Factor-binding protein-2 operably linked to a heterologous expression control sequence or a therapeutically effective amount of Insulin-like Growth Factor-binding protein-2 contained within the kit. The instructions may be provided, for example, within the packaging of the kit, on the packaging, and on a website.

In a further aspect, a kit for the use in lowering serum insulin levels has a pharmaceutical composition comprising (i) a recombinant nucleic acid vector containing a nucleic acid sequence encoding Insulin-like Growth Factor-binding protein-2 operably linked to a heterologous expression control sequence or a therapeutically effective amount of Insulin-like Growth Factor-binding protein-2; one or more containers for said pharmaceutical composition; and instructions for the use thereof in lowering serum insulin levels. The instructions of the kits may describe how to use the recombinant nucleic acid vector containing a nucleic acid sequence encoding Insulin-like Growth Factor-binding protein-2 operably linked to a heterologous expression control sequence or a therapeutically effective amount of Insulin-like Growth Factor-binding protein-2 contained within the kit. The instructions may be provided, for example, within the packaging of the kit, on the packaging, and on a website.

In a further aspect, a kit for the use in treating hyperphagia and consequential weight gain has a pharmaceutical composition comprising (i) a recombinant nucleic acid vector containing a nucleic acid sequence encoding Insulin-like Growth Factor-binding protein-2 operably linked to a heterologous expression control sequence or a therapeutically effective amount of Insulin-like Growth Factor-binding protein-2; one or more containers for said pharmaceutical composition; and instructions for the use thereof in treating hyperphagia and consequential weight. The instructions of the kits may describe how to use the recombinant nucleic acid vector containing a nucleic acid sequence encoding Insulin-like Growth Factor-binding protein-2 operably linked to a heterologous expression control sequence or a therapeutically effective amount of Insulin-like Growth Factor-binding protein-2 contained within the kit. The instructions may be provided, for example, within the packaging of the kit, on the packaging, and on a website.

Methods of Treating Hyperphagia and Consequential Weight-Gain

Methods of treating hyperphagia and consequential weight gain by administering a therapeutically effective amount of an Insulin-like Growth Factor-binding protein-2 (IGFBP-2) to a subject in need thereof are also provided herein. The subject in need thereof may be a mammal. In certain embodiments, the subject in need thereof is a human. One or more diagnostic test(s) can be conducted to identify a subject in need. Any clinical test typically used to identify an individual suffering from hyperphagia can be used. Examples of such diagnostic tests include, but are not limited to, journal to record daily food intake and daily caloric intake.

Insulin-like Growth Factor-binding protein-2 (IGFBP-2) can be administered to the subject in any manner that provides a therapeutically effective dose of IGFBP-2. Administration methods include, but are not limited to, administration by oral, topical, rectal, percutaneous, by parenteral injection, intranasal, or inhalation routes. Also provided are administration of IGFBP-2 by any patch, solid formulation and/or device that would provide for the sustained release of a therapeutically effective dose of IGFBP-2 over time.

In certain embodiments, a therapeutically effective amount of IGFBP-2 can comprise a post-administration target blood serum level range of about 150 ng/mL to about 800 ng/mL. It is anticipated that in certain embodiments, IGFBP-2 levels can fluctuate outside of this range either immediately after the administration of a dose, when levels of IGFBP-2 can exceed this range, or after dosing, when levels of IGFBP-2 can be below this range. Dosing regimens can be adjusted based on measurement of target IGFBP-2 levels and/or measurement of other indicia of therapeutic effectiveness that include, but are not limited to, measurements food intake and weight gain.

In certain embodiments, a therapeutically effective amount of IGFBP-2 can provide up to a 40% reduction in food intake. Reductions in food intake attained by administration of a therapeutically effective amount of IGFBP-2 can range from about 5%, 10%, 20% or 30% to about 40%. In certain embodiments, a therapeutically effective amount of IGFBP-2 can provide a decrease or a halt in weight gain due to reduction in food intake. In certain embodiments, decreases in weight gain attained by administration of a therapeutically effective amount of IGFBP-2 can range from about 10%, 20%, 40%, 60%, or 80% to about 100%, where a 100% decrease represents a halt in weight gain. In certain embodiments, decreases in weight gain attained by administration of a therapeutically effective amount of IGFBP-2 can range from about 10% to about 40%, 60%, 80%, or 100%, where a 100% decrease represents a halt in weight gain.

IGFBP-2 Proteins and Methods of Producing IGFBP-2

As used herein, the term IGFBP-2 protein encompasses any biologically active form of IGFBP-2. In certain embodiments, the IGFBP-2 protein would have biological activity that is equivalent to that of the naturally occurring form of the mature IGFBP-2 protein wherein the signal peptide has been removed from the N-terminus of the IGFBP-2 proprotein. In most instances, the IGFBP-2 used to treat a subject would be a mature form of IGFBP-2 that is derived from the same species as the subject. For treatment of humans, the IGFBP-2 protein used include, but are not limited to, the naturally occurring mature form of the human protein shown as SEQ ID NOs: 2, 4, 6, 8, 10, 12, 14, 16, 18, 20, 22, 24, 26, or 28. In certain embodiments, the respective, IGFBP-2 proprotein of SEQ ID NOs: 1, 3, 5, 7, 9, 11, 13, 15, 17, 19, 21, 23 25, or 27 can be expressed in cells to yield the corresponding mature IGFBP-2 protein. Other human IGFBP-2 proprotein variants that can be used to obtain mature IGFBP-2 protein to treat humans include, but are not limited to, SEQ ID NO. 29, or forms of SEQ ID NO:29 wherein Xaa at position 137 is substituted with aspartic acid or alanine, wherein Xaa at position 139 is substituted with aspartic acid or tyrosine, wherein Xaa at position 323 is substituted with tryptophan or arginine, and/or any combination of the aforementioned variants at positions 137, 139, and 323. Other mature human IGFBP-2 proprotein variants that can be used to treat humans include, but are not limited to, SEQ ID NO. 30, or forms of SEQ ID NO:30 wherein Xaa at position 98 is substituted with aspartic acid or alanine, wherein Xaa at position 100 is substituted with aspartic acid or tyrosine, wherein Xaa at position 284 is substituted with tryptophan or arginine, and/or any combination of the aforementioned variants at positions 98, 100, and 284. In certain embodiments, any one of the human IGFBP-2 amino acid sequences provided herein in the sequence listing may be used to produce recombinant IGFBP-2 for use in the above treatment methods and kits. It is also anticipated that additional naturally occurring amino acid variants of the human IGFBP-2 protein that are biologically active and that are uncovered in sequencing of human IGFBP-2 genes derived from individuals whose sequences become known in the future. Biological activity of the IGFBP-2 protein can be determined by its ability to inhibit IGF-I or IGF-II induced proliferation of cells. Such inhibition of IGF-I or IGF-II induced proliferation can be assayed in cells including, but not limited to, FDC-P1 cells.

Also provided are vectors comprising a nucleic acid sequence encoding IGFBP-2 to express recombinant IGFBP-2. In specific embodiments, the vectors comprise an operably linked nucleotide sequence which regulates the expression of IGFBP-2. For example, the nucleotide sequence encoding IGFBP-2 can be operably linked to an inducible or constitutive promoter. Transcriptional termination and/or polyadenylation sites can also be operably linked to the IGFBP-2 gene.

Host cells comprising the nucleic acids and vectors are also provided. In certain embodiments, the vector or nucleic acid is integrated into the host cell genome; in other embodiments, the vector or nucleic acid is extra-chromosomal. A host cell can be a mammalian cell, a yeast cell, and insect cell or a bacterial cell. The bacterial host cell can be an *E. coli* cell.

In considering all of the various host systems for expression of IGFBP-2 proteins, it is appreciated that host-appropriate systems that provide for either intracellular or extracellular expression of the IGFBP-2 proteins can be used. In vectors for extracellular expression, the mature form of IGFBP-2 can be fused at its it's N-terminus to an appropriate signal peptide. N-terminal deletion mutants of IGFBP-2 or the mature IGFBP-2 protein can also be N-terminally fused to other proteins or peptide sequences that provide for other desired characteristics including, but not limited to, improved stability, affinity purification, improved pharmacokinetic properties, and/or improved delivery to a target organ. In certain embodiments, N-terminal fusions to the mature IGFBP-2 protein are operably linked by a protease recognition site that can facilitate removal of the N-terminal fusion protein or peptide either in vivo or in vitro.

In considering all of the various host systems for expression of IGFBP protein, it is also appreciated that host-appropriate systems that provide for extracellular expression of the IGFBP-2 proteins can be used. In such vectors, secretion signal sequences that provide for secretion of IGFBP-2 proteins in the desired host cell are operably linked to the N-terminus of the mature IGFBP-2 protein. Mammalian secretion signals include, but are not limited to, a tPA signal peptide, a mammalian alkaline phosphatase signal peptide and the like. Yeast secretion signals include, but are not limited to, a yeast alpha mating type signal peptide, a yeast invertase signal peptide, or yeast alkaline phosphatase signal peptide and the like. Insect cell secretion signals include, but are not limited to, an egt signal peptide, a p67 signal peptide, or other signal peptides useful for expression of heterologous proteins as disclosed in U.S. Pat. No. 5,516,657.

The recombinant expression vectors comprise nucleotide sequence encoding an IGFBP-2 protein in a form suitable for expression in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers, ribosome binding sites, transcriptional terminators, and other expression control elements (e.g., polyadenylation signals). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of IGFBP-2 protein desired, etc. The expression vectors can be introduced into host cells to thereby produce IGFBP-2 proteins encoded by nucleic acids as described herein.

The recombinant expression vectors can be designed for expression of an IGFBP-2 protein in prokaryotic (e.g., *E. coli*), Of eukaryotic cells (e.g., insect cells (using baculovirus expression vectors)), yeast cells, or mammalian cells. Alternatively, the recombinant expression vector can be transcribed and translated in vitro, for example using T7 promoter regulatory sequences and T7 polymerase and an in vitro translation system.

Expression of IGFBP-2 proteins in prokaryotes can be carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of the recombinant IGFBP-2 protein; 2) to increase the solubility of the recombinant IGFBP-2 protein; and 3) to aid in the purification of the recombinant IGFBP-2 protein by acting as a ligand in affinity purification. Often, in fusion expression vectors, a proteolytic cleavage domain is introduced at the junction of the fusion moiety and the recombinant protein to enable separation of the recombinant protein from the fusion moiety subsequent to purification of the fusion protein. Thus, the fusion moiety and proteolytic cleavage domain together can act as an activation sequence, including a protease recognition site, for recombinant expression of an IGFBP-2 protein. Such enzymes, and their cognate recognition sequences, include Factor Xa, thrombin, rhinovirus 3C protease and enterokinase. Typical fusion expression vectors include pGEX (Pharmacia Biotech Inc; Smith and Johnson (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. N-terminal fusions of a "Hisx6" tag to the N-terminus of IGFBP-2 protein can provide for efficient purification of IGFBP-2 protein via NI-NTI chromatography. Illustrative examples of vectors that provide for N-terminal Hisx6 fusions include, but are not limited to, pET28 vectors (Novagen, Inc., Madison, Wis., USA) and modifications thereof. The pET vector system and appropriate host cells are described in (Studier et al., Gene Expression Technology: Methods in Enzymology 185, Academic Press, San Diego, Calif. (1990) 60-89).

Examples of suitable inducible non-fusion *E. coli* expression vectors include pTrc (Amann et al., (1988) Gene 69:301-315) and pET 11d (Studier et al., Gene Expression Technology: Methods in Enzymology 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS174(DE3) from a resident λ prophage harboring a T7 gn1 gene under the transcriptional control of the lacUV 5 promoter.

One strategy to maximize recombinant IGFBP-2 protein expression in *E. coli* is to express the protein in a host bacteria with an impaired capacity to proteolytically cleave the recombinant protein (Gottesman, Gene Expression Technology: Methods in Enzymology 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al., (1992) Nucleic Acids Res. 20:2111-2118). Such alteration of nucleic acid sequences of IGFBP-2 can be carried out by standard DNA synthesis techniques.

In another embodiment, the expression vector is a yeast expression vector. Examples of vectors for expression in yeast *S. cerevisiae* or *P. pastoris* include pYepSec1 (Baldari et al., (1987) EMBO J. 6:229-234), pMFa (Kurjan and Herskowitz, (1982) Cell 30:933-943), pJRY88 (Schultz et al., (1987) Gene 54:113-123), pYES2 (Invitrogen Corporation, San Diego, Calif.), and pPicZ (Invitrogen Corp, San Diego, Calif.). For expression in *Pichia*, a methanol-inducible promoter is preferably used. Alteration of the nucleic acid sequence of the nucleic acid to be inserted into an expression vector so that the individual codons for each amino acid are those preferentially utilized in yeast is also contemplated herein.

Alternatively, the expression vector is a baculovirus expression vector. Baculovirus vectors available for expression of proteins in cultured insect cells (e.g., Sf9 cells) include the pAc series (Smith et al. (1983) Mol. Cell Biol. 3:2156-2165) and the pVL series (Luckow and Summers (1989) Virology 170:31-39). Another strategy is to alter the nucleic acid sequence of IGFBP-2 to be inserted into an expression vector so that the individual codons for each amino acid are those preferentially utilized in insect cells. Recombinant IGFBP-2 protein produced in insect cells is commercially available from SBH Sciences, Natick, Mass., USA.

An IGFBP-2 protein can be expressed in mammalian cells using a mammalian expression vector. Examples of mammalian expression vectors include pCDM8 (Seed (1987) Nature 329:840) and pMT2PC (Kaufman et al., (1987) EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra. Recombinant murine IGFBP-2 protein is also commercially available (R & D Systems, Inc. Minneapolis, Minn. Catalog number 797-B2).

In preparing IGFBP-2 for administration to subjects, it is contemplated that the protein can be covalently modified with poly(ethylene glycol) (PEG). Covalently coupling cysteine-reactive poly(ethylene glycol) (20 kDa) to IGFBP-1 reportedly resulted in a prolonged serum half-life of 13.6 hours (Van den Berg, C. L., et al. 33 Europ. J. Cancer 1108-1113 (1997) and WO 94/22466). According to the applicants in WO 94/22466, it is believed that amino acids in the middle domain of IGFBP-1 can be substituted by cysteine for specific PEGylation without interference with the IGF binding and inhibitory activity of that protein. PEGylated IGFBP-4 is reported to have superior properties in regard to therapeutic applicability in tumor treatment such as suppressing tumor growth, angiogenesis and/or metastasis in vivo and also avoids undesired side effects in vivo such as alteration of normal kidney cells found for lower weight PEGylated IGFBP-4 (EP1545623).

In certain embodiments, polyethylene glycol) activated with amino-reactive reagents can be used to PEGylate IGFBP-2. Poly(ethylene glycol) can be attached to IGFBP-2 at the N-terminal α-amino group and the ε-amino groups of lysine residues. Amino-reactive reagents for PEGylation of proteins include, but are not limited to, N-hydroxysuccinimide (NHS). When the PEG groups are conjugated to IGFBP-2 by primary amino group(s) (amino-reactive PEGylation), the IGFBP-2-PEG conjugate can be a monoPEG-IGFBP-2 conjugate. Also contemplated are branched PEG-IGFBP-2 conjugates.

It is further contemplated that PEG groups may be attached to IGFBP-2 by thiol-reactive PEGylation as disclosed in European Patent No. 1545623 and reviewed in Veronese, 22 Biomaterials 405-417 (2001)). Conjugation of PEG to thiol groups can be performed using thiol-activated PEGs. Thiol-activated PEGs include, but are not limited to, PEG-orthopyridyl-disulfide, PEG-maleimide, PEG-vinylsulfone, and PEG-iodoacetamide.

EXAMPLES

The following examples describe embodiments of the invention. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

Example 1

Animals, Diet, Treatments, Experimental Procedures

IGFBP-2 Treatment

Eight week old male C57B16 Lep-ob or wild type mice were acclimated to our animal facility. C57B16 Lep-ob or C57B16 wild type—with or without STZ treatment (see below) were injected intrajugularly under anesthesia (isoflourane) with $1.2 \times 10^{11}$ particles of Ad-CMV-empty, Ad-CMV-Luciferase, or Ad-CMV-IGFBP-2 (ViraQuest Inc., North Liberty, Iowa). One week after injections, serum levels of IGFBP-2 were determined with an IGFBP-2 EIA kit (Alpco Diagnostics, Windham, N.H.).

Streptomycin-Treated Animals

To prepare hypo-insulinemic mice, 4 week old male C57B16 wild type animals (Jackson Laboratory, Bar Harbor, Me.) were intraperitoneally dosed with 50 mg/kg Streptozocin (Sigma-Aldrich, St Louis, Mo.) daily for 5 days to ablate pancreatic beta cells. After four weeks, hyperglycemic animals were injected with Ad-CMV-IGFBP-2 as described above.

Glucose Tolerance Test

Glucose tolerance tests were performed by intraperitoneally injecting mice with 1 unit of glucose per gram body weight. Blood glucose was measured at 0, 30, 60, and 120 minutes post-injection. In the case of STZ animals, blood glucose was taken at 0 and 45 minutes post-injection.

Insulin Tolerance Test

Insulin tolerance tests were performed by intraperitoneally injecting mice with 1 U/kg (wild type or STZ) or 2 U/kg (ob/ob) of human insulin (Humulin™, Eli Lilly and Company, Indianapolis, Ind.) in sterile phosphate buffered saline. Blood glucose was measured at 0, 15, 30, 60, 120 and 180 minutes post-injection.

Serum Assays

Blood glucose was determined using an Ascensia Elite XL glucometer (Bayer). In the case of STZ animals, blood glucose was sometimes "out of range" for the Ascensia Elite XL glucosmeter and hence a Bioassay Systems QuantiChrom Glucose Assay Kit was used to determine blood glucose. For all other assays, animals were bled intraorbitally under anesthesia (isoflourane). Blood was centrifuged for 10 minutes and serum was collected. Serum insulin, serum leptin, and serum IGFBP-2 were determined using an Insulin (mouse), Leptin (mouse/rat), and IGFBP-2 (mouse/rat) EIA kits, respectively (Alpco Diagnostics, Windham, N.H.).

Example 2

IGFBP-2 Treatment Corrects Blood Glucose Levels in Type 2 Diabetic ob/ob Mice

Figure 2:
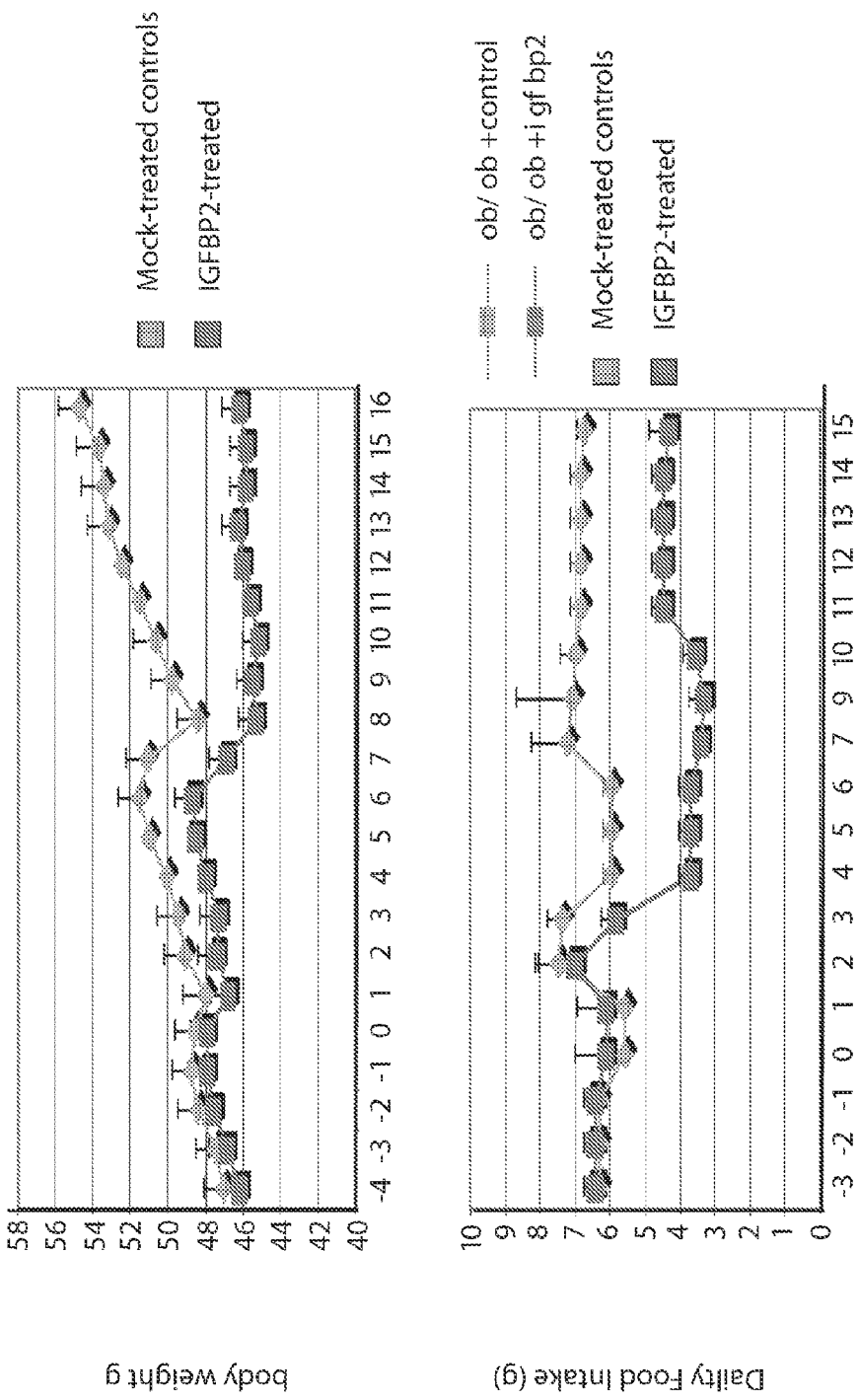
FIG. 2 is a graph showing body weight and daily food intake in ob/ob mice treated with IGFBP-2.

To determine whether IGFBP-2 affected blood glucose and insulin levels, ob/ob animals were injected intrajugularly with Ad-CMV-IGFBP-2, Ad-CMV-empty, or Ad-CMV-luciferase virus. After 5 days, Ad-CMV-luciferase animals were assayed for hepatic expression of luciferase and Ad-CMV-IGFBP-2 and Ad-CMV-empty animals were assayed for serum IGFBP-2 levels to confirm secretion of IGFBP-2 into the blood stream. Results indicated both robust expression and secretion of IGFBP-2. Daily weight and food intake was recorded and blood glucose and insulin was assayed. One week post-injection, IGFBP-2 treated ob/ob animals showed a drop in both blood glucose and serum insulin. As shown in FIG. 1, blood glucose of IGFBP-2 treated animals was less than 100 mg/dL, whereas blood glucose levels of control animals exceeded 300 mg/dL. Serum insulin levels improved from hyperinsulinemic 85 ng/mL to under 5 ng/mL (FIG. 1). Weight gain leveled off in IGFBP-2 treated animals and also exhibited a modest decrease in food intake compared to control animals (FIG. 2). The lack of weight gain could not account for the complete corrections in hyperglycemia and hyperinsulinemia as a pair-feeding at this food-intake-level does not significantly affect diabetic symptoms.

Example 3

Glucose Tolerance In IGFBP-2 Treated ob/ob Type 2 Diabetic Mice

Figure 3:
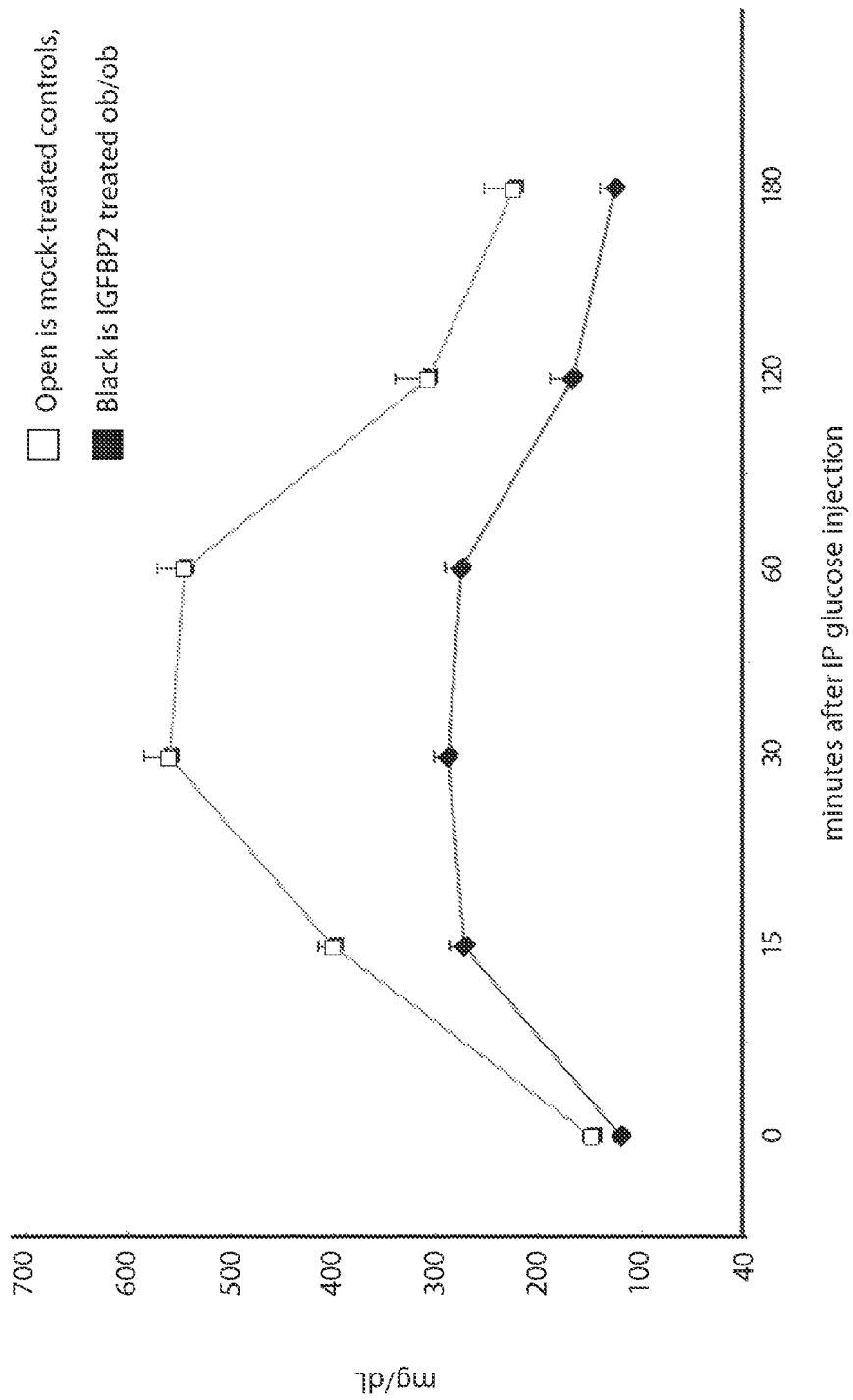
FIG. 3 is a graph showing the results of a Glucose Tolerance Test in ob/ob mice treated with IGFBP-2. The data points on the line showing higher glucose levels are from mock treated controls and the data points on the line showing lower glucose levels are from IGFBP-2 treated ob/ob mice.

Glucose tolerance was assayed in IGFBP-2 treated and control ob/ob mice after an overnight fast. Control animals blood glucose exceeded 500 mg/dL at 30 minutes. Blood glucose of IGFBP-2 treated animals, however, remained below 300 mg/dL (FIG. 3). This means that IGFBP-2 treated animals are more insulin sensitive. Despite having lower insulin levels (see example 5), the low insulin levels are more effective in regulating serum glucose.

Example 4

IGFBP-2 Treated Wild Type Mice

Figure 4:
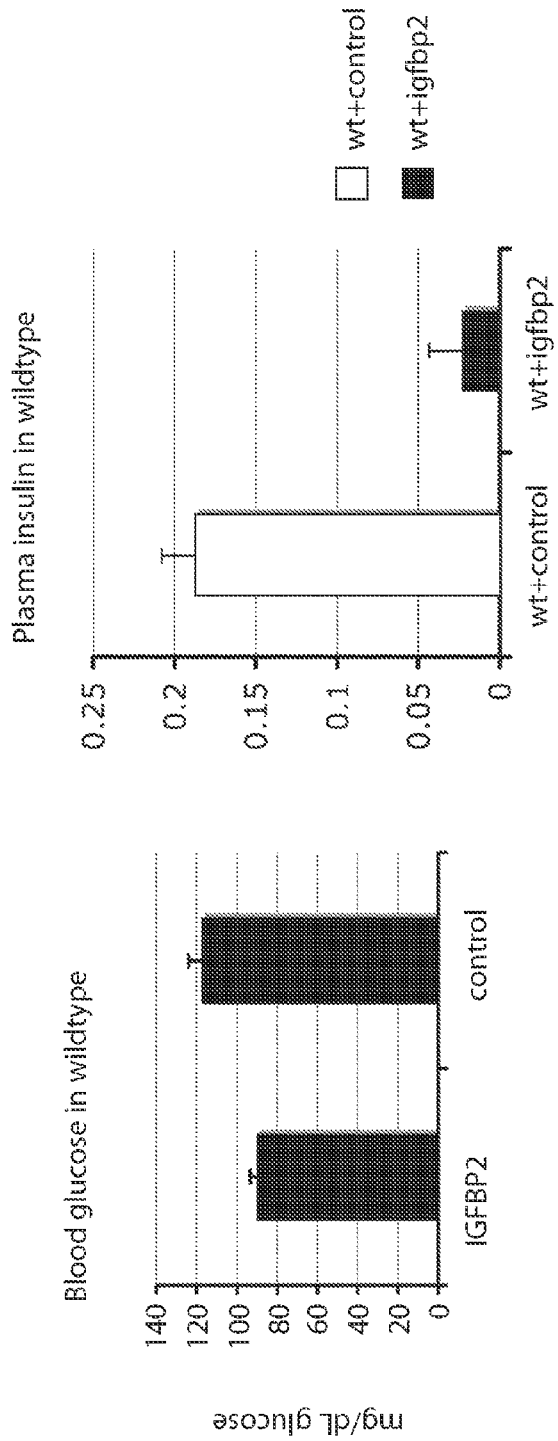
FIG. 4 is a graph showing serum glucose and insulin in wild type (non-diabetic) animals after treatment with IGFBP-2.

To study the effect of IGFBP-2 treatment in a wild type mouse, we repeated the above experiments in wild type C57B16 males (FIG. 4). When IGFBP-2 serum levels soared to 700+/−100 ng/mL in treated animals compared to mock treated (300+/−50 ng/mL), blood glucose dropped from 110-120 mg/dL to 80-90 mg/dL and serum insulin dropped to 0.01 ng/mL to 0.05 ng/mL (with untreated controls having blood insulin of 0.15-0.25 ng/mL). Glucose tolerance and insulin tolerance tests performed in wild type non-diabetic animals after IGFBP-2 treatment indicate that such treatment can confer increased glucose and insulin tolerance in wild-type animals. We therefore conclude that normal healthy mice respond in a similar manner as do Type 1 and Type 2 diabetic mice to IGFBP-2 treatment although the change is not as great because their blood glucose and serum insulin are not elevated to start with.

Example 5

IGFBP-2 Treatment Corrects Hyper-Insulinemia in ob/ob Type 2 Diabetic Mice

To determine the effect of IGFBP-2 on insulin levels, ob/ob animals were intrajugularly injected with Ad-CMV-IGFBP- 2, Ad-CMV-empty, or Ad-CMV-luciferase virus. After 5 days, Ad-CMV-luciferase animals were assayed for hepatic expression of luciferase. Ad-CMV-IGFBP-2 and Ad-CMV-empty animals were assayed for serum IGFBP-2 levels to confirm secretion of IGFBP-2 into the blood stream. Results indicated both robust expression and secretion of IGFBP-2. Daily weight and food intake was recorded as shown in example 2 and blood glucose and insulin was assayed. Serum insulin levels dropped very significantly from 86.5+/−6.8 ng/mL to 4.88+/−1.7 ng/mL.

Example 6

IGFBP-2 Treatment Corrects Hepatic Steatosis in Ob/Ob Diabetic Mice

Figure 6:
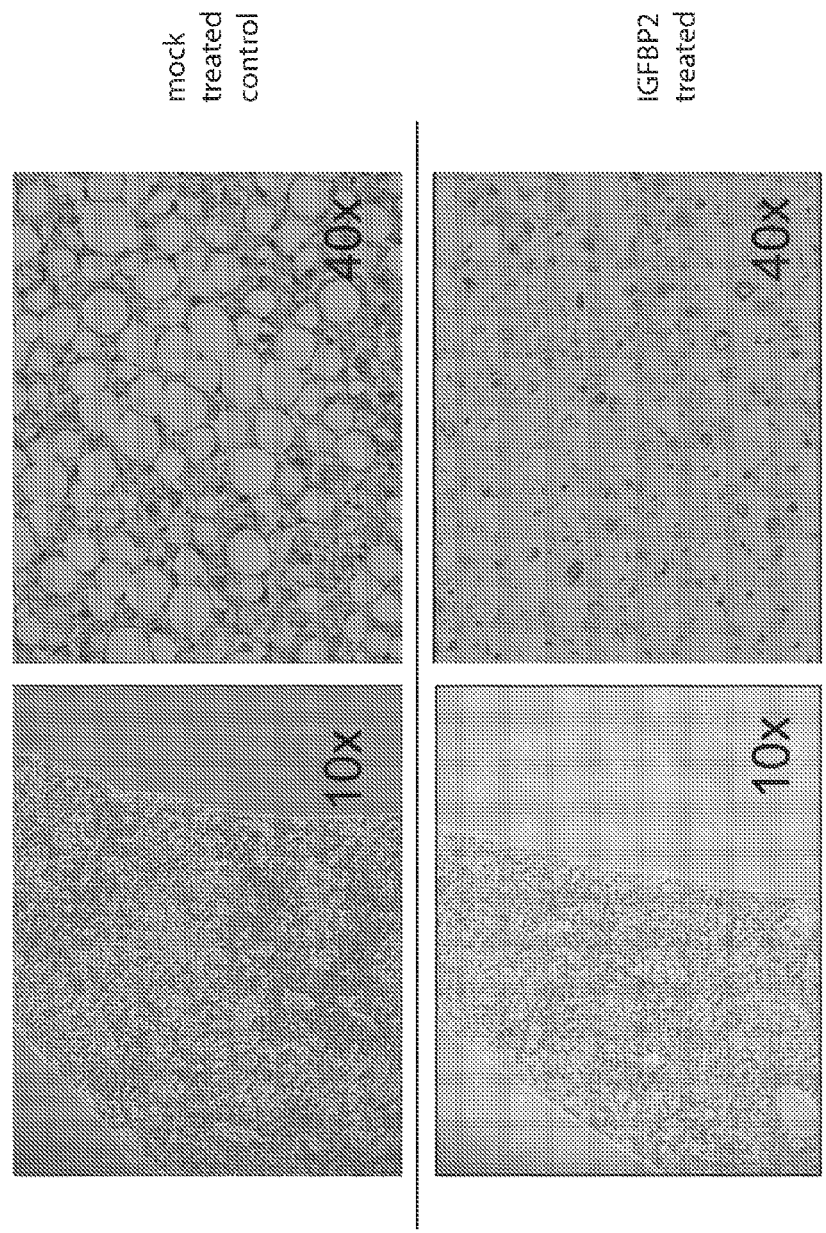
FIG. 6 are photographs showing that IGFBP-2 treatment corrects hepatic steatosis in ob/ob diabetic mice.

Liver sections of ob/ob diabetic mice treated with Ad-CMV-IGFBP-2 or control (Ad-CMV-empty) were examined. As shown in FIG. 6, control ob/ob animals had massive fat vacuoles characteristic of hepatic steatosis. IGFBP-2 treated ob/ob animals, however, showed remarkable reversal of hepatic steatosis.

Example 7

IGFBP-2 Treatment Corrects Hyperglycemia In Type 1 Diabetic Mice

Figure 7:
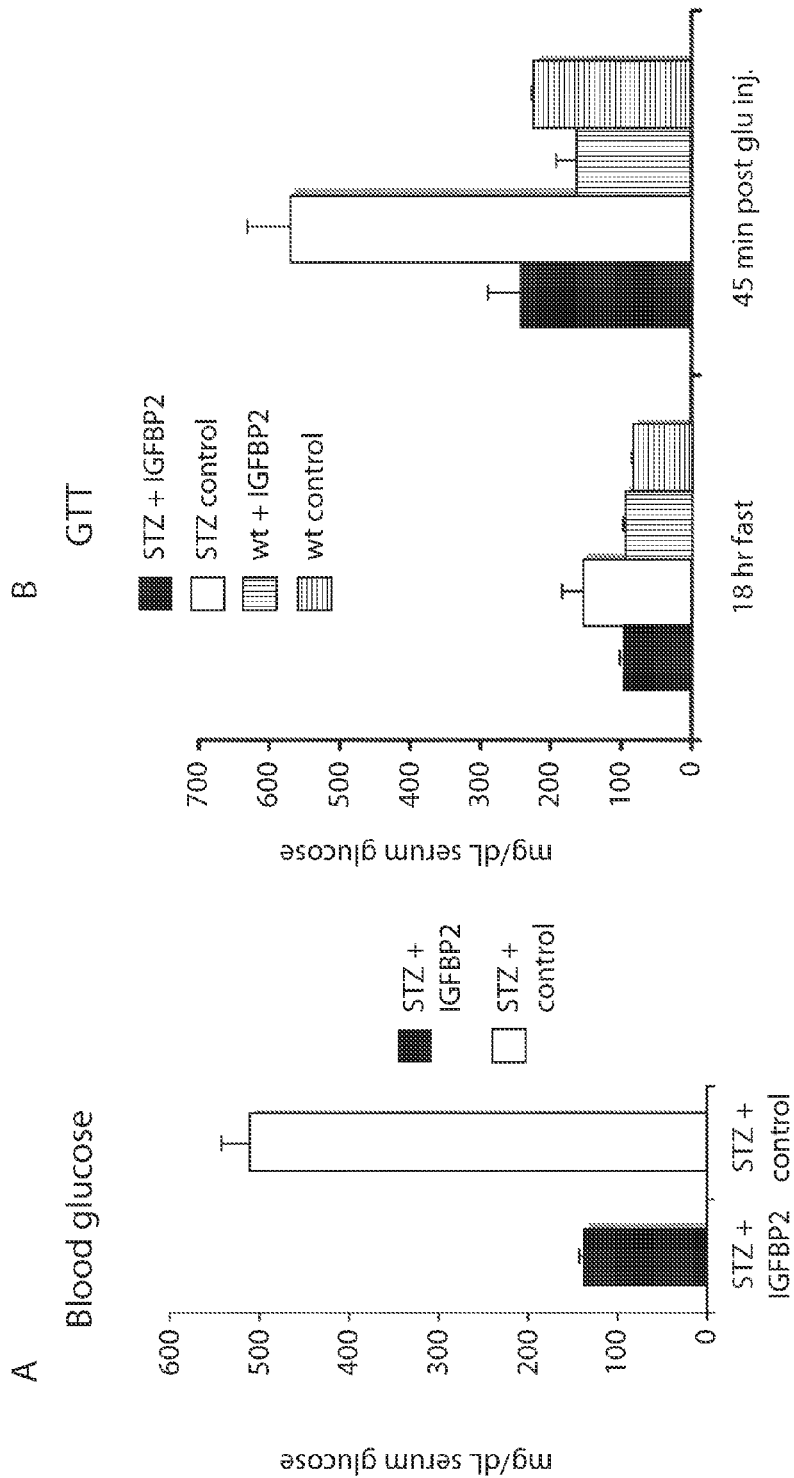
FIG. 7 is a graph showing that IGFBP-2 treatment corrects hyperglycemia in STZ-induced Type 1 diabetic mice.

STZ diabetic mice were injected with IGFBP-2 to investigate the mechanism of IGFBP-2 mediated correction of hyperglycemia. STZ diabetic mice are wild type mice made severely hypoinsulinemic by ablation of pancreatic beta-cells by repeated IP streptozotocin (STZ) injections. As a result, these animals develop severe hyperglycemia that is lethal if left untreated. No serum insulin was detected above the control (blank) at 6 weeks post STZ-treatment despite extremely hyperglycemic conditions using a regular mouse insulin EIA kit. Fasting (4 hrs) glucose was between 360 and 650 mg/dL. Ad-CMV-IGFBP-2 or Ad-CMV-empty were introduced by intrajugular injection and 5 days were allowed for full expression. As shown in FIG. 7, IGFBP-2 treated animals showed a remarkable reduction in blood glucose. Mock treated (Ad-CMV-empty) control animals had fasting (5 hour) glucose levels 509.5+/−32.9 mg/dL, whereas IGFBP-2 treated animals had fasting blood glucose of 136.0+/−6.9 mg/dL. A glucose tolerance test was performed after an 18 hour fast. IGFBP-2-treated animals had glucose levels at 244+/−44 mg/dL 45 minutes after glucose injection whereas control animals had glucose levels of 569+/−61 mg/dL. This implies that glucose metabolism/turnover is remarkably improved in IGFBP-2 treated Type 1 diabetic animals.

Example 8

Leptin regulation of IGFBP-2

We hybridized liver RNA prepared from animals receiving 12 days of 0, 12.5 or 25 ng/hour leptin to generate transcriptional profiles using Illumina™ (San Diego, Calif.) microarrays. Total RNA was isolated by homogenizing liver tissue in TRIzol™ reagent (Invitrogen, Carlsbad, Calif.) and purifying the RNA using Qiagen RNA prep kit (Qiagen, Valencia, Calif.). Real-time PCR was performed using the TaqMan™ system (Applied Biosystems, Foster City, Calif.) according to the manufacturer's protocol as previously described (Birsoy et al., Transcriptional regulation of adipogenesis by KLF4. Cell Metab 7, 339-347, 2008). Microarrays were done using MouseRef-8 v2 BeadChip™ (part#11288185) after labeling the RNA with Ambion's (Austin, Tex.) Illumina TotalPrep™ RNA Amplification Kit. The aggregate results for gene expression for each of these experiments are provided (FIG. 8). Data were analyzed by generating an ordered list of induced genes, comparing the levels of gene expression in liver RNA prepared from the animals treated with 25 and 12.5 ng/hour of leptin to the PBS control mice. For the 25 ng/hour group, the two most significantly induced genes were Serpina1e, a protease inhibitor, and MUP, a testosterone sensitive urinary protein. The third most prominently induced gene on this list was IGFBP-2, a plasma protein with IGF binding activity. IGFBP-2 has been shown to inhibit IGF activity in some assays though its precise biologic function is unknown (Firth and Baxter, Cellular actions of the insulin-like growth factor binding proteins. Endocr Rev 23, 824-854, 2002; Kelley et al., Insulin-like growth factor-binding proteins (IGFBPs) and their regulatory dynamics. Int J Biochem Cell Biol 28, 619-637.1996). IGFBP-2 was upregulated 5.28-fold at the 25 ng/hour leptin dose, (p<0.01) and 1.6 fold in the 12.5 ng/hour mice compared to PBS controls, (p<0.01) (FIG. 8).

We also used a Taqman assay to confirm that IGFBP-2 mRNA was regulated by leptin. IGFBP-2 mRNA levels were upregulated 2-fold in the 12.5 ng/hour mice compared to controls (0.6 vs. 0.2, p=0.11), 3-fold in 25 ng/hour mice (0.9 vs. 0.2, p<0.05), 10-fold in 50 ng/hour mice (2.7 vs. 0.2, p<0.05), and 13-fold in 100 ng/hour mice (3.2 vs. 0.2, p<0.05) (FIG. 9A).

The effect of leptin treatment on plasma levels of IGFBP-2 was measured using an Elisa (EIA) assay. IGFBP-2 circulates at a level of 396 ng/mL in wild type mice and its baseline levels are significantly reduced in ob/ob to 31 ng/ml, p<0.01 (FIG. 9B-9C). Leptin significantly increased plasma IGFPB2 levels in ob/ob mice by the 4th day of treatment, with the 100 ng/hour leptin dose increasing it 8-fold by the 12th day (246 vs. 31 ng/mL in ob/ob mice, p<0.01). IGFBP-2 levels increased 4.3-fold in the 25 ng/hour group (132 vs. 31 ng/mL in ob/ob mice, p<0.01) by the 12th day. There was also a similar trend toward increased levels of IGFBP-2 in the 12.5 ng/hour group (FIG. 9B).

Figure 5:
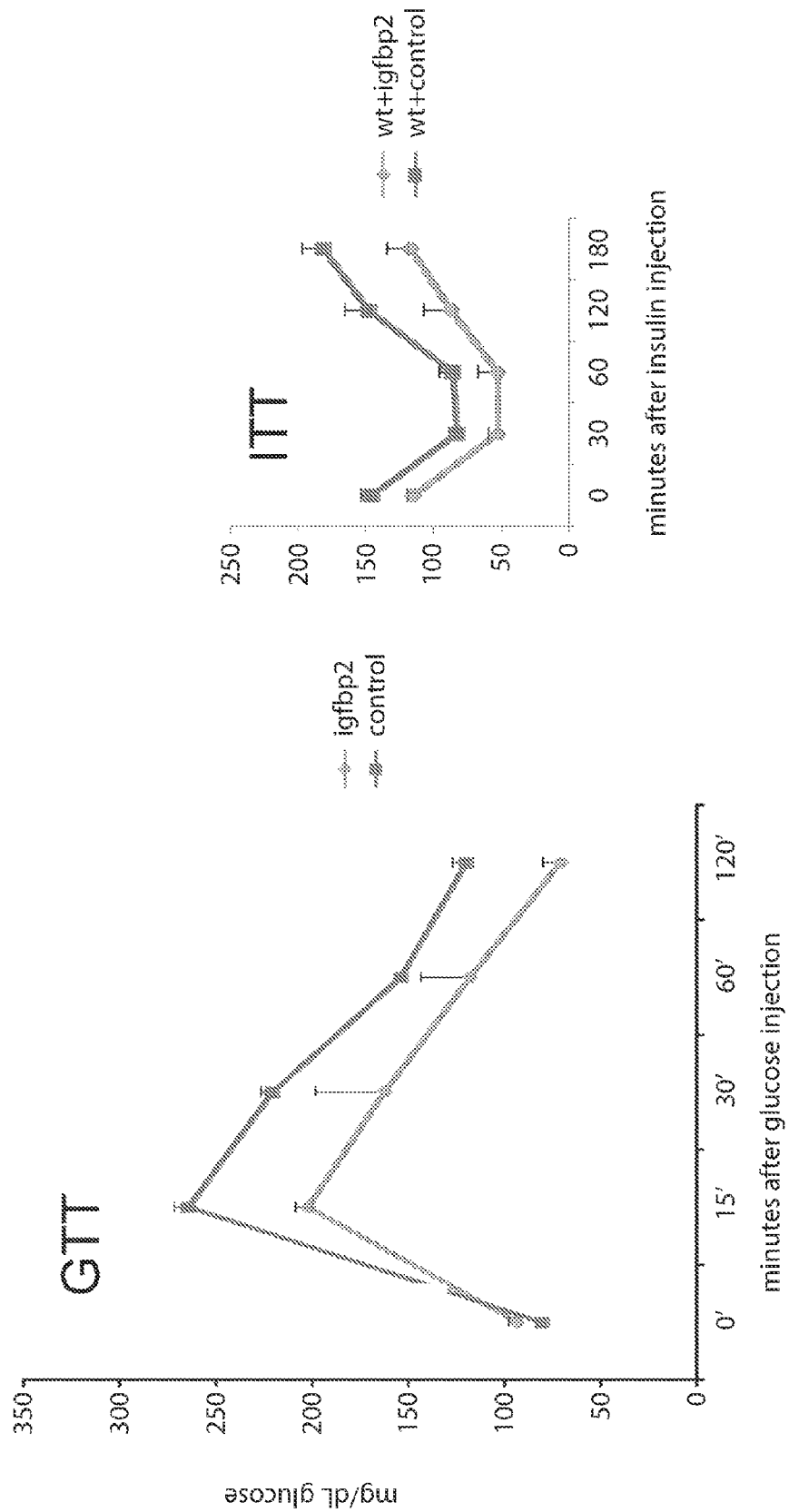
FIG. 5 is a graph showing glucose tolerance test (and insulin tolerance test) in wild type non-diabetic animals after IGFBP-2 treatment.
Figure 10F:
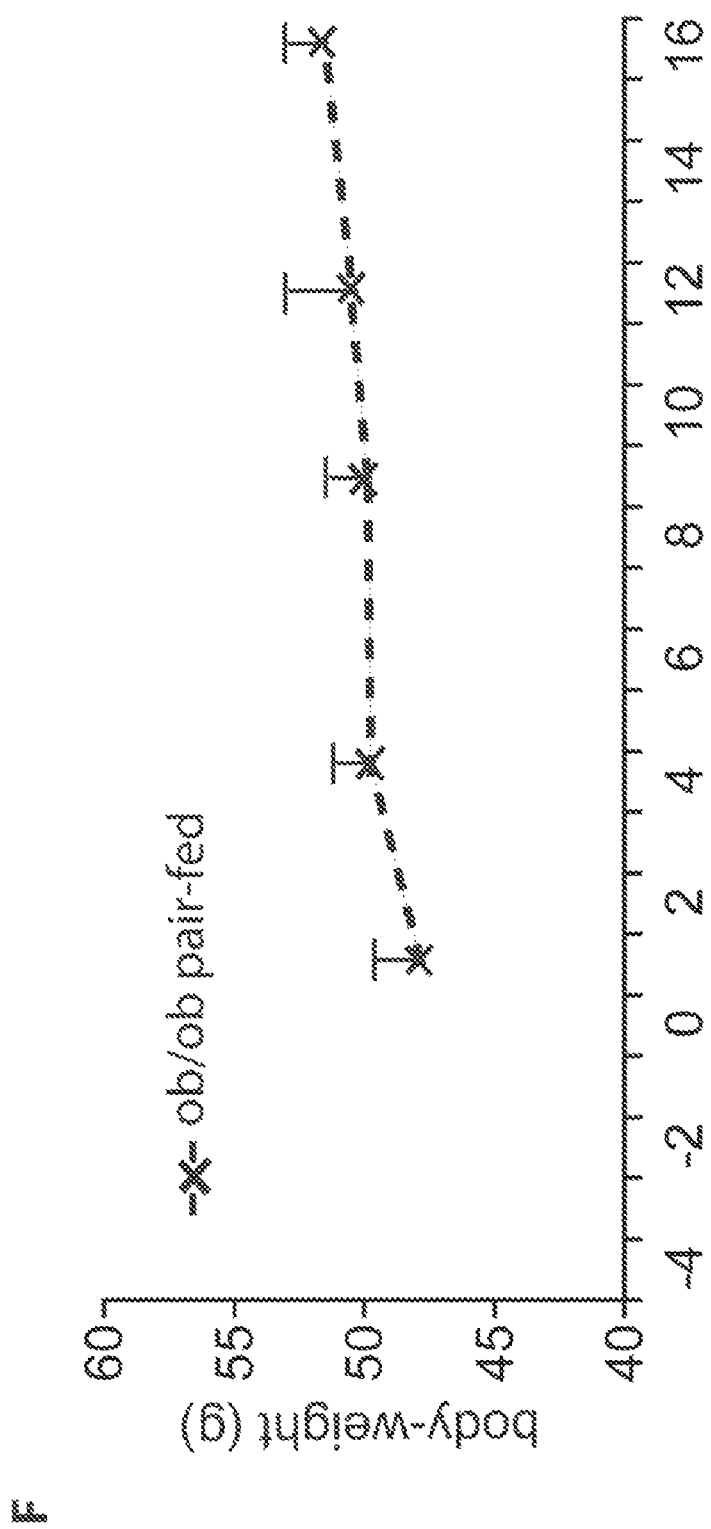
FIG. 10 shows various experiments A and B) Glucose uptake in Ad-IGFBP2 treated ob/ob. Glucose uptake assay in A) white adipose tissue (WAT) and B) muscle. Ob/ob mice treated with Ad-IGFBP2 or Ad-control. C) Ketoacidosis. Plasma ketone bodies measured in mM beta-hydroxybutyrate. Untreated wildtype (WT) as reference and STZ and ob/ob+/−Ad-IGFBP2. D and E) Acute increase in insulin does not affect IGFBP2 plasma level. D) showing blood glucose in wildtype mice injected with PBS or insulin at time 0, 1 hr and 3 hr post injection. E) Resulting plasma IGFBP2 levels in animals from panel D. F) Error bars for pairfed animals in FIG. 12A.

Because low doses of leptin markedly improve insulin sensitivity, we considered the possibility that the leptin mediated induction of IGFBP-2 was insulin dependent. We tested this possibility in two ways. First, ob/ob mice were severely food restricted (0.5 grams/day for 12 days—this is the voluntary food intake of ob/ob mice receiving 200 ng/hr leptin) which resulted in insulin levels falling by 90%. Despite this reduction in plasma insulin, plasma IGFBP-2 remained constant between food-restricted and controls (35 ng/mL in food restricted vs. 34 ng/mL eating ad libitum, p>0.7) (FIG. 9C). We further examined the relationship between insulin levels and IGFBP-2 expression by injecting wildtype animals with a bolus of insulin and found that an acute injection of insulin failed to increase plasma IGFBP-2 levels at 1 and 3 hours post-injection (FIG. 10D-10E). Consistent with these results, the baseline levels of IGFBP-2 were similar among several different animals with markedly different baseline levels of insulin, including wild type mice, Type 1 diabetic mice resulting from streptozotocin treatment (STZ), and Ay and Diet Induced Obese (DIO) mice as well as Srebp-1c diabetic mice (FIGS. 9C and 5B).

Example 9

Figure 11:
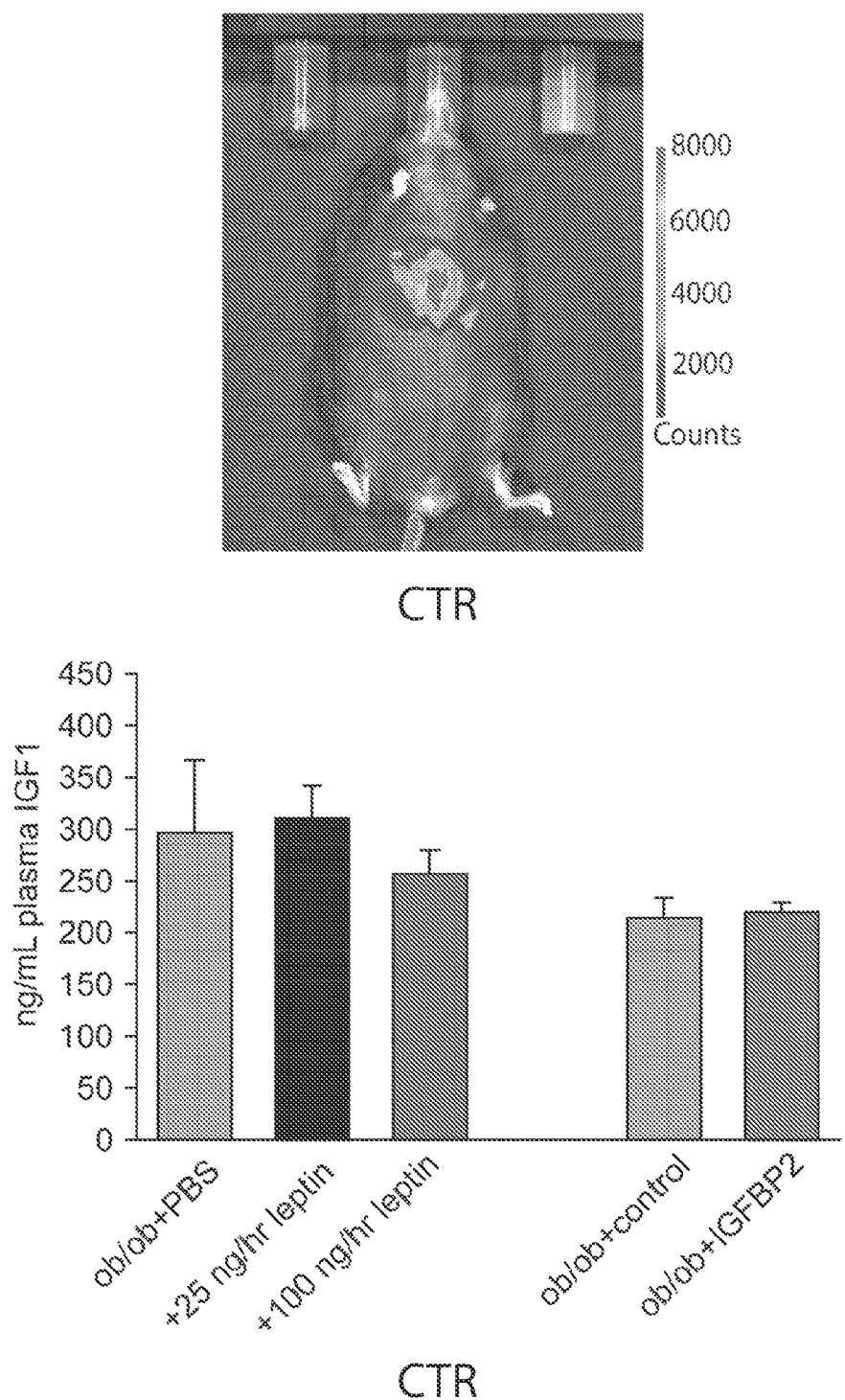
FIG. 11 shows: A) sites of gene expression from the viral vector in treated mice as described in the Examples; and B) serum levels of IGF1 in various mice as indicated.

Ad-IGFBP-2 Treatment Corrects Hyperglycemia, Hyperinsulinemia, and Hepatic Steatosis in ob/ob Diabetic Mice We next tested whether over-expression of IGFBP-2 can correct hyperglycemia and hyperinsulinemia in diabetic mice. A mouse IGFBP-2 cDNA was cloned into an empty shuttle adenoviral vector under the control of the CMV promoter. This is a gutless adenoviral vector that fails to express adenoviral genes, thus mitigating secondary effects of the viral infection. As a control, we used additional adenovirus strains with no insertion or with an insertion of a luciferase reporter. The luciferase virus allowed us to assess the sites of gene expression from the viral vector. Five days after intravenous injections of the Ad-luciferase adenovirus, mice received an intraperitoneal injection of luciferin and were imaged using a CCD camera (IVUS, Caliper Technology). These data showed that viral gene expression was limited to the liver, the site of endogenous IGFBP-2 expression, and also at the site of injection in the tail (FIG. 11A).

Animals injected with the IGFBP-2 adenovirus showed a highly significant increase in plasma IGFBP-2 levels to at least 4000 ng/mL (data not shown). The IGFBP-2 and empty (control) adenoviruses were injected into ob/ob mice followed by measures of daily body weight and food intake (FIGS. 12A and 12B) and plasma glucose and insulin five days after viral injection (FIGS. 12C and 12D). Mice treated with the IGFBP-2 adenovirus showed a modest decrease in food intake with a stabilization of body weight while the control ob/ob mice continued to gain weight (FIGS. 12A and 12B). At 5 days post-injection, the ob/ob mice that had received the IGFBP-2 treatment had completely normalized plasma glucose and insulin. While control mice had blood glucose levels of over 300 mg/dL, IGFBP-2 treated animals had blood glucose levels under 100 mg/dL (320 vs. 94 mg/dL for the controls, $p<0.01$) (FIG. 12C). Plasma insulin levels were also normalized in the IGFBP-2 treated mice (85 vs. 5 ng/mL, $p<0.01$) (FIG. 12D). ob/ob mice pair-fed to the IGFBP-2-treated ob/ob animals failed to show a significant reduction of blood glucose or plasma insulin (FIGS. 12A, 12B, 12C and 12D).

We performed glucose tolerance tests (GTT) in the IGFBP-2-treated mice. While plasma glucose levels of the control mice peaked above 550 mg/dL at 30 minutes post glucose-injection, the blood glucose of IGFBP-2-treated mice remained below 300 mg/dL (559 vs. 288 mg/dL, $p<0.01$) (FIG. 13A). GTT of IGFBP-2 treated ob/ob showed a complete correction of glucose clearance in response to a glucose challenge (compare FIG. 13A and FIG. 14E).)

To assess the mechanism of these effects, we utilized hyperinsulinemic-euglycemic clamps to study insulin sensitivity, hepatic glucose output, and glucose uptake in treated and control mice. Hyperinsulinemic euglycemic clamps were performed essentially as described in (Qi et al., Loss of resistin improves glucose homeostasis in leptin deficiency. Diabetes 55, 3083-3090, 2006). 10 week old male ob/ob mice were treated with Ad-CMV-IGFBP-2 or Ad-CMV-control via a tail vein injection, and insulin clamp was performed 10 days later. An indwelling catheter was inserted in the right internal jugular vein under sodium pentobarbital anesthesia and extended to the right atrium. After regaining their presurgery weight (4 days), the mice were fasted for 6 hours, a bolus injection of 5 µCi of [3-3H] glucose was administered, followed by continuous intravenous infusion at 0.05 µCi/min. Baseline glucose kinetics was measured for 60 min. A priming dose of regular insulin (40 mU/kg, Humulin; Eli Lilly, Indianapolis, Ind.) was given intravenously, followed by continuous infusion at 30 mU·kg-1·min-1. Blood glucose was maintained at 120-140 mg/dL via a variable infusion rate of 30% glucose. At the end of the 120-minute clamp, 10 µCi 2-deoxy-D-[1-14C]glucose was injected to estimate glucose uptake. The mice were euthanized, and liver, perigonadal fat (WAT), and soleus/gastrocnemius muscle were excised, frozen immediately in liquid nitrogen, and stored at −80° C. for subsequent analysis of glucose uptake. The rates of basal glucose turnover and whole body glucose uptake are measured as the ratio of [3H] glucose infusion rate (dpm) to the specific activity of plasma glucose. Hepatic glucose production (HGP) during clamp is measured by subtracting the glucose infusion rate (GIR) from the whole body glucose uptake (Rd).

The hyperinsulinemic euglycemic clamps studies found that the glucose infusion rates (GIR) required to maintain blood glucose levels at ~140 mg/dL were 3.6-fold higher in IGFBP-2-treated animals compared to controls (36 mg/kg/min in IGFBP-2-treated ob/ob vs. 10 mg/kg/min in controls, $p<0.01$) (FIG. 13C), thus showing a marked effect of IGFBP-2 to improve insulin sensitivity. Hepatic glucose production (HGP) during the insulin clamp of IGFBP-2-treated mice was 11 mg/kg/min compared to 32 mg/kg/min in controls ($p<0.01$) (FIG. 13E). In response to the super-physiological 30 mU/kg/min insulin infusion, the HGP was suppressed by 77% of the basal glucose production in IGFBP-2 treated ob/ob versus 34% suppression in controls, $p<0.01$) (FIG. 13F). In contrast, the glucose disappearance rate (Rd) during the clamp was not significantly different between IGBP2-treated and control ob/ob mice (FIG. 13D). We also measured 2-deoxyglucose uptake in WAT and gastrocnemius/soleus muscle at the end of the clamp. WAT glucose uptake was not affected by IGFBP-2 treatment (FIG. 10A). Muscle glucose uptake was slightly increased in IGFBP-2-treated ob/ob relative to wildtype but the difference was not statistically significant (25 nmol/g/min in IGFBP-2-treated vs. 17 in controls, p=0.1) (FIG. 10B). Together, these results demonstrate that IGFBP-2 treatment markedly increases insulin sensitivity primarily by suppressing hepatic glucose output.

We performed Taqman assays for PEPCK and G6Pase, both of which play a key role to regulate hepatic gluconeogenesis. PEPCK was reduced 46% ($p<0.01$) and G6Pase was reduced 43% ($p<0.05$) after Ad-IGFBP-2 infection in ob/ob livers (FIG. 13B). These data are consistent with the observation that IGFBP-2 suppressed HGP as shown in the hyperinsulinemic clamp studies.

The improvement in hepatic insulin sensitivity by IGFBP-2 treatment was associated with a significant reduction of hepatic steatosis. Liver histology showed a drastic reduction in lipid droplets in the livers of Ad-IGFBP-2-treated ob/ob mice (FIG. 12F). Liver triglycerides were significantly reduced by IGFBP-2 and low-dose leptin treatment (FIG. 12E). Consistent with an improvement in hepatic steatosis, fatty acid synthase (FAS) gene expression was downregulated 32% ($p<0.05$) in Ad-IGFBP-2 treated livers compared to controls (FIG. 13B).

Example 10

Figure 15:
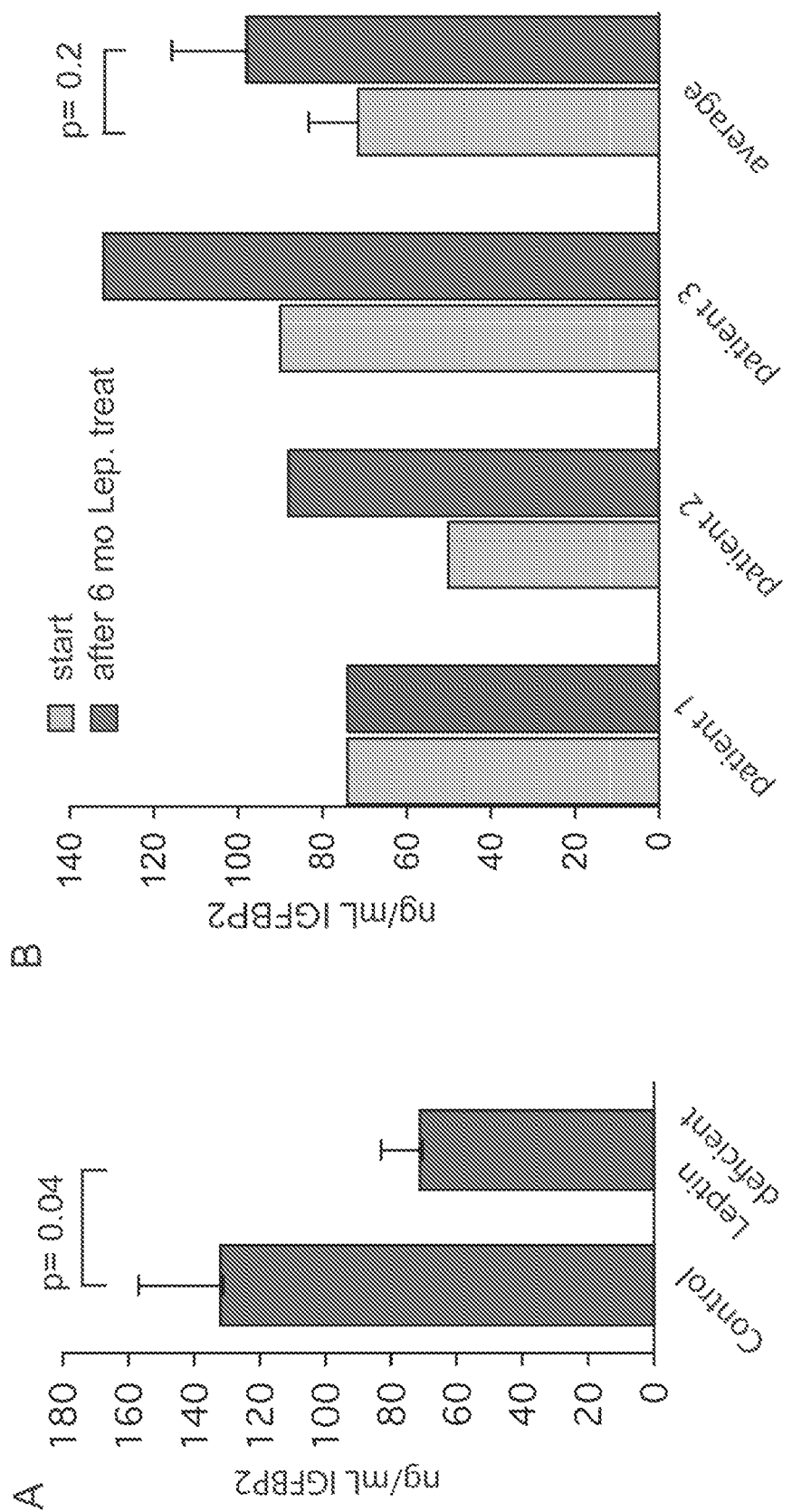
FIG. 15 shows that IGFBP2 is regulated by Leptin in humans. A) Serum IGFBP2 in leptin deficient and age and weight-matched controls. B) Serum IGFBP2 in 3 leptin deficient patients before (light grey), and 6 months after (dark grey) low-dose leptin treatment.

IGFBP-2 Over-Expression in Wild Type Mice and Other Leptin-Resistant Diabetic Mouse Strains We next tested the effect of IGFBP-2 over-expression in wild type mice and other leptin-resistant diabetic mouse strains. In each case, plasma [glucose] was significantly decreased in the animals receiving the IGFBP-2 adenovirus. By the 6th day after IGFBP-2 infection, blood glucose in wild type mice fell 37% (90 vs. 142 mg/dL, $p<0.01$); in DIO animals, blood glucose fell 32% (117 vs. 171 mg/dL, $p<0.01$), and finally blood glucose fell 34% in Ay mice (134 vs. 202 mg/dL, $p<0.05$) (FIG. 15A). There was a trend for reduction in insulin levels in all these mice although it only reached significance in Ay mice (FIG. 15B). The levels of blood glucose during glucose tolerance tests were also significantly reduced at all time points including the peak level in wild type, Ay, and DIO mice treated with the IGFBP-2 adenovirus vs. controls (FIGS. 15E, 15F, 15G and 15H). Changes in food intake and body weight were minimal and in most cases not statistically significant between experimentals and controls (FIGS. 15C and 15D).

Example 11

Ad-IGFBP-2 Treatment Corrects Hyperglycemia in Insulin Deficient Mice

Previous studies have shown that leptin treatment corrects hyperglycemia in Type 1 diabetic mice (Yu et al., Making insulin-deficient type 1 diabetic rodents thrive without insulin. Proc Natl Acad Sci USA 105, 14070-14075, 2008). We next tested whether IGFBP-2 can improve diabetes in this setting of insulin deficiency. IGFBP-2 was injected into streptozotocin-induced insulin deficient mice. Plasma insulin was not detectable 6 weeks post low-dose STZ-treatment even when using an ultra-sensitive mouse insulin EIA kit (FIG. 15B and data not shown). At day 5 after IGFBP-2-injections, control mice had fasting (4 hour) glucose levels of 509 as compared to 136 mg/dL of the IGFBP-2-treated group, $p<0.01$ (FIG. 16A). Glucose tolerance tests were also markedly improved at 45 minutes (654 vs. 342 mg/dL, $p<0.05$) (FIG. 15G). Food intake and body weight were not changed in either groups (FIGS. 15C and 15D).

Example 12

IGFBP-2 Levels in Leptin-Deficient Patients

Finally we assessed whether IGFBP-2 regulation by leptin is evident in human subjects. To this end, we obtained sera from three leptin deficient patients and age and weight-matched controls, before and after 6 months of daily subcutaneous low-dose leptin treatments. These patients and their treatment have been previously described (Farooqi et al., Beneficial effects of leptin on obesity, T cell hyporesponsiveness, and neuroendocrine/metabolic dysfunction of human congenital leptin deficiency. J Clin Invest 110, 1093-1103). All samples were stored at minus 80 C and thawed once prior to analysis There was a two-fold decrease in baseline serum IGFBP-2 levels in the leptin-deficient (LEP/LEP) versus control patients (leptin deficient patients had 71 ng/mL serum IGFBP-2 vs. 132 ng/mL of controls, $p=0.04$) (FIG. 16A). After low-dose leptin treatment, IGFBP-2 levels increased in 2 out of 3 patients; from 50 to 88 ng/mL in Patient 1, 90 to 132 ng/mL in Patient 2, while one patient showed no change (74 and 74 ng/mL). The average levels of IGFBP-2 before and after leptin treatment were 71 ng/mL and 98 ng/mL respectively, $p=0.2$ (FIG. 16B).

Example 13

Methods for Producing Recombinant IGFBP-2

Recombinant IGFBP-2 can be made by a variety of expression systems suitable for production of heterologous proteins. In one embodiment, stably transfected mammalian cell lines comprising a recombinant IGFBP-2 mammalian cell expression vector can be made by using the cGMP Cell Line Nucleofector® Kits (Lonza Walkersville, Inc. Walkersville, Md.). Suitable cells that can be used for stable eukaryotic expression/cGMP production of IGFBP-2 include, but are not limited to, CHO, sCHO, 293, suspension 293 cells, NIH 3T3, and NSO cells. In one embodiment, a system that facilitates high levels of protein expression by selecting for gene amplification of GST together with the cloned sequence, in this case IGFBP-2, can be used. Recombinant IGFBP-2 in it's mature form can be purified from culture media obtained from cells that express this recombinant protein. As quality control measure, recombinant IGFBP-2 can be tested for bioactivity by assaying its ability to inhibit the biological activity of rmIGF-II on MCF-7 cells. IGF-II is the natural substrate of IGFBP-2.

Example 14

Testing of Recombinant IGFBP-2 in Mouse Model Systems

Different mouse models of diabetes (ob/ob (leptin-deficient), diet-induced obese (DIO), agouti (Ay), streptozytocin (STZ)-induced hyperglycemic) as well as control wild-type mice can be treated with recombinant IGFBP-2 protein as follows.

In one case, treatment can be performed by continuous subcutaneous delivery of bioactive recombinant IGFBP-2. Capsules (Alzet Mini-osmotic pumps model 2002) can be implanted under the skin dorsally on subject mice (wildtypes, ob/ob, DIO, Ay, STZ-induced diabetic mice) and then monitored for correction of hyperglycemia (and hyperinsulinemia, insulin sensitivity, and hepatic steatosis as relevant). We have determined that IGFBP-2 protein is soluble in PBS at least 10 mg/mL. Therefore, experiments can be conducted by using osmotic pumps filled with 10 mg/mL, 3.3 mg/mL and 1.1 mg/mL IGFBP-2 as well as PBS-filled controls. In this example, 10 mg/mL IGFBP-2 protein is used as the highest concentration working solution and the decreased doses calculated by dividing three-fold. The resulting circulating levels of IGFBP-2 in the bloodstream are assayed to establish dose-given:resultant circulating levels and dose-given:degree of correction in hyperglycemia (and hyperinsulinemia, insulin sensitivity, and hepatic steatosis as relevant) for the above IGFBP-2 concentrations.

In another case, treatment can be performed by delivery of bioactive recombinant IGFBP-2 protein using intraperitoneal injections. Subject mice (wildtypes, ob/ob, DIO, Ay, STZ-induced diabetic mice) can be injected intraperitoneally with 200 uLs of 10 mg/mL, 3.3 mg/mL and 1.1 mg/mL IGFBP-2, as well as PBS, twice daily and then monitored for both: i) resulting blood plasma levels of IGFBP-2 in the subject mice (wildtypes, ob/ob, DIO, Ay, STZ-induced diabetic mice) and ii) improvement of hyperglycemia (and hyperinsulinemia, insulin sensitivity, and hepatic steatosis as relevant). Any of acute, sustained, and/or chronic injections of recombinant IGFBP-2 can be used.

In another case, treatment can be performed by delivery of bioactive recombinant IGFBP-2 protein using gavage method. Subject animals (wildtypes, ob/ob, DIO, Ay, STZ-induced diabetic mice) can be gavaged with 10 mg/mL, 3.3 mg/mL and 1.1 mg/mL IGFBP-2 as well as PBS at 10 mL/kg mouse. Correction of hyperglycemia (and hyperinsulinemia, insulin sensitivity, and hepatic steatosis as relevant) on a time line following ingestion, as well as resulting levels in the blood stream at each dose can be monitored.

In another case, treatment can be performed by intravenous delivery of bioactive recombinant IGFBP-2 protein. Subject mice (wildtypes, ob/ob, DIO, Ay, STZ-induced diabetic mice) can be intravenously injected with 200 uLs of 10 mg/mL, 3.3 mg/mL and 1.1 mg/mL IGFBP-2, as well as PBS, once daily and then monitored for resulting blood plasma levels of IGFBP-2 in subjects and improvement of hyperglycemia (and hyperinsulinemia, insulin sensitivity, and hepatic steatosis as relevant) both with acute, sustained, and chronic injections.

Using the above methods for production and delivery of recombinant IGFBP-2, it will be possible to determine the exact administered dose of recombinant IGFBP-2 necessary to achieve the levels in the blood stream that have been established as sufficient for correction of hyperglycemia and hyperinsulinemia, insulin resistance (and hepatic steatosis) in diabetic mice treated with the IGFBP-2 viral expression vector Ad-CMV-IGFBP-2. It will also be possible to determine the exact minimum dose of administered recombinant IGFBP-2 protein that is required for correction of hyperglycemia and hyperinsulinemia (and hepatic steatosis) in diabetic mice. Furthermore, it will be possible to determine how quickly after administration of IGFBP-2 protein that a correction of hyperglycemia (and hyperinsulinemia, insulin sensitivity, and hepatic steatosis as relevant) is experienced by the subject (diabetic mouse).

Example 15

Determination of Therapeutically Effective Blood Plasma Levels of IGFBP-2

In experiments with the IGFBP-2 viral expression vector Ad-CMV-IGFBP-2, an achieved level of at least 6000 ng/mL in blood plasma was found to treat diabetes in assayed diabetic mice (ob/ob, DIO, Ay, and STZ) or to lower blood glucose in wildtype mice. The average endogenous levels of IGFBP-2 in wildtype, DIO, Ay and STZ mice range on average between 300 and 400 ng/mL. We refer to this as "normal" IGFBP-2 blood plasma levels. ob/ob mice have unusually low endogenous IGFBP-2 levels at 30-40 ng/mL which measures ⅒ of that found in wildtypes and other diabetic mice not deficient in leptin (DIO, Ay, STZ). Our experiments suggest the low IGFBP-2 levels found in ob/ob mice are explained by the fact that they are leptin deficient and leptin positively regulates IGFBP-2 production by the liver which is subsequently secreted into the blood stream. In ob/ob diabetic mice, a range between 6884 ng/mL IGFBP-2 and 107200 ng/mL IGFBP-2 all lowered the blood sugar of diabetic ob/ob mice by at least 48.3% compared to control-treated mice. In the case of ob/ob diabetic mice, 6884 ng/mL represents an IGFBP-2 blood plasma concentration that is approximately 150-200 fold above endogenous IGFBP-2 blood plasma concentration levels that occur in untreated ob/ob diabetic mice or 15-20 fold above "normal" IGFBP-2 blood plasma. Therefore, an achieved IGFBP-2 protein concentration level in the blood stream sufficient to correct hyperglycemia in diabetic mice is 15-fold above the "normal" IGFBP-2 blood plasma levels. The highest achieved dose of blood plasma IGFBP-2 not sufficient to correct hyperglycemia in assayed mice was 8 times the "normal" levels of endogenous IGFBP-2. Therefore, the lowest achieved level of IGFBP-2 level in the blood plasma of assayed mouse models for diabetes and wildtype mice is in a range greater than 8-fold "normal" blood plasma IGFBP-2 levels. Levels above 15-20 fold "normal" IGFBP-2 levels had no adverse effects on glycemic levels. Assayed mouse models (wildtype, ob/ob, DIO, Ay, and STZ) did not experience hyperglycemia or other obvious contraindications.

The discussion of the references herein is intended merely to summarize the assertions made by their authors and no admission is made that any reference constitutes prior art. Applicant reserves the right to challenge the accuracy and pertinence of the cited references.

In view of the above, it will be seen that the several advantages of the invention are achieved and other advantageous results attained. As various changes could be made in the above methods and compositions without departing from the scope of the invention, it is intended that all matter contained in the above description and shown in the accompanying drawings shall be interpreted as illustrative and not limiting in a limiting sense. Thus, the breadth and scope of the present invention should not be limited by any of the above-described exemplary embodiments, but should be defined only in accordance with the following claims appended hereto and their equivalents.

What is claimed is:

1. A method of treating Type 1 diabetes comprising the step of administering a therapeutically effective amount of a mature Insulin-like Growth Factor-binding protein-2 (IGFBP-2) to a subject in need thereof.

2. The method of claim 1, wherein the subject is a human.

3. The method of claim 1, wherein the mature Insulin-like Growth Factor-binding protein-2 is administered to the subject orally, topically, rectally, percutaneously, by parenteral injection, intranasally, or by inhalation.

4. The method of claim 1, wherein the therapeutically effective amount of the mature Insulin-like Growth Factor-binding protein-2 administered comprises an amount that provides for an increase of at least about 2-fold to about 5-fold in a blood serum level of IGFBP-2 in said subject.

5. The method of claim 1, wherein the therapeutically effective amount provides for a fasting blood serum glucose level of about 90 mg/dL to 105 mg/dL.

6. The method of claim 1, wherein the therapeutically effective amount provides for blood serum glucose levels of less than 300 mg/dL at 45 min post intraperitoneal administration of a glucose solution at a dose of about 1 unit glucose per gram weight of said subject.

7. A method of treating Type 2 diabetes comprising the step of administering a therapeutically effective amount of a mature Insulin-like Growth Factor-binding protein-2 to a subject in need thereof.

8. The method of claim 7, wherein the subject is a human.

9. The method of claim 7, wherein the mature Insulin-like Growth Factor-binding protein-2 is administered to the subject orally, topically, rectally, percutaneously, by parenteral injection, intranasally, or by inhalation.

10. The method of claim 7, wherein the therapeutically effective amount of the mature Insulin-like Growth Factor-binding protein-2 administered comprises an amount that provides for an increase of at least about 2-fold to about 5-fold in a blood serum level of IGFBP-2 in said subject.

11. The method of claim 7, wherein the therapeutically effective amount of the mature Insulin-like Growth Factor-binding protein-2 results in a fasting blood serum glucose level between about 80 mg/dL to about 110 mg/dL.

12. The method of claim 7, wherein the therapeutically effective amount of the mature Insulin-like Growth Factor-binding protein-2 results in a fasting blood serum insulin level of about 3 ng/mL to about 1 ng/mL.

13. The method of claim 1, wherein said therapeutically effective amount of the mature Insulin-like Growth Factor-binding protein-2 (IGFBP-2) is provided by administration of a recombinant Insulin-like Growth Factor-binding protein-2 (IGFBP-2) or a PEGylated recombinant IGFBP-2 protein to said subject.

14. The method of claim 7, wherein said therapeutically effective amount of the mature Insulin-like Growth Factor-binding protein-2 (IGFBP-2) is provided by administration of a recombinant Insulin-like Growth Factor-binding protein-2 (IGFBP-2) or a PEGylated recombinant IGFBP-2 protein to said subject.

* * * * *

SEQUENCE LISTING

```
<160> NUMBER OF SEQ ID NOS: 30

<210> SEQ ID NO 1
<211> LENGTH: 328
<212> TYPE: PRT
<213> ORGANISM: Homo sapiens
<220> FEATURE:
<221> NAME/KEY: SIGNAL
<222> LOCATION: (1)..(39)

<400> SEQUENCE: 1

Met Leu Pro Arg Val Gly Cys Pro Ala Leu Pro Leu Pro Pro Pro
1               5                   10                  15

Leu Leu Pro Leu Leu Pro Leu Leu Leu Leu Leu Gly Ala Ser Gly
                20                  25                  30

Gly Gly Gly Gly Ala Arg Ala Glu Val Leu Phe Arg Cys Pro Pro Cys
            35                  40                  45

Thr Pro Glu Arg Leu Ala Ala Cys Gly Pro Pro Val Ala Pro Pro
    50                  55                  60

Ala Ala Val Ala Ala Val Ala Gly Gly Ala Arg Met Pro Cys Ala Glu
```

```
                65                  70                  75                  80
Leu Val Arg Glu Pro Gly Cys Gly Cys Cys Ser Val Cys Ala Arg Leu
                    85                  90                  95
Glu Gly Glu Ala Cys Gly Val Tyr Thr Pro Arg Cys Gly Gln Gly Leu
                100                 105                 110
Arg Cys Tyr Pro His Pro Gly Ser Glu Leu Pro Leu Gln Ala Leu Val
                115                 120                 125
Met Gly Glu Gly Thr Cys Glu Lys Arg Arg Asp Ala Glu Tyr Gly Ala
            130                 135                 140
Ser Pro Glu Gln Val Ala Asp Asn Gly Asp His Ser Glu Gly Gly
145                 150                 155                 160
Leu Val Glu Asn His Val Asp Ser Thr Met Asn Met Leu Gly Gly Gly
                165                 170                 175
Gly Ser Ala Gly Arg Lys Pro Leu Lys Ser Gly Met Lys Glu Leu Ala
            180                 185                 190
Val Phe Arg Glu Lys Val Thr Glu Gln His Arg Gln Met Gly Lys Gly
            195                 200                 205
Gly Lys His His Leu Gly Leu Glu Glu Pro Lys Lys Leu Arg Pro Pro
        210                 215                 220
Pro Ala Arg Thr Pro Cys Gln Gln Glu Leu Asp Gln Val Leu Glu Arg
225                 230                 235                 240
Ile Ser Thr Met Arg Leu Pro Asp Glu Arg Gly Pro Leu Glu His Leu
                245                 250                 255
Tyr Ser Leu His Ile Pro Asn Cys Asp Lys His Gly Leu Tyr Asn Leu
                260                 265                 270
Lys Gln Cys Lys Met Ser Leu Asn Gly Gln Arg Gly Glu Cys Trp Cys
            275                 280                 285
Val Asn Pro Asn Thr Gly Lys Leu Ile Gln Gly Ala Pro Thr Ile Arg
            290                 295                 300
Gly Asp Pro Glu Cys His Leu Phe Tyr Asn Glu Gln Gln Glu Ala Arg
305                 310                 315                 320
Gly Val His Thr Gln Arg Met Gln
                325

<210> SEQ ID NO 2
<211> LENGTH: 289
<212> TYPE: PRT
<213> ORGANISM: Homo sapiens

<400> SEQUENCE: 2

Glu Val Leu Phe Arg Cys Pro Pro Cys Thr Pro Glu Arg Leu Ala Ala
1               5                   10                  15
Cys Gly Pro Pro Pro Val Ala Pro Pro Ala Ala Val Ala Ala Val Ala
            20                  25                  30
Gly Gly Ala Arg Met Pro Cys Ala Glu Leu Val Arg Glu Pro Gly Cys
        35                  40                  45
Gly Cys Cys Ser Val Cys Ala Arg Leu Glu Gly Glu Ala Cys Gly Val
    50                  55                  60
Tyr Thr Pro Arg Cys Gly Gln Gly Leu Arg Cys Tyr Pro His Pro Gly
65                  70                  75                  80
Ser Glu Leu Pro Leu Gln Ala Leu Val Met Gly Glu Gly Thr Cys Glu
                85                  90                  95
Lys Arg Arg Asp Ala Glu Tyr Gly Ala Ser Pro Glu Gln Val Ala Asp
                100                 105                 110
Asn Gly Asp Asp His Ser Glu Gly Gly Leu Val Glu Asn His Val Asp
```

```
                    115                 120                 125
Ser Thr Met Asn Met Leu Gly Gly Gly Ser Ala Gly Arg Lys Pro
    130                 135                 140
Leu Lys Ser Gly Met Lys Glu Leu Ala Val Phe Arg Glu Lys Val Thr
145                 150                 155                 160
Glu Gln His Arg Gln Met Gly Lys Gly Lys His His Leu Gly Leu
                165                 170                 175
Glu Glu Pro Lys Lys Leu Arg Pro Pro Ala Arg Thr Pro Cys Gln
            180                 185                 190
Gln Glu Leu Asp Gln Val Leu Glu Arg Ile Ser Thr Met Arg Leu Pro
        195                 200                 205
Asp Glu Arg Gly Pro Leu Glu His Leu Tyr Ser Leu His Ile Pro Asn
210                 215                 220
Cys Asp Lys His Gly Leu Tyr Asn Leu Lys Gln Cys Lys Met Ser Leu
225                 230                 235                 240
Asn Gly Gln Arg Gly Glu Cys Trp Cys Val Asn Pro Asn Thr Gly Lys
                245                 250                 255
Leu Ile Gln Gly Ala Pro Thr Ile Arg Gly Asp Pro Glu Cys His Leu
            260                 265                 270
Phe Tyr Asn Glu Gln Gln Glu Ala Arg Gly Val His Thr Gln Arg Met
        275                 280                 285
Gln

<210> SEQ ID NO 3
<211> LENGTH: 328
<212> TYPE: PRT
<213> ORGANISM: Homo sapiens
<220> FEATURE:
<221> NAME/KEY: SIGNAL
<222> LOCATION: (1)..(39)

<400> SEQUENCE: 3

Met Leu Pro Arg Val Gly Cys Pro Ala Leu Pro Leu Pro Pro Pro
1               5                   10                  15
Leu Leu Pro Leu Leu Pro Leu Leu Leu Leu Leu Gly Ala Ser Gly
            20                  25                  30
Gly Gly Gly Gly Ala Arg Ala Glu Val Leu Phe Arg Cys Pro Pro Cys
                35                  40                  45
Thr Pro Glu Arg Leu Ala Ala Cys Gly Pro Pro Pro Val Ala Pro Pro
    50                  55                  60
Ala Ala Val Ala Ala Val Ala Gly Ala Arg Met Pro Cys Ala Glu
65                  70                  75                  80
Leu Val Arg Glu Pro Gly Cys Gly Cys Cys Ser Val Cys Ala Arg Leu
                85                  90                  95
Glu Gly Glu Ala Cys Gly Val Tyr Thr Pro Arg Cys Gly Gln Gly Leu
            100                 105                 110
Arg Cys Tyr Pro His Pro Gly Ser Glu Leu Pro Leu Gln Ala Leu Val
        115                 120                 125
Met Gly Glu Gly Thr Cys Glu Lys Arg Arg Asp Ala Glu Tyr Gly Ala
    130                 135                 140
Ser Pro Glu Gln Val Ala Asp Asn Gly Asp Asp His Ser Glu Gly Gly
145                 150                 155                 160
Leu Val Glu Asn His Val Asp Ser Thr Met Asn Met Leu Gly Gly Gly
                165                 170                 175
Gly Ser Ala Gly Arg Lys Pro Leu Lys Ser Gly Met Lys Glu Leu Ala
            180                 185                 190
```

-continued

```
Val Phe Arg Glu Lys Val Thr Glu Gln His Arg Gln Met Gly Lys Gly
            195                 200                 205
Gly Lys His His Leu Gly Leu Glu Glu Pro Lys Lys Leu Arg Pro Pro
210                 215                 220
Pro Ala Arg Thr Pro Cys Gln Gln Glu Leu Asp Gln Val Leu Glu Arg
225                 230                 235                 240
Ile Ser Thr Met Arg Leu Pro Asp Glu Arg Gly Pro Leu Glu His Leu
            245                 250                 255
Tyr Ser Leu His Ile Pro Asn Cys Asp Lys His Gly Leu Tyr Asn Leu
            260                 265                 270
Lys Gln Cys Lys Met Ser Leu Asn Gly Gln Arg Gly Glu Cys Trp Cys
            275                 280                 285
Val Asn Pro Asn Thr Gly Lys Leu Ile Gln Gly Ala Pro Thr Ile Arg
            290                 295                 300
Gly Asp Pro Glu Cys His Leu Phe Tyr Asn Glu Gln Gln Glu Ala Arg
305                 310                 315                 320
Gly Val His Thr Gln Arg Met Gln
            325

<210> SEQ ID NO 4
<211> LENGTH: 289
<212> TYPE: PRT
<213> ORGANISM: Homo sapiens

<400> SEQUENCE: 4

Glu Val Leu Phe Arg Cys Pro Pro Cys Thr Pro Glu Arg Leu Ala Ala
1               5                   10                  15
Cys Gly Pro Pro Pro Val Ala Pro Pro Ala Ala Val Ala Ala Val Ala
            20                  25                  30
Gly Gly Ala Arg Met Pro Cys Ala Glu Leu Val Arg Glu Pro Gly Cys
            35                  40                  45
Gly Cys Cys Ser Val Cys Ala Arg Leu Glu Gly Glu Ala Cys Gly Val
        50                  55                  60
Tyr Thr Pro Arg Cys Gly Gln Gly Leu Arg Cys Tyr Pro His Pro Gly
65                  70                  75                  80
Ser Glu Leu Pro Leu Gln Ala Leu Val Met Gly Glu Gly Thr Cys Glu
            85                  90                  95
Lys Arg Arg Asp Ala Glu Tyr Gly Ala Ser Pro Glu Gln Val Ala Asp
            100                 105                 110
Asn Gly Asp Asp His Ser Glu Gly Gly Leu Val Glu Asn His Val Asp
        115                 120                 125
Ser Thr Met Asn Met Leu Gly Gly Gly Ser Ala Gly Arg Lys Pro
130                 135                 140
Leu Lys Ser Gly Met Lys Glu Leu Ala Val Phe Arg Glu Lys Val Thr
145                 150                 155                 160
Glu Gln His Arg Gln Met Gly Lys Gly Lys His His Leu Gly Leu
            165                 170                 175
Glu Glu Pro Lys Lys Leu Arg Pro Pro Ala Arg Thr Pro Cys Gln
            180                 185                 190
Gln Glu Leu Asp Gln Val Leu Glu Arg Ile Ser Thr Met Arg Leu Pro
            195                 200                 205
Asp Glu Arg Gly Pro Leu Glu His Leu Tyr Ser Leu His Ile Pro Asn
        210                 215                 220
Cys Asp Lys His Gly Leu Tyr Asn Leu Lys Gln Cys Lys Met Ser Leu
225                 230                 235                 240
```

```
Asn Gly Gln Arg Gly Glu Cys Trp Cys Val Asn Pro Asn Thr Gly Lys
                245                 250                 255

Leu Ile Gln Gly Ala Pro Thr Ile Arg Gly Asp Pro Glu Cys His Leu
                260                 265                 270

Phe Tyr Asn Glu Gln Glu Ala Arg Gly Val His Thr Gln Arg Met
            275                 280                 285

Gln

<210> SEQ ID NO 5
<211> LENGTH: 328
<212> TYPE: PRT
<213> ORGANISM: Homo sapiens
<220> FEATURE:
<221> NAME/KEY: SIGNAL
<222> LOCATION: (1)..(39)

<400> SEQUENCE: 5

Met Leu Pro Arg Val Gly Cys Pro Ala Leu Pro Leu Pro Pro Pro Pro
1               5                   10                  15

Leu Leu Pro Leu Leu Pro Leu Leu Leu Leu Leu Gly Ala Ser Gly
                20                  25                  30

Gly Gly Gly Gly Ala Arg Ala Glu Val Leu Phe Arg Cys Pro Pro Cys
                35                  40                  45

Thr Pro Glu Arg Leu Ala Ala Cys Gly Pro Pro Val Ala Pro Pro
    50                  55                  60

Ala Ala Val Ala Ala Val Ala Gly Gly Ala Arg Met Pro Cys Ala Glu
65                  70                  75                  80

Leu Val Arg Glu Pro Gly Cys Gly Cys Cys Ser Val Cys Ala Arg Leu
                85                  90                  95

Glu Gly Glu Ala Cys Gly Val Tyr Thr Pro Arg Cys Gly Gln Gly Leu
                100                 105                 110

Arg Cys Tyr Pro His Pro Gly Ser Glu Leu Pro Leu Gln Ala Leu Val
                115                 120                 125

Met Gly Glu Gly Thr Cys Glu Lys Arg Arg Asp Ala Glu Tyr Gly Ala
    130                 135                 140

Ser Pro Glu Gln Val Ala Asp Asn Gly Asp Asp His Ser Glu Gly Gly
145                 150                 155                 160

Leu Val Glu Asn His Val Asp Ser Thr Met Asn Met Leu Gly Gly Gly
                165                 170                 175

Gly Ser Ala Gly Arg Lys Pro Leu Lys Ser Gly Met Lys Glu Leu Ala
                180                 185                 190

Val Phe Arg Glu Lys Val Thr Glu Gln His Arg Gln Met Gly Lys Gly
                195                 200                 205

Gly Lys His His Leu Gly Leu Glu Glu Pro Lys Lys Leu Arg Pro Pro
    210                 215                 220

Pro Ala Arg Thr Pro Cys Gln Gln Glu Leu Asp Gln Val Leu Glu Arg
225                 230                 235                 240

Ile Ser Thr Met Arg Leu Pro Asp Glu Arg Gly Pro Leu Glu His Leu
                245                 250                 255

Tyr Ser Leu His Ile Pro Asn Cys Asp Lys His Gly Leu Tyr Asn Leu
                260                 265                 270

Lys Gln Cys Lys Met Ser Leu Asn Gly Gln Arg Gly Glu Cys Trp Cys
                275                 280                 285

Val Asn Pro Asn Thr Gly Lys Leu Ile Gln Gly Ala Pro Thr Ile Arg
    290                 295                 300
```

-continued

```
Gly Asp Pro Glu Cys His Leu Phe Tyr Asn Glu Gln Glu Ala Arg
305                 310                 315                 320

Gly Val His Thr Gln Arg Met Gln
            325
```

<210> SEQ ID NO 6
<211> LENGTH: 289
<212> TYPE: PRT
<213> ORGANISM: Homo sapiens

<400> SEQUENCE: 6

```
Glu Val Leu Phe Arg Cys Pro Pro Cys Thr Pro Glu Arg Leu Ala Ala
1               5                   10                  15

Cys Gly Pro Pro Pro Val Ala Pro Pro Ala Ala Val Ala Ala Val Ala
            20                  25                  30

Gly Gly Ala Arg Met Pro Cys Ala Glu Leu Val Arg Glu Pro Gly Cys
        35                  40                  45

Gly Cys Cys Ser Val Cys Ala Arg Leu Glu Gly Glu Ala Cys Gly Val
    50                  55                  60

Tyr Thr Pro Arg Cys Gly Gln Gly Leu Arg Cys Tyr Pro His Pro Gly
65                  70                  75                  80

Ser Glu Leu Pro Leu Gln Ala Leu Val Met Gly Glu Gly Thr Cys Glu
                85                  90                  95

Lys Arg Arg Asp Ala Glu Tyr Gly Ala Ser Pro Glu Gln Val Ala Asp
            100                 105                 110

Asn Gly Asp Asp His Ser Glu Gly Gly Leu Val Glu Asn His Val Asp
        115                 120                 125

Ser Thr Met Asn Met Leu Gly Gly Gly Gly Ser Ala Gly Arg Lys Pro
    130                 135                 140

Leu Lys Ser Gly Met Lys Glu Leu Ala Val Phe Arg Glu Lys Val Thr
145                 150                 155                 160

Glu Gln His Arg Gln Met Gly Lys Gly Gly Lys His His Leu Gly Leu
                165                 170                 175

Glu Glu Pro Lys Lys Leu Arg Pro Pro Pro Ala Arg Thr Pro Cys Gln
            180                 185                 190

Gln Glu Leu Asp Gln Val Leu Glu Arg Ile Ser Thr Met Arg Leu Pro
        195                 200                 205

Asp Glu Arg Gly Pro Leu Glu His Leu Tyr Ser Leu His Ile Pro Asn
    210                 215                 220

Cys Asp Lys His Gly Leu Tyr Asn Leu Lys Gln Cys Lys Met Ser Leu
225                 230                 235                 240

Asn Gly Gln Arg Gly Glu Cys Trp Cys Val Asn Pro Asn Thr Gly Lys
                245                 250                 255

Leu Ile Gln Gly Ala Pro Thr Ile Arg Gly Asp Pro Glu Cys His Leu
            260                 265                 270

Phe Tyr Asn Glu Gln Glu Ala Arg Gly Val His Thr Gln Arg Met
        275                 280                 285

Gln
```

<210> SEQ ID NO 7
<211> LENGTH: 328
<212> TYPE: PRT
<213> ORGANISM: Homo sapiens
<220> FEATURE:
<221> NAME/KEY: SIGNAL
<222> LOCATION: (1)..(39)

<400> SEQUENCE: 7

```
Met Leu Pro Arg Val Gly Cys Pro Ala Leu Pro Leu Pro Pro Pro
1               5                   10                  15

Leu Leu Pro Leu Leu Pro Leu Leu Leu Leu Leu Gly Ala Ser Gly
            20                  25                  30

Gly Gly Gly Gly Ala Arg Ala Glu Val Leu Phe Arg Cys Pro Cys
            35                  40                  45

Thr Pro Glu Arg Leu Ala Ala Cys Gly Pro Pro Val Ala Pro Pro
50                  55                  60

Ala Ala Val Ala Ala Val Ala Gly Gly Ala Arg Met Pro Cys Ala Glu
65                  70                  75                  80

Leu Val Arg Glu Pro Gly Cys Gly Cys Cys Ser Val Cys Ala Arg Leu
                85                  90                  95

Glu Gly Glu Ala Cys Gly Val Tyr Thr Pro Arg Cys Gly Gln Gly Leu
                100                 105                 110

Arg Cys Tyr Pro His Pro Gly Ser Glu Leu Pro Leu Gln Ala Leu Val
            115                 120                 125

Met Gly Glu Gly Thr Cys Glu Lys Arg Arg Asp Ala Glu Tyr Gly Ala
130                 135                 140

Ser Pro Glu Gln Val Ala Asp Asn Gly Asp Asp His Ser Glu Gly Gly
145                 150                 155                 160

Leu Val Glu Asn His Val Asp Ser Thr Met Asn Met Leu Gly Gly Gly
                165                 170                 175

Gly Ser Ala Gly Arg Lys Pro Leu Lys Ser Gly Met Lys Glu Leu Ala
            180                 185                 190

Val Phe Arg Glu Lys Val Thr Glu Gln His Arg Gln Met Gly Lys Gly
            195                 200                 205

Gly Lys His His Leu Gly Leu Glu Glu Pro Lys Lys Leu Arg Pro Pro
        210                 215                 220

Pro Ala Arg Thr Pro Cys Gln Gln Glu Leu Asp Gln Val Leu Glu Arg
225                 230                 235                 240

Ile Ser Thr Met Arg Leu Pro Asp Glu Arg Gly Pro Leu Glu His Leu
                245                 250                 255

Tyr Ser Leu His Ile Pro Asn Cys Asp Lys His Gly Leu Tyr Asn Leu
            260                 265                 270

Lys Gln Cys Lys Met Ser Leu Asn Gly Gln Arg Gly Glu Cys Trp Cys
            275                 280                 285

Val Asn Pro Asn Thr Gly Lys Leu Ile Gln Gly Ala Pro Thr Ile Arg
            290                 295                 300

Gly Asp Pro Glu Cys His Leu Phe Tyr Asn Glu Gln Gln Glu Ala Arg
305                 310                 315                 320

Gly Val His Thr Gln Arg Met Gln
                325

<210> SEQ ID NO 8
<211> LENGTH: 289
<212> TYPE: PRT
<213> ORGANISM: Homo sapiens

<400> SEQUENCE: 8

Glu Val Leu Phe Arg Cys Pro Pro Cys Thr Pro Glu Arg Leu Ala Ala
1               5                   10                  15

Cys Gly Pro Pro Pro Val Ala Pro Pro Ala Ala Val Ala Ala Val Ala
            20                  25                  30

Gly Gly Ala Arg Met Pro Cys Ala Glu Leu Val Arg Glu Pro Gly Cys
            35                  40                  45
```

-continued

Gly Cys Cys Ser Val Cys Ala Arg Leu Glu Gly Glu Ala Cys Gly Val
 50                  55                  60

Tyr Thr Pro Arg Cys Gly Gln Gly Leu Arg Cys Tyr Pro His Pro Gly
65                   70                  75                  80

Ser Glu Leu Pro Leu Gln Ala Leu Val Met Gly Glu Gly Thr Cys Glu
                 85                  90                  95

Lys Arg Arg Asp Ala Glu Tyr Gly Ala Ser Pro Glu Gln Val Ala Asp
             100                 105                 110

Asn Gly Asp Asp His Ser Glu Gly Leu Val Glu Asn His Val Asp
         115                 120                 125

Ser Thr Met Asn Met Leu Gly Gly Gly Ser Ala Gly Arg Lys Pro
130                 135                 140

Leu Lys Ser Gly Met Lys Glu Leu Ala Val Phe Arg Glu Lys Val Thr
145                 150                 155                 160

Glu Gln His Arg Gln Met Gly Lys Gly Lys His His Leu Gly Leu
                 165                 170                 175

Glu Glu Pro Lys Lys Leu Arg Pro Pro Ala Arg Thr Pro Cys Gln
             180                 185                 190

Gln Glu Leu Asp Gln Val Leu Glu Arg Ile Ser Thr Met Arg Leu Pro
             195                 200                 205

Asp Glu Arg Gly Pro Leu Glu His Leu Tyr Ser Leu His Ile Pro Asn
210                 215                 220

Cys Asp Lys His Gly Leu Tyr Asn Leu Lys Gln Cys Lys Met Ser Leu
225                 230                 235                 240

Asn Gly Gln Arg Gly Glu Cys Trp Cys Val Asn Pro Asn Thr Gly Lys
                 245                 250                 255

Leu Ile Gln Gly Ala Pro Thr Ile Arg Gly Asp Pro Glu Cys His Leu
             260                 265                 270

Phe Tyr Asn Glu Gln Gln Glu Ala Arg Gly Val His Thr Gln Arg Met
             275                 280                 285
Gln

<210> SEQ ID NO 9
<211> LENGTH: 328
<212> TYPE: PRT
<213> ORGANISM: Homo sapiens
<220> FEATURE:
<221> NAME/KEY: SIGNAL
<222> LOCATION: (1)..(39)

<400> SEQUENCE: 9

Met Leu Pro Arg Val Gly Cys Pro Ala Leu Pro Leu Pro Pro Pro Pro
1               5                   10                  15

Leu Leu Pro Leu Leu Pro Leu Leu Leu Leu Leu Gly Ala Ser Gly
                 20                  25                  30

Gly Gly Gly Gly Ala Arg Ala Glu Val Leu Phe Arg Cys Pro Pro Cys
             35                  40                  45

Thr Pro Glu Arg Leu Ala Ala Cys Gly Pro Pro Val Ala Pro Pro
 50                  55                  60

Ala Ala Val Ala Ala Val Ala Gly Gly Ala Arg Met Pro Cys Ala Glu
65                  70                  75                  80

Leu Val Arg Glu Pro Gly Cys Gly Cys Cys Ser Val Cys Ala Arg Leu
                 85                  90                  95

Glu Gly Glu Ala Cys Gly Val Tyr Thr Pro Arg Cys Gly Gln Gly Leu
             100                 105                 110

-continued

```
Arg Cys Tyr Pro His Pro Gly Ser Glu Leu Pro Leu Gln Ala Leu Val
            115                 120                 125

Met Gly Glu Gly Thr Cys Glu Lys Arg Arg Asp Ala Glu Tyr Gly Ala
130                 135                 140

Ser Pro Glu Gln Val Ala Asp Asn Gly Asp His Ser Glu Gly Gly
145                 150                 155                 160

Leu Val Glu Asn His Val Asp Ser Thr Met Asn Met Leu Gly Gly Gly
                165                 170                 175

Gly Ser Ala Gly Arg Lys Pro Leu Lys Ser Gly Met Lys Glu Leu Ala
            180                 185                 190

Val Phe Arg Glu Lys Val Thr Glu Gln His Arg Gln Met Gly Lys Gly
        195                 200                 205

Gly Lys His His Leu Gly Leu Glu Glu Pro Lys Lys Leu Arg Pro Pro
    210                 215                 220

Pro Ala Arg Thr Pro Cys Gln Gln Glu Leu Asp Gln Val Leu Glu Arg
225                 230                 235                 240

Ile Ser Thr Met Arg Leu Pro Asp Glu Arg Gly Pro Leu Glu His Leu
                245                 250                 255

Tyr Ser Leu His Ile Pro Asn Cys Asp Lys His Gly Leu Tyr Asn Leu
            260                 265                 270

Lys Gln Cys Lys Met Ser Leu Asn Gly Gln Arg Gly Glu Cys Trp Cys
        275                 280                 285

Val Asn Pro Asn Thr Gly Lys Leu Ile Gln Gly Ala Pro Thr Ile Arg
    290                 295                 300

Gly Asp Pro Glu Cys His Leu Phe Tyr Asn Glu Gln Gln Glu Ala Arg
305                 310                 315                 320

Gly Val His Thr Gln Arg Met Gln
                325

<210> SEQ ID NO 10
<211> LENGTH: 289
<212> TYPE: PRT
<213> ORGANISM: Homo sapiens

<400> SEQUENCE: 10

Glu Val Leu Phe Arg Cys Pro Pro Cys Thr Pro Glu Arg Leu Ala Ala
1               5                   10                  15

Cys Gly Pro Pro Pro Val Ala Pro Pro Ala Ala Val Ala Val Ala
                20                  25                  30

Gly Gly Ala Arg Met Pro Cys Ala Glu Leu Val Arg Glu Pro Gly Cys
            35                  40                  45

Gly Cys Cys Ser Val Cys Ala Arg Leu Glu Gly Glu Ala Cys Gly Val
        50                  55                  60

Tyr Thr Pro Arg Cys Gly Gln Gly Leu Arg Cys Tyr Pro His Pro Gly
65                  70                  75                  80

Ser Glu Leu Pro Leu Gln Ala Leu Val Met Gly Glu Gly Thr Cys Glu
                85                  90                  95

Lys Arg Arg Asp Ala Glu Tyr Gly Ala Ser Pro Glu Gln Val Ala Asp
            100                 105                 110

Asn Gly Asp Asp His Ser Glu Gly Gly Leu Val Glu Asn His Val Asp
        115                 120                 125

Ser Thr Met Asn Met Leu Gly Gly Gly Ser Ala Gly Arg Lys Pro
    130                 135                 140

Leu Lys Ser Gly Met Lys Glu Leu Ala Val Phe Arg Glu Lys Val Thr
145                 150                 155                 160
```

-continued

```
Glu Gln His Arg Gln Met Gly Lys Gly Gly Lys His Leu Gly Leu
            165                 170                 175
Glu Glu Pro Lys Lys Leu Arg Pro Pro Ala Arg Thr Pro Cys Gln
            180                 185                 190
Gln Glu Leu Asp Gln Val Leu Glu Arg Ile Ser Thr Met Arg Leu Pro
            195                 200                 205
Asp Glu Arg Gly Pro Leu Glu His Leu Tyr Ser Leu His Ile Pro Asn
210                 215                 220
Cys Asp Lys His Gly Leu Tyr Asn Leu Lys Gln Cys Lys Met Ser Leu
225                 230                 235                 240
Asn Gly Gln Arg Gly Glu Cys Trp Cys Val Asn Pro Asn Thr Gly Lys
            245                 250                 255
Leu Ile Gln Gly Ala Pro Thr Ile Arg Gly Asp Pro Glu Cys His Leu
            260                 265                 270
Phe Tyr Asn Glu Gln Gln Glu Ala Arg Gly Val His Thr Gln Arg Met
            275                 280                 285
Gln

<210> SEQ ID NO 11
<211> LENGTH: 328
<212> TYPE: PRT
<213> ORGANISM: Homo sapiens
<220> FEATURE:
<221> NAME/KEY: SIGNAL
<222> LOCATION: (1)..(39)

<400> SEQUENCE: 11

Met Leu Pro Arg Val Gly Cys Pro Ala Leu Pro Leu Pro Pro Pro Pro
1               5                   10                  15
Leu Leu Pro Leu Leu Pro Leu Leu Leu Leu Leu Leu Gly Ala Ser Gly
            20                  25                  30
Gly Gly Gly Gly Ala Arg Ala Glu Val Leu Phe Arg Cys Pro Pro Cys
            35                  40                  45
Thr Pro Glu Arg Leu Ala Ala Cys Gly Pro Pro Pro Val Ala Pro Pro
        50                  55                  60
Ala Ala Val Ala Ala Val Ala Gly Gly Ala Arg Met Pro Cys Ala Glu
65                  70                  75                  80
Leu Val Arg Glu Pro Gly Cys Gly Cys Cys Ser Val Cys Ala Arg Leu
                85                  90                  95
Glu Gly Glu Ala Cys Gly Val Tyr Thr Pro Arg Cys Gly Gln Gly Leu
            100                 105                 110
Arg Cys Tyr Pro His Pro Gly Ser Glu Leu Pro Leu Gln Ala Leu Val
        115                 120                 125
Met Gly Glu Gly Thr Cys Glu Lys Arg Arg Asp Ala Glu Tyr Gly Ala
    130                 135                 140
Ser Pro Glu Gln Val Ala Asp Asn Gly Asp Asp His Ser Glu Gly Gly
145                 150                 155                 160
Leu Val Glu Asn His Val Asp Ser Thr Met Asn Met Leu Gly Gly Gly
                165                 170                 175
Gly Ser Ala Gly Arg Lys Pro Leu Lys Ser Gly Met Lys Glu Leu Ala
            180                 185                 190
Val Phe Arg Glu Lys Val Thr Glu Gln His Arg Gln Met Gly Lys Gly
        195                 200                 205
Gly Lys His His Leu Gly Leu Glu Glu Pro Lys Lys Leu Arg Pro Pro
    210                 215                 220
Pro Ala Arg Thr Pro Cys Gln Gln Glu Leu Asp Gln Val Leu Glu Arg
```

```
                225                 230                 235                 240
Ile Ser Thr Met Arg Leu Pro Asp Glu Arg Gly Pro Leu Glu His Leu
                    245                 250                 255

Tyr Ser Leu His Ile Pro Asn Cys Asp Lys His Gly Leu Tyr Asn Leu
                260                 265                 270

Lys Gln Cys Lys Met Ser Leu Asn Gly Gln Arg Gly Glu Cys Trp Cys
            275                 280                 285

Val Asn Pro Asn Thr Gly Lys Leu Ile Gln Gly Ala Pro Thr Ile Arg
        290                 295                 300

Gly Asp Pro Glu Cys His Leu Phe Tyr Asn Glu Gln Gln Glu Ala Arg
305                 310                 315                 320

Gly Val His Thr Gln Arg Met Gln
                325

<210> SEQ ID NO 12
<211> LENGTH: 289
<212> TYPE: PRT
<213> ORGANISM: Homo sapiens

<400> SEQUENCE: 12

Glu Val Leu Phe Arg Cys Pro Pro Cys Thr Pro Glu Arg Leu Ala Ala
1               5                   10                  15

Cys Gly Pro Pro Pro Val Ala Pro Pro Ala Ala Val Ala Ala Val Ala
            20                  25                  30

Gly Gly Ala Arg Met Pro Cys Ala Glu Leu Val Arg Glu Pro Gly Cys
        35                  40                  45

Gly Cys Cys Ser Val Cys Ala Arg Leu Glu Gly Glu Ala Cys Gly Val
    50                  55                  60

Tyr Thr Pro Arg Cys Gly Gln Gly Leu Arg Cys Tyr Pro His Pro Gly
65                  70                  75                  80

Ser Glu Leu Pro Leu Gln Ala Leu Val Met Gly Glu Gly Thr Cys Glu
                85                  90                  95

Lys Arg Arg Asp Ala Glu Tyr Gly Ala Ser Pro Glu Gln Val Ala Asp
            100                 105                 110

Asn Gly Asp Asp His Ser Glu Gly Gly Leu Val Glu Asn His Val Asp
        115                 120                 125

Ser Thr Met Asn Met Leu Gly Gly Gly Ser Ala Gly Arg Lys Pro
    130                 135                 140

Leu Lys Ser Gly Met Lys Glu Leu Ala Val Phe Arg Glu Lys Val Thr
145                 150                 155                 160

Glu Gln His Arg Gln Met Gly Lys Gly Lys His His Leu Gly Leu
                165                 170                 175

Glu Glu Pro Lys Lys Leu Arg Pro Pro Ala Arg Thr Pro Cys Gln
            180                 185                 190

Gln Glu Leu Asp Gln Val Leu Glu Arg Ile Ser Thr Met Arg Leu Pro
        195                 200                 205

Asp Glu Arg Gly Pro Leu Glu His Leu Tyr Ser Leu His Ile Pro Asn
    210                 215                 220

Cys Asp Lys His Gly Leu Tyr Asn Leu Lys Gln Cys Lys Met Ser Leu
225                 230                 235                 240

Asn Gly Gln Arg Gly Glu Cys Trp Cys Val Asn Pro Asn Thr Gly Lys
                245                 250                 255

Leu Ile Gln Gly Ala Pro Thr Ile Arg Gly Asp Pro Glu Cys His Leu
            260                 265                 270

Phe Tyr Asn Glu Gln Gln Glu Ala Arg Gly Val His Thr Gln Arg Met
```

-continued

```
                275                 280                 285

Gln

<210> SEQ ID NO 13
<211> LENGTH: 328
<212> TYPE: PRT
<213> ORGANISM: Homo sapiens
<220> FEATURE:
<221> NAME/KEY: SIGNAL
<222> LOCATION: (1)..(39)

<400> SEQUENCE: 13

Met Leu Pro Arg Val Gly Cys Pro Ala Leu Pro Leu Pro Pro Pro Pro
1               5                   10                  15

Leu Leu Pro Leu Leu Pro Leu Leu Leu Leu Leu Leu Gly Ala Ser Gly
            20                  25                  30

Gly Gly Gly Gly Ala Arg Ala Glu Val Leu Phe Arg Cys Pro Pro Cys
        35                  40                  45

Thr Pro Glu Arg Leu Ala Ala Cys Gly Pro Pro Pro Val Ala Pro Pro
    50                  55                  60

Ala Ala Val Ala Val Ala Gly Gly Ala Arg Met Pro Cys Ala Glu
65                  70                  75                  80

Leu Val Arg Glu Pro Gly Cys Gly Cys Cys Ser Val Cys Ala Arg Leu
                85                  90                  95

Glu Gly Glu Ala Cys Gly Val Tyr Thr Pro Arg Cys Gly Gln Gly Leu
            100                 105                 110

Arg Cys Tyr Pro His Pro Gly Ser Glu Leu Pro Leu Gln Ala Leu Val
        115                 120                 125

Met Gly Glu Gly Thr Cys Glu Lys Arg Arg Asp Ala Glu Tyr Gly Ala
130                 135                 140

Ser Pro Glu Gln Val Ala Asp Asn Gly Asp Asp His Ser Glu Gly Gly
145                 150                 155                 160

Leu Val Glu Asn His Val Asp Ser Thr Met Asn Met Leu Gly Gly Gly
                165                 170                 175

Gly Ser Ala Gly Arg Lys Pro Leu Lys Ser Gly Met Lys Glu Leu Ala
            180                 185                 190

Val Phe Arg Glu Lys Val Thr Glu Gln His Arg Gln Met Gly Lys Gly
        195                 200                 205

Gly Lys His His Leu Gly Leu Glu Glu Pro Lys Lys Leu Arg Pro Pro
    210                 215                 220

Pro Ala Arg Thr Pro Cys Gln Gln Glu Leu Asp Gln Val Leu Glu Arg
225                 230                 235                 240

Ile Ser Thr Met Arg Leu Pro Asp Glu Arg Gly Pro Leu Glu His Leu
                245                 250                 255

Tyr Ser Leu His Ile Pro Asn Cys Asp Lys His Gly Leu Tyr Asn Leu
            260                 265                 270

Lys Gln Cys Lys Met Ser Leu Asn Gly Gln Arg Gly Glu Cys Trp Cys
        275                 280                 285

Val Asn Pro Asn Thr Gly Lys Leu Ile Gln Gly Ala Pro Thr Ile Arg
    290                 295                 300

Gly Asp Pro Glu Cys His Leu Phe Tyr Asn Glu Gln Glu Ala Arg
305                 310                 315                 320

Gly Val His Thr Gln Arg Met Gln
            325

<210> SEQ ID NO 14
```

```
<211> LENGTH: 289
<212> TYPE: PRT
<213> ORGANISM: Homo sapiens

<400> SEQUENCE: 14

Glu Val Leu Phe Arg Cys Pro Pro Cys Thr Pro Glu Arg Leu Ala Ala
1               5                   10                  15

Cys Gly Pro Pro Pro Val Ala Pro Ala Ala Val Ala Ala Val Ala
            20                  25                  30

Gly Gly Ala Arg Met Pro Cys Ala Glu Leu Val Arg Glu Pro Gly Cys
        35                  40                  45

Gly Cys Cys Ser Val Cys Ala Arg Leu Glu Gly Glu Ala Cys Gly Val
    50                  55                  60

Tyr Thr Pro Arg Cys Gly Gln Gly Leu Arg Cys Tyr Pro His Pro Gly
65                  70                  75                  80

Ser Glu Leu Pro Leu Gln Ala Leu Val Met Gly Glu Gly Thr Cys Glu
                85                  90                  95

Lys Arg Arg Asp Ala Glu Tyr Gly Ala Ser Pro Glu Gln Val Ala Asp
            100                 105                 110

Asn Gly Asp Asp His Ser Glu Gly Leu Val Glu Asn His Val Asp
        115                 120                 125

Ser Thr Met Asn Met Leu Gly Gly Gly Ser Ala Gly Arg Lys Pro
    130                 135                 140

Leu Lys Ser Gly Met Lys Glu Leu Ala Val Phe Arg Glu Lys Val Thr
145                 150                 155                 160

Glu Gln His Arg Gln Met Gly Lys Gly Lys His His Leu Gly Leu
                165                 170                 175

Glu Glu Pro Lys Lys Leu Arg Pro Pro Ala Arg Thr Pro Cys Gln
            180                 185                 190

Gln Glu Leu Asp Gln Val Leu Glu Arg Ile Ser Thr Met Arg Leu Pro
        195                 200                 205

Asp Glu Arg Gly Pro Leu Glu His Leu Tyr Ser Leu His Ile Pro Asn
    210                 215                 220

Cys Asp Lys His Gly Leu Tyr Asn Leu Lys Gln Cys Lys Met Ser Leu
225                 230                 235                 240

Asn Gly Gln Arg Gly Glu Cys Trp Cys Val Asn Pro Asn Thr Gly Lys
                245                 250                 255

Leu Ile Gln Gly Ala Pro Thr Ile Arg Gly Asp Pro Glu Cys His Leu
            260                 265                 270

Phe Tyr Asn Glu Gln Glu Ala Arg Gly Val His Thr Gln Arg Met
        275                 280                 285

Gln

<210> SEQ ID NO 15
<211> LENGTH: 328
<212> TYPE: PRT
<213> ORGANISM: Homo sapiens
<220> FEATURE:
<221> NAME/KEY: SIGNAL
<222> LOCATION: (1)..(39)

<400> SEQUENCE: 15

Met Leu Pro Arg Val Gly Cys Pro Ala Leu Pro Leu Pro Pro Pro Pro
1               5                   10                  15

Leu Leu Pro Leu Leu Pro Leu Leu Leu Leu Leu Gly Ala Ser Gly
            20                  25                  30

Gly Gly Gly Gly Ala Arg Ala Glu Val Leu Phe Arg Cys Pro Pro Cys
```

```
                 35                  40                  45
Thr Pro Glu Arg Leu Ala Ala Cys Gly Pro Pro Val Ala Pro Pro
 50                  55                  60

Ala Ala Val Ala Val Ala Gly Gly Ala Arg Met Pro Cys Ala Glu
 65                  70                  75                  80

Leu Val Arg Glu Pro Gly Cys Gly Cys Ser Val Cys Ala Arg Leu
                 85                  90                  95

Glu Gly Glu Ala Cys Gly Val Tyr Thr Pro Arg Cys Gly Gln Leu
                100                 105                 110

Arg Cys Tyr Pro His Pro Gly Ser Glu Leu Pro Leu Gln Ala Leu Val
                115                 120                 125

Met Gly Glu Gly Thr Cys Glu Lys Arg Arg Asp Ala Glu Tyr Gly Ala
                130                 135                 140

Ser Pro Glu Gln Val Ala Asp Asn Gly Asp Asp His Ser Glu Gly Gly
145                 150                 155                 160

Leu Val Glu Asn His Val Asp Ser Thr Met Asn Met Leu Gly Gly Gly
                165                 170                 175

Gly Ser Ala Gly Arg Lys Pro Leu Lys Ser Gly Met Lys Glu Leu Ala
                180                 185                 190

Val Phe Arg Glu Lys Val Thr Glu Gln His Arg Gln Met Gly Lys Gly
                195                 200                 205

Gly Lys His His Leu Gly Leu Glu Glu Pro Lys Lys Leu Arg Pro Pro
                210                 215                 220

Pro Ala Arg Thr Pro Cys Gln Gln Glu Leu Asp Gln Val Leu Glu Arg
225                 230                 235                 240

Ile Ser Thr Met Arg Leu Pro Asp Glu Arg Gly Pro Leu Glu His Leu
                245                 250                 255

Tyr Ser Leu His Ile Pro Asn Cys Asp Lys His Gly Leu Tyr Asn Leu
                260                 265                 270

Lys Gln Cys Lys Met Ser Leu Asn Gly Gln Arg Gly Glu Cys Trp Cys
                275                 280                 285

Val Asn Pro Asn Thr Gly Lys Leu Ile Gln Gly Ala Pro Thr Ile Arg
290                 295                 300

Gly Asp Pro Glu Cys His Leu Phe Tyr Asn Glu Gln Gln Glu Ala Arg
305                 310                 315                 320

Gly Val His Thr Gln Arg Met Gln
                325

<210> SEQ ID NO 16
<211> LENGTH: 289
<212> TYPE: PRT
<213> ORGANISM: Homo sapiens

<400> SEQUENCE: 16

Glu Val Leu Phe Arg Cys Pro Pro Cys Thr Pro Glu Arg Leu Ala Ala
 1               5                  10                  15

Cys Gly Pro Pro Pro Val Ala Pro Pro Ala Ala Val Ala Ala Val Ala
                20                  25                  30

Gly Gly Ala Arg Met Pro Cys Ala Glu Leu Val Arg Glu Pro Gly Cys
                35                  40                  45

Gly Cys Cys Ser Val Cys Ala Arg Leu Glu Gly Glu Ala Cys Gly Val
                50                  55                  60

Tyr Thr Pro Arg Cys Gly Gln Gly Leu Arg Cys Tyr Pro His Pro Gly
 65              70                  75                  80

Ser Glu Leu Pro Leu Gln Ala Leu Val Met Gly Glu Gly Thr Cys Glu
```

```
                85                  90                  95
Lys Arg Arg Asp Ala Glu Tyr Gly Ala Ser Pro Glu Gln Val Ala Asp
            100                 105                 110

Asn Gly Asp Asp His Ser Glu Gly Gly Leu Val Glu Asn His Val Asp
            115                 120                 125

Ser Thr Met Asn Met Leu Gly Gly Gly Ser Ala Gly Arg Lys Pro
130                 135                 140

Leu Lys Ser Gly Met Lys Glu Leu Ala Val Phe Arg Glu Lys Val Thr
145                 150                 155                 160

Glu Gln His Arg Gln Met Gly Lys Gly Lys His His Leu Gly Leu
                165                 170                 175

Glu Glu Pro Lys Lys Leu Arg Pro Pro Ala Arg Thr Pro Cys Gln
            180                 185                 190

Gln Glu Leu Asp Gln Val Leu Glu Arg Ile Ser Thr Met Arg Leu Pro
            195                 200                 205

Asp Glu Arg Gly Pro Leu Glu His Leu Tyr Ser Leu His Ile Pro Asn
            210                 215                 220

Cys Asp Lys His Gly Leu Tyr Asn Leu Lys Gln Cys Lys Met Ser Leu
225                 230                 235                 240

Asn Gly Gln Arg Gly Glu Cys Trp Cys Val Asn Pro Asn Thr Gly Lys
                245                 250                 255

Leu Ile Gln Gly Ala Pro Thr Ile Arg Gly Asp Pro Glu Cys His Leu
            260                 265                 270

Phe Tyr Asn Glu Gln Gln Glu Ala Arg Gly Val His Thr Gln Arg Met
            275                 280                 285

Gln

<210> SEQ ID NO 17
<211> LENGTH: 328
<212> TYPE: PRT
<213> ORGANISM: Homo sapiens
<220> FEATURE:
<221> NAME/KEY: SIGNAL
<222> LOCATION: (1)..(39)

<400> SEQUENCE: 17

Met Leu Pro Arg Val Gly Cys Pro Ala Leu Pro Leu Pro Pro Pro Pro
1               5                   10                  15

Leu Leu Pro Leu Leu Pro Leu Leu Leu Leu Leu Gly Ala Ser Gly
            20                  25                  30

Gly Gly Gly Gly Ala Arg Ala Glu Val Leu Phe Arg Cys Pro Pro Cys
            35                  40                  45

Thr Pro Glu Arg Leu Ala Ala Cys Gly Pro Pro Val Ala Pro Pro
50                  55                  60

Ala Ala Val Ala Ala Val Ala Gly Gly Ala Arg Met Pro Cys Ala Glu
65                  70                  75                  80

Leu Val Arg Glu Pro Gly Cys Gly Cys Cys Ser Val Cys Ala Arg Leu
                85                  90                  95

Glu Gly Glu Ala Cys Gly Val Tyr Thr Pro Arg Cys Gly Gln Gly Leu
            100                 105                 110

Arg Cys Tyr Pro His Pro Gly Ser Glu Leu Pro Leu Gln Ala Leu Val
            115                 120                 125

Met Gly Glu Gly Thr Cys Glu Lys Arg Arg Asp Ala Glu Tyr Gly Ala
130                 135                 140

Ser Pro Glu Gln Val Ala Asp Asn Gly Asp Asp His Ser Glu Gly Gly
145                 150                 155                 160
```

```
Leu Val Glu Asn His Val Asp Ser Thr Met Asn Met Leu Gly Gly
            165                 170                 175

Gly Ser Ala Gly Arg Lys Pro Leu Lys Ser Gly Met Lys Glu Leu Ala
        180                 185                 190

Val Phe Arg Glu Lys Val Thr Glu Gln His Arg Gln Met Gly Lys Gly
            195                 200                 205

Gly Lys His His Leu Gly Leu Glu Glu Pro Lys Lys Leu Arg Pro Pro
    210                 215                 220

Pro Ala Arg Thr Pro Cys Gln Gln Glu Leu Asp Gln Val Leu Glu Arg
225                 230                 235                 240

Ile Ser Thr Met Arg Leu Pro Asp Glu Arg Gly Pro Leu Glu His Leu
                245                 250                 255

Tyr Ser Leu His Ile Pro Asn Cys Asp Lys His Gly Leu Tyr Asn Leu
                260                 265                 270

Lys Gln Cys Lys Met Ser Leu Asn Gly Gln Arg Gly Glu Cys Trp Cys
            275                 280                 285

Val Asn Pro Asn Thr Gly Lys Leu Ile Gln Gly Ala Pro Thr Ile Arg
    290                 295                 300

Gly Asp Pro Glu Cys His Leu Phe Tyr Asn Glu Gln Gln Glu Ala Arg
305                 310                 315                 320

Gly Val His Thr Gln Arg Met Gln
                325

<210> SEQ ID NO 18
<211> LENGTH: 289
<212> TYPE: PRT
<213> ORGANISM: Homo sapiens

<400> SEQUENCE: 18

Glu Val Leu Phe Arg Cys Pro Pro Cys Thr Pro Glu Arg Leu Ala Ala
1               5                   10                  15

Cys Gly Pro Pro Pro Val Ala Pro Ala Ala Val Ala Ala Val Ala
            20                  25                  30

Gly Gly Ala Arg Met Pro Cys Ala Glu Leu Val Arg Glu Pro Gly Cys
        35                  40                  45

Gly Cys Cys Ser Val Cys Ala Arg Leu Glu Gly Glu Ala Cys Gly Val
    50                  55                  60

Tyr Thr Pro Arg Cys Gly Gln Gly Leu Arg Cys Tyr Pro His Pro Gly
65                  70                  75                  80

Ser Glu Leu Pro Leu Gln Ala Leu Val Met Gly Glu Gly Thr Cys Glu
                85                  90                  95

Lys Arg Arg Asp Ala Glu Tyr Gly Ala Ser Pro Glu Gln Val Ala Asp
            100                 105                 110

Asn Gly Asp Asp His Ser Glu Gly Gly Leu Val Glu Asn His Val Asp
        115                 120                 125

Ser Thr Met Asn Met Leu Gly Gly Gly Ser Ala Gly Arg Lys Pro
    130                 135                 140

Leu Lys Ser Gly Met Lys Glu Leu Ala Val Phe Arg Glu Lys Val Thr
145                 150                 155                 160

Glu Gln His Arg Gln Met Gly Lys Gly Gly Lys His His Leu Gly Leu
                165                 170                 175

Glu Glu Pro Lys Lys Leu Arg Pro Pro Pro Ala Arg Thr Pro Cys Gln
            180                 185                 190

Gln Glu Leu Asp Gln Val Leu Glu Arg Ile Ser Thr Met Arg Leu Pro
        195                 200                 205
```

```
Asp Glu Arg Gly Pro Leu Glu His Leu Tyr Ser Leu His Ile Pro Asn
    210                 215                 220

Cys Asp Lys His Gly Leu Tyr Asn Leu Lys Gln Cys Lys Met Ser Leu
225                 230                 235                 240

Asn Gly Gln Arg Gly Glu Cys Trp Cys Val Asn Pro Asn Thr Gly Lys
                245                 250                 255

Leu Ile Gln Gly Ala Pro Thr Ile Arg Gly Asp Pro Glu Cys His Leu
            260                 265                 270

Phe Tyr Asn Glu Gln Gln Glu Ala Arg Gly Val His Thr Gln Arg Met
        275                 280                 285

Gln

<210> SEQ ID NO 19
<211> LENGTH: 328
<212> TYPE: PRT
<213> ORGANISM: Homo sapiens
<220> FEATURE:
<221> NAME/KEY: SIGNAL
<222> LOCATION: (1)..(39)

<400> SEQUENCE: 19

Met Leu Pro Arg Val Gly Cys Pro Ala Leu Pro Leu Pro Pro Pro Pro
1               5                   10                  15

Leu Leu Pro Leu Pro Leu Leu Leu Leu Leu Leu Gly Ala Ser Gly Gly
            20                  25                  30

Gly Gly Gly Gly Ala Arg Ala Glu Val Leu Phe Arg Cys Pro Pro Cys
        35                  40                  45

Thr Pro Glu Arg Leu Ala Ala Cys Gly Pro Pro Val Ala Pro Pro
50                  55                  60

Ala Ala Val Ala Ala Val Ala Gly Gly Ala Arg Met Pro Cys Ala Glu
65                  70                  75                  80

Leu Val Arg Glu Pro Gly Cys Gly Cys Cys Ser Val Cys Ala Arg Leu
                85                  90                  95

Glu Gly Glu Ala Cys Gly Val Tyr Thr Pro Arg Cys Gly Gln Gly Leu
            100                 105                 110

Arg Cys Tyr Pro His Pro Gly Ser Glu Leu Pro Leu Gln Ala Leu Val
        115                 120                 125

Met Gly Glu Gly Thr Cys Glu Lys Arg Arg Asp Ala Glu Tyr Gly Ala
130                 135                 140

Ser Pro Glu Gln Val Ala Asp Asn Gly Asp Asp His Ser Glu Gly Gly
145                 150                 155                 160

Leu Val Glu Asn His Val Asp Ser Thr Met Asn Met Leu Gly Gly Gly
                165                 170                 175

Gly Ser Ala Gly Arg Lys Pro Leu Lys Ser Gly Met Lys Glu Leu Ala
            180                 185                 190

Val Phe Arg Glu Lys Val Thr Glu Gln His Arg Gln Met Gly Lys Gly
        195                 200                 205

Gly Lys His His Leu Gly Leu Glu Glu Pro Lys Lys Leu Arg Pro Pro
    210                 215                 220

Pro Ala Arg Thr Pro Cys Gln Gln Glu Leu Asp Gln Val Leu Glu Arg
225                 230                 235                 240

Ile Ser Thr Met Arg Leu Pro Asp Glu Arg Gly Pro Leu Glu His Leu
                245                 250                 255

Tyr Ser Leu His Ile Pro Asn Cys Asp Lys His Gly Leu Tyr Asn Leu
            260                 265                 270
```

```
Lys Gln Cys Lys Met Ser Leu Asn Gly Gln Arg Gly Glu Cys Trp Cys
            275                 280                 285
Val Asn Pro Asn Thr Gly Lys Leu Ile Gln Gly Ala Pro Thr Ile Arg
        290                 295                 300
Gly Asp Pro Glu Cys His Leu Phe Tyr Asn Glu Gln Gln Glu Ala Arg
305                 310                 315                 320
Gly Val His Thr Gln Arg Met Gln
                325

<210> SEQ ID NO 20
<211> LENGTH: 289
<212> TYPE: PRT
<213> ORGANISM: Homo sapiens

<400> SEQUENCE: 20

Glu Val Leu Phe Arg Cys Pro Pro Cys Thr Pro Glu Arg Leu Ala Ala
1               5                   10                  15
Cys Gly Pro Pro Pro Val Ala Pro Ala Ala Val Ala Ala Val Ala
                20                  25                  30
Gly Gly Ala Arg Met Pro Cys Ala Glu Leu Val Arg Glu Pro Gly Cys
            35                  40                  45
Gly Cys Cys Ser Val Cys Ala Arg Leu Glu Gly Glu Ala Cys Gly Val
        50                  55                  60
Tyr Thr Pro Arg Cys Gly Gln Gly Leu Arg Cys Tyr Pro His Pro Gly
65                  70                  75                  80
Ser Glu Leu Pro Leu Gln Ala Leu Val Met Gly Glu Gly Thr Cys Glu
                85                  90                  95
Lys Arg Arg Asp Ala Glu Tyr Gly Ala Ser Pro Glu Gln Val Ala Asp
            100                 105                 110
Asn Gly Asp Asp His Ser Glu Gly Gly Leu Val Glu Asn His Val Asp
        115                 120                 125
Ser Thr Met Asn Met Leu Gly Gly Gly Ser Ala Gly Arg Lys Pro
130                 135                 140
Leu Lys Ser Gly Met Lys Glu Leu Ala Val Phe Arg Glu Lys Val Thr
145                 150                 155                 160
Glu Gln His Arg Gln Met Gly Lys Gly Lys His His Leu Gly Leu
                165                 170                 175
Glu Glu Pro Lys Lys Leu Arg Pro Pro Pro Ala Arg Thr Pro Cys Gln
            180                 185                 190
Gln Glu Leu Asp Gln Val Leu Glu Arg Ile Ser Thr Met Arg Leu Pro
        195                 200                 205
Asp Glu Arg Gly Pro Leu Glu His Leu Tyr Ser Leu His Ile Pro Asn
210                 215                 220
Cys Asp Lys His Gly Leu Tyr Asn Leu Lys Gln Cys Lys Met Ser Leu
225                 230                 235                 240
Asn Gly Gln Arg Gly Glu Cys Trp Cys Val Asn Pro Asn Thr Gly Lys
                245                 250                 255
Leu Ile Gln Gly Ala Pro Thr Ile Arg Gly Asp Pro Glu Cys His Leu
            260                 265                 270
Phe Tyr Asn Glu Gln Gln Glu Ala Arg Gly Val His Thr Gln Arg Met
        275                 280                 285
Gln

<210> SEQ ID NO 21
<211> LENGTH: 328
<212> TYPE: PRT
```

<213> ORGANISM: Homo sapiens
<220> FEATURE:
<221> NAME/KEY: SIGNAL
<222> LOCATION: (1)..(39)

<400> SEQUENCE: 21

```
Met Leu Pro Arg Val Gly Cys Pro Ala Leu Pro Leu Pro Pro Pro
1               5                   10                  15

Leu Leu Pro Leu Leu Pro Leu Leu Leu Leu Leu Gly Ala Ser Gly
            20                  25                  30

Gly Gly Gly Gly Ala Arg Ala Glu Val Leu Phe Arg Cys Pro Cys
            35                  40                  45

Thr Pro Glu Arg Leu Ala Ala Cys Gly Pro Pro Val Ala Pro Pro
50                  55                  60

Ala Ala Val Ala Ala Val Ala Gly Gly Ala Arg Met Pro Cys Ala Glu
65                  70                  75                  80

Leu Val Arg Glu Pro Gly Cys Gly Cys Cys Ser Val Cys Ala Arg Leu
                85                  90                  95

Glu Gly Glu Ala Cys Gly Val Tyr Thr Pro Arg Cys Gly Gln Gly Leu
            100                 105                 110

Arg Cys Tyr Pro His Pro Gly Ser Glu Leu Pro Leu Gln Ala Leu Val
        115                 120                 125

Met Gly Glu Gly Thr Cys Glu Lys Arg Arg Asp Ala Glu Tyr Gly Ala
130                 135                 140

Ser Pro Glu Gln Val Ala Asp Asn Gly Asp Asp His Ser Glu Gly Gly
145                 150                 155                 160

Leu Val Glu Asn His Val Asp Ser Thr Met Asn Met Leu Gly Gly Gly
                165                 170                 175

Gly Ser Ala Gly Arg Lys Pro Leu Lys Ser Gly Met Lys Glu Leu Ala
            180                 185                 190

Val Phe Arg Glu Lys Val Thr Glu Gln His Arg Gln Met Gly Lys Gly
        195                 200                 205

Gly Lys His His Leu Gly Leu Glu Glu Pro Lys Lys Leu Arg Pro Pro
210                 215                 220

Pro Ala Arg Thr Pro Cys Gln Gln Glu Leu Asp Gln Val Leu Glu Arg
225                 230                 235                 240

Ile Ser Thr Met Arg Leu Pro Asp Glu Arg Gly Pro Leu Glu His Leu
                245                 250                 255

Tyr Ser Leu His Ile Pro Asn Cys Asp Lys His Gly Leu Tyr Asn Leu
            260                 265                 270

Lys Gln Cys Lys Met Ser Leu Asn Gly Gln Arg Gly Glu Cys Trp Cys
        275                 280                 285

Val Asn Pro Asn Thr Gly Lys Leu Ile Gln Gly Ala Pro Thr Ile Arg
    290                 295                 300

Gly Asp Pro Glu Cys His Leu Phe Tyr Asn Glu Gln Gln Glu Ala Arg
305                 310                 315                 320

Gly Val His Thr Gln Arg Met Gln
                325
```

<210> SEQ ID NO 22
<211> LENGTH: 289
<212> TYPE: PRT
<213> ORGANISM: Homo sapiens

<400> SEQUENCE: 22

```
Glu Val Leu Phe Arg Cys Pro Cys Thr Pro Glu Arg Leu Ala Ala
1               5                   10                  15
```

```
Cys Gly Pro Pro Pro Val Ala Pro Ala Ala Val Ala Val Ala
                 20                  25                  30

Gly Gly Ala Arg Met Pro Cys Ala Glu Leu Val Arg Glu Pro Gly Cys
         35                  40                  45

Gly Cys Cys Ser Val Cys Ala Arg Leu Glu Gly Glu Ala Cys Gly Val
 50                  55                  60

Tyr Thr Pro Arg Cys Gly Gln Gly Leu Arg Cys Tyr Pro His Pro Gly
 65                  70                  75                  80

Ser Glu Leu Pro Leu Gln Ala Leu Val Met Gly Glu Gly Thr Cys Glu
                 85                  90                  95

Lys Arg Arg Asp Ala Glu Tyr Gly Ala Ser Pro Glu Gln Val Ala Asp
             100                 105                 110

Asn Gly Asp Asp His Ser Glu Gly Gly Leu Val Glu Asn His Val Asp
         115                 120                 125

Ser Thr Met Asn Met Leu Gly Gly Gly Ser Ala Gly Arg Lys Pro
 130                 135                 140

Leu Lys Ser Gly Met Lys Glu Leu Ala Val Phe Arg Glu Lys Val Thr
145                 150                 155                 160

Glu Gln His Arg Gln Met Gly Lys Gly Lys His His Leu Gly Leu
                 165                 170                 175

Glu Glu Pro Lys Lys Leu Arg Pro Pro Ala Arg Thr Pro Cys Gln
                 180                 185                 190

Gln Glu Leu Asp Gln Val Leu Glu Arg Ile Ser Thr Met Arg Leu Pro
         195                 200                 205

Asp Glu Arg Gly Pro Leu Glu His Leu Tyr Ser Leu His Ile Pro Asn
210                 215                 220

Cys Asp Lys His Gly Leu Tyr Asn Leu Lys Gln Cys Lys Met Ser Leu
225                 230                 235                 240

Asn Gly Gln Arg Gly Glu Cys Trp Cys Val Asn Pro Asn Thr Gly Lys
                 245                 250                 255

Leu Ile Gln Gly Ala Pro Thr Ile Arg Gly Asp Pro Glu Cys His Leu
                 260                 265                 270

Phe Tyr Asn Glu Gln Gln Glu Ala Arg Gly Val His Thr Gln Arg Met
                 275                 280                 285

Gln

<210> SEQ ID NO 23
<211> LENGTH: 328
<212> TYPE: PRT
<213> ORGANISM: Homo sapiens
<220> FEATURE:
<221> NAME/KEY: SIGNAL
<222> LOCATION: (1)..(39)

<400> SEQUENCE: 23

Met Leu Pro Arg Val Gly Cys Pro Ala Leu Pro Leu Pro Pro Pro
 1               5                  10                  15

Leu Leu Pro Leu Leu Pro Leu Leu Leu Leu Leu Gly Ala Ser Gly
                 20                  25                  30

Gly Gly Gly Gly Ala Arg Ala Glu Val Leu Phe Arg Cys Pro Pro Cys
         35                  40                  45

Thr Pro Glu Arg Leu Ala Ala Cys Gly Pro Pro Val Ala Pro Pro
 50                  55                  60

Ala Ala Val Ala Ala Val Ala Gly Gly Ala Arg Met Pro Cys Ala Glu
 65                  70                  75                  80
```

```
Leu Val Arg Glu Pro Gly Cys Gly Cys Cys Ser Val Cys Ala Arg Leu
                85                  90                  95

Glu Gly Glu Ala Cys Gly Val Tyr Thr Pro Arg Cys Gly Gln Gly Leu
            100                 105                 110

Arg Cys Tyr Pro His Pro Gly Ser Glu Leu Pro Leu Gln Ala Leu Val
        115                 120                 125

Met Gly Glu Gly Thr Cys Glu Lys Arg Arg Asp Ala Glu Tyr Gly Ala
130                 135                 140

Ser Pro Glu Gln Val Ala Asp Asn Gly Asp Asp His Ser Glu Gly Gly
145                 150                 155                 160

Leu Val Glu Asn His Val Asp Ser Thr Met Asn Met Leu Gly Gly Gly
                165                 170                 175

Gly Ser Ala Gly Arg Lys Pro Leu Lys Ser Gly Met Lys Glu Leu Ala
            180                 185                 190

Val Phe Arg Glu Lys Val Thr Glu Gln His Arg Gln Met Gly Lys Gly
        195                 200                 205

Gly Lys His His Leu Gly Leu Glu Glu Pro Lys Lys Leu Arg Pro Pro
    210                 215                 220

Pro Ala Arg Thr Pro Cys Gln Gln Glu Leu Asp Gln Val Leu Glu Arg
225                 230                 235                 240

Ile Ser Thr Met Arg Leu Pro Asp Glu Arg Gly Pro Leu Glu His Leu
                245                 250                 255

Tyr Ser Leu His Ile Pro Asn Cys Asp Lys His Gly Leu Tyr Asn Leu
            260                 265                 270

Lys Gln Cys Lys Met Ser Leu Asn Gly Gln Arg Gly Glu Cys Trp Cys
        275                 280                 285

Val Asn Pro Asn Thr Gly Lys Leu Ile Gln Gly Ala Pro Thr Ile Arg
290                 295                 300

Gly Asp Pro Glu Cys His Leu Phe Tyr Asn Glu Gln Gln Glu Ala Cys
305                 310                 315                 320

Gly Val His Thr Gln Arg Met Gln
                325

<210> SEQ ID NO 24
<211> LENGTH: 289
<212> TYPE: PRT
<213> ORGANISM: Homo sapiens

<400> SEQUENCE: 24

Glu Val Leu Phe Arg Cys Pro Pro Cys Thr Pro Glu Arg Leu Ala Ala
1               5                   10                  15

Cys Gly Pro Pro Pro Val Ala Pro Pro Ala Ala Val Ala Ala Val Ala
                20                  25                  30

Gly Gly Ala Arg Met Pro Cys Ala Glu Leu Val Arg Glu Pro Gly Cys
            35                  40                  45

Gly Cys Cys Ser Val Cys Ala Arg Leu Glu Gly Glu Ala Cys Gly Val
        50                  55                  60

Tyr Thr Pro Arg Cys Gly Gln Gly Leu Arg Cys Tyr Pro His Pro Gly
65                  70                  75                  80

Ser Glu Leu Pro Leu Gln Ala Leu Val Met Gly Glu Gly Thr Cys Glu
                85                  90                  95

Lys Arg Arg Asp Ala Glu Tyr Gly Ala Ser Pro Glu Gln Val Ala Asp
            100                 105                 110

Asn Gly Asp Asp His Ser Glu Gly Gly Leu Val Glu Asn His Val Asp
        115                 120                 125
```

```
Ser Thr Met Asn Met Leu Gly Gly Gly Ser Ala Gly Arg Lys Pro
    130                 135                 140

Leu Lys Ser Gly Met Lys Glu Leu Ala Val Phe Arg Glu Lys Val Thr
145                 150                 155                 160

Glu Gln His Arg Gln Met Gly Lys Gly Lys His His Leu Gly Leu
                165                 170                 175

Glu Glu Pro Lys Lys Leu Arg Pro Pro Ala Arg Thr Pro Cys Gln
            180                 185                 190

Gln Glu Leu Asp Gln Val Leu Glu Arg Ile Ser Thr Met Arg Leu Pro
                195                 200                 205

Asp Glu Arg Gly Pro Leu Glu His Leu Tyr Ser Leu His Ile Pro Asn
    210                 215                 220

Cys Asp Lys His Gly Leu Tyr Asn Leu Lys Gln Cys Lys Met Ser Leu
225                 230                 235                 240

Asn Gly Gln Arg Gly Glu Cys Trp Cys Val Asn Pro Asn Thr Gly Lys
                245                 250                 255

Leu Ile Gln Gly Ala Pro Thr Ile Arg Gly Asp Pro Glu Cys His Leu
                260                 265                 270

Phe Tyr Asn Glu Gln Gln Glu Ala Cys Gly Val His Thr Gln Arg Met
            275                 280                 285

Gln

<210> SEQ ID NO 25
<211> LENGTH: 329
<212> TYPE: PRT
<213> ORGANISM: Homo sapiens
<220> FEATURE:
<221> NAME/KEY: SIGNAL
<222> LOCATION: (1)..(39)

<400> SEQUENCE: 25

Met Leu Pro Arg Val Gly Cys Pro Ala Leu Pro Leu Pro Pro Pro Pro
1               5                   10                  15

Leu Leu Pro Leu Leu Pro Leu Leu Leu Leu Leu Gly Ala Ser Gly
            20                  25                  30

Gly Gly Gly Gly Ala Arg Ala Glu Val Leu Phe Arg Cys Pro Pro Cys
                35                  40                  45

Thr Pro Glu Arg Leu Ala Ala Cys Gly Pro Pro Val Ala Pro Pro
50                  55                  60

Ala Ala Val Ala Ala Val Ala Gly Gly Ala Cys Met Pro Cys Ala Glu
65                  70                  75                  80

Leu Val Arg Glu Pro Gly Cys Gly Cys Cys Ser Val Cys Ala Arg Leu
                85                  90                  95

Glu Gly Glu Ala Cys Gly Val Tyr Thr Pro Arg Cys Gln Gly Leu
            100                 105                 110

Arg Cys Tyr Pro His Pro Gly Ser Glu Leu Pro Leu Gln Ala Leu Val
                115                 120                 125

Met Gly Glu Gly Thr Cys Glu Lys Arg Arg Asp Ala Glu Tyr Gly Ala
            130                 135                 140

Ser Pro Glu Gln Val Ala Asp Asn Gly Asp Asp His Ser Glu Gly Gly
145                 150                 155                 160

Leu Val Glu Asn His Val Asp Ser Thr Met Asn Met Leu Gly Gly Gly
                165                 170                 175

Gly Ser Ala Gly Arg Lys Pro Leu Lys Ser Gly Met Lys Glu Leu Ala
            180                 185                 190

Val Phe Arg Glu Lys Val Thr Glu Gln His Arg Gln Met Gly Lys Gly
```

```
              195                 200                 205
Gly Lys His His Leu Gly Leu Glu Glu Pro Lys Leu Arg Pro Pro
             210                 215                 220

Pro Ala Arg Thr Pro Cys Gln Gln Glu Leu Asp Gln Val Leu Glu Arg
225                 230                 235                 240

Ile Ser Thr Met Arg Leu Pro Asp Glu Arg Gly Pro Leu Glu His Leu
                        245                 250                 255

Tyr Ser Leu His Ile Pro Asn Cys Asp Lys His Gly Leu Tyr Asn Leu
                260                 265                 270

Lys Gln Cys Lys Met Ser Leu Asn Gly Gln Arg Gly Glu Cys Trp Cys
            275                 280                 285

Val Asn Pro Asn Thr Gly Lys Leu Ile Gln Gly Ala Pro Thr Ile Arg
290                 295                 300

Gly Asp Pro Glu Cys His Leu Phe Tyr Asn Glu Gln Gln Glu Ala Arg
305                 310                 315                 320

Gly Val His Thr Gln Arg Met Gln Leu
                325

<210> SEQ ID NO 26
<211> LENGTH: 290
<212> TYPE: PRT
<213> ORGANISM: Homo sapiens

<400> SEQUENCE: 26

Glu Val Leu Phe Arg Cys Pro Pro Cys Thr Pro Glu Arg Leu Ala Ala
1               5                   10                  15

Cys Gly Pro Pro Pro Val Ala Pro Pro Ala Ala Val Ala Ala Val Ala
                20                  25                  30

Gly Gly Ala Cys Met Pro Cys Ala Glu Leu Val Arg Glu Pro Gly Cys
            35                  40                  45

Gly Cys Cys Ser Val Cys Ala Arg Leu Glu Gly Glu Ala Cys Gly Val
        50                  55                  60

Tyr Thr Pro Arg Cys Gly Gln Gly Leu Arg Cys Tyr Pro His Pro Gly
65                  70                  75                  80

Ser Glu Leu Pro Leu Gln Ala Leu Val Met Gly Glu Gly Thr Cys Glu
                85                  90                  95

Lys Arg Arg Asp Ala Glu Tyr Gly Ala Ser Pro Glu Gln Val Ala Asp
            100                 105                 110

Asn Gly Asp Asp His Ser Glu Gly Gly Leu Val Glu Asn His Val Asp
        115                 120                 125

Ser Thr Met Asn Met Leu Gly Gly Gly Gly Ser Ala Gly Arg Lys Pro
    130                 135                 140

Leu Lys Ser Gly Met Lys Glu Leu Ala Val Phe Arg Glu Lys Val Thr
145                 150                 155                 160

Glu Gln His Arg Gln Met Gly Lys Gly Gly Lys His His Leu Gly Leu
                165                 170                 175

Glu Glu Pro Lys Lys Leu Arg Pro Pro Ala Arg Thr Pro Cys Gln
            180                 185                 190

Gln Glu Leu Asp Gln Val Leu Glu Arg Ile Ser Thr Met Arg Leu Pro
    195                 200                 205

Asp Glu Arg Gly Pro Leu Glu His Leu Tyr Ser Leu His Ile Pro Asn
210                 215                 220

Cys Asp Lys His Gly Leu Tyr Asn Leu Lys Gln Cys Lys Met Ser Leu
225                 230                 235                 240

Asn Gly Gln Arg Gly Glu Cys Trp Cys Val Asn Pro Asn Thr Gly Lys
```

```
                    245                 250                 255
Leu Ile Gln Gly Ala Pro Thr Ile Arg Gly Asp Pro Glu Cys His Leu
            260                 265                 270

Phe Tyr Asn Glu Gln Gln Glu Ala Arg Gly Val His Thr Gln Arg Met
        275                 280                 285

Gln Leu
    290

<210> SEQ ID NO 27
<211> LENGTH: 328
<212> TYPE: PRT
<213> ORGANISM: Homo sapiens
<220> FEATURE:
<221> NAME/KEY: SIGNAL
<222> LOCATION: (1)..(39)

<400> SEQUENCE: 27

Met Leu Pro Arg Val Gly Cys Pro Ala Leu Pro Leu Pro Pro Pro Pro
1               5                   10                  15

Leu Leu Pro Leu Leu Pro Leu Leu Leu Leu Leu Gly Ala Ser Gly Gly
            20                  25                  30

Gly Gly Gly Gly Ala Arg Ala Glu Val Leu Phe Arg Cys Pro Pro Cys
        35                  40                  45

Thr Pro Glu Arg Leu Ala Ala Cys Gly Pro Pro Arg Val Ala Pro Pro
    50                  55                  60

Ala Ala Val Ala Ala Val Ala Gly Gly Ala Arg Met Pro Cys Ala Glu
65                  70                  75                  80

Leu Val Arg Glu Pro Gly Cys Gly Cys Cys Ser Val Cys Ala Arg Leu
                85                  90                  95

Glu Gly Glu Ala Cys Gly Val Tyr Thr Pro Arg Cys Gly Gln Gly Leu
            100                 105                 110

Arg Cys Tyr Pro His Pro Gly Ser Glu Leu Pro Leu Gln Ala Leu Val
        115                 120                 125

Met Gly Glu Gly Thr Cys Glu Lys Arg Arg Asp Ala Glu Tyr Gly Ala
    130                 135                 140

Ser Pro Glu Gln Val Ala Asp Asn Gly Asp Asp His Ser Glu Gly Gly
145                 150                 155                 160

Leu Val Glu Asn His Val Asp Ser Thr Met Asn Met Leu Gly Gly Gly
                165                 170                 175

Gly Ser Ala Gly Arg Lys Pro Leu Lys Ser Gly Met Lys Glu Leu Ala
            180                 185                 190

Val Phe Arg Glu Lys Val Thr Glu Gln His Arg Gln Met Gly Lys Gly
        195                 200                 205

Gly Lys His His Leu Gly Leu Glu Glu Pro Lys Lys Leu Arg Pro Pro
    210                 215                 220

Pro Ala Arg Thr Pro Cys Gln Gln Glu Leu Asp Gln Val Leu Glu Arg
225                 230                 235                 240

Ile Ser Thr Met Arg Leu Pro Asp Glu Arg Gly Pro Leu Glu His Leu
                245                 250                 255

Tyr Ser Leu His Ile Pro Asn Cys Asp Lys His Gly Leu Tyr Asn Leu
            260                 265                 270

Lys Gln Cys Lys Met Ser Leu Asn Gly Gln Arg Gly Glu Cys Trp Cys
        275                 280                 285

Val Asn Pro Asn Thr Gly Lys Leu Ile Gln Gly Ala Pro Thr Ile Arg
    290                 295                 300

Gly Asp Pro Glu Cys His Leu Phe Tyr Asn Glu Gln Gln Glu Ala Arg
```

```
                305                 310                 315                 320

Gly Val Asp Thr Gln Arg Met Gln
                325

<210> SEQ ID NO 28
<211> LENGTH: 289
<212> TYPE: PRT
<213> ORGANISM: Homo sapiens

<400> SEQUENCE: 28

Glu Val Leu Phe Arg Cys Pro Pro Cys Thr Pro Glu Arg Leu Ala Ala
1               5                   10                  15

Cys Gly Pro Pro Arg Val Ala Pro Ala Ala Val Ala Val Ala
                20                  25                  30

Gly Gly Ala Arg Met Pro Cys Ala Glu Leu Val Arg Glu Pro Gly Cys
                35                  40                  45

Gly Cys Cys Ser Val Cys Ala Arg Leu Glu Gly Glu Ala Cys Gly Val
            50                  55                  60

Tyr Thr Pro Arg Cys Gly Gln Gly Leu Arg Cys Tyr Pro His Pro Gly
65              70                  75                  80

Ser Glu Leu Pro Leu Gln Ala Leu Val Met Gly Glu Gly Thr Cys Glu
                85                  90                  95

Lys Arg Arg Asp Ala Glu Tyr Gly Ala Ser Pro Glu Gln Val Ala Asp
                100                 105                 110

Asn Gly Asp Asp His Ser Glu Gly Gly Leu Val Glu Asn His Val Asp
            115                 120                 125

Ser Thr Met Asn Met Leu Gly Gly Gly Gly Ser Ala Gly Arg Lys Pro
130                 135                 140

Leu Lys Ser Gly Met Lys Glu Leu Ala Val Phe Arg Glu Lys Val Thr
145                 150                 155                 160

Glu Gln His Arg Gln Met Gly Lys Gly Lys His His Leu Gly Leu
                165                 170                 175

Glu Glu Pro Lys Lys Leu Arg Pro Pro Pro Ala Arg Thr Pro Cys Gln
                180                 185                 190

Gln Glu Leu Asp Gln Val Leu Glu Arg Ile Ser Thr Met Arg Leu Pro
            195                 200                 205

Asp Glu Arg Gly Pro Leu Glu His Leu Tyr Ser Leu His Ile Pro Asn
210                 215                 220

Cys Asp Lys His Gly Leu Tyr Asn Leu Lys Gln Cys Lys Met Ser Leu
225                 230                 235                 240

Asn Gly Gln Arg Gly Glu Cys Trp Cys Val Asn Pro Asn Thr Gly Lys
                245                 250                 255

Leu Ile Gln Gly Ala Pro Thr Ile Arg Gly Asp Pro Glu Cys His Leu
                260                 265                 270

Phe Tyr Asn Glu Gln Gln Glu Ala Arg Gly Val Asp Thr Gln Arg Met
            275                 280                 285

Gln

<210> SEQ ID NO 29
<211> LENGTH: 328
<212> TYPE: PRT
<213> ORGANISM: Homo sapiens
<220> FEATURE:
<221> NAME/KEY: MISC_FEATURE
<223> OTHER INFORMATION: X can be any naturally occurring amino acid
<220> FEATURE:
<221> NAME/KEY: SIGNAL
<222> LOCATION: (1)..(39)
```

```
<220> FEATURE:
<221> NAME/KEY: misc_feature
<222> LOCATION: (137)..(137)
<223> OTHER INFORMATION: Xaa can be any naturally occurring amino acid
<220> FEATURE:
<221> NAME/KEY: misc_feature
<222> LOCATION: (139)..(139)
<223> OTHER INFORMATION: Xaa can be any naturally occurring amino acid
<220> FEATURE:
<221> NAME/KEY: misc_feature
<222> LOCATION: (323)..(323)
<223> OTHER INFORMATION: Xaa can be any naturally occurring amino acid

<400> SEQUENCE: 29

Met Leu Pro Arg Val Gly Cys Pro Ala Leu Pro Leu Pro Pro Pro Pro
1               5                   10                  15

Leu Leu Pro Leu Leu Pro Leu Leu Leu Leu Leu Leu Gly Ala Ser Gly
            20                  25                  30

Gly Gly Gly Gly Ala Arg Ala Glu Val Leu Phe Arg Cys Pro Pro Cys
        35                  40                  45

Thr Pro Glu Arg Leu Ala Ala Cys Gly Pro Pro Val Ala Pro Pro
    50                  55                  60

Ala Ala Val Ala Val Ala Gly Gly Ala Arg Met Pro Cys Ala Glu
65                  70                  75                  80

Leu Val Arg Glu Pro Gly Cys Gly Cys Ser Val Cys Ala Arg Leu
                85                  90                  95

Glu Gly Glu Ala Cys Gly Val Tyr Thr Pro Arg Cys Gly Gln Gly Leu
            100                 105                 110

Arg Cys Tyr Pro His Pro Gly Ser Glu Leu Pro Leu Gln Ala Leu Val
        115                 120                 125

Met Gly Glu Gly Thr Cys Glu Lys Xaa Arg Xaa Ala Glu Tyr Gly Ala
130                 135                 140

Ser Pro Glu Gln Val Ala Asp Asn Gly Asp Asp His Ser Glu Gly Gly
145                 150                 155                 160

Leu Val Glu Asn His Val Asp Ser Thr Met Asn Met Leu Gly Gly Gly
                165                 170                 175

Gly Ser Ala Gly Arg Lys Pro Leu Lys Ser Gly Met Lys Glu Leu Ala
            180                 185                 190

Val Phe Arg Glu Lys Val Thr Glu Gln His Arg Gln Met Gly Lys Gly
        195                 200                 205

Gly Lys His His Leu Gly Leu Glu Glu Pro Lys Lys Leu Arg Pro Pro
    210                 215                 220

Pro Ala Arg Thr Pro Cys Gln Gln Glu Leu Asp Gln Val Leu Glu Arg
225                 230                 235                 240

Ile Ser Thr Met Arg Leu Pro Asp Glu Arg Gly Pro Leu Glu His Leu
                245                 250                 255

Tyr Ser Leu His Ile Pro Asn Cys Asp Lys His Gly Leu Tyr Asn Leu
            260                 265                 270

Lys Gln Cys Lys Met Ser Leu Asn Gly Gln Arg Gly Glu Cys Trp Cys
        275                 280                 285

Val Asn Pro Asn Thr Gly Lys Leu Ile Gln Gly Ala Pro Thr Ile Arg
    290                 295                 300

Gly Asp Pro Glu Cys His Leu Phe Tyr Asn Glu Gln Glu Ala Arg
305                 310                 315                 320

Gly Val Xaa Thr Gln Arg Met Gln
                325

<210> SEQ ID NO 30
```

```
<211> LENGTH: 289
<212> TYPE: PRT
<213> ORGANISM: Homo sapiens
<220> FEATURE:
<221> NAME/KEY: MISC_FEATURE
<223> OTHER INFORMATION: X can be any naturally occurring amino acid
<220> FEATURE:
<221> NAME/KEY: misc_feature
<222> LOCATION: (98)..(98)
<223> OTHER INFORMATION: Xaa can be any naturally occurring amino acid
<220> FEATURE:
<221> NAME/KEY: misc_feature
<222> LOCATION: (100)..(100)
<223> OTHER INFORMATION: Xaa can be any naturally occurring amino acid
<220> FEATURE:
<221> NAME/KEY: misc_feature
<222> LOCATION: (284)..(284)
<223> OTHER INFORMATION: Xaa can be any naturally occurring amino acid

<400> SEQUENCE: 30

Glu Val Leu Phe Arg Cys Pro Pro Cys Thr Pro Glu Arg Leu Ala Ala
1               5                   10                  15

Cys Gly Pro Pro Pro Val Ala Pro Pro Ala Ala Val Ala Ala Val Ala
            20                  25                  30

Gly Gly Ala Arg Met Pro Cys Ala Glu Leu Val Arg Glu Pro Gly Cys
        35                  40                  45

Gly Cys Cys Ser Val Cys Ala Arg Leu Glu Gly Glu Ala Cys Gly Val
    50                  55                  60

Tyr Thr Pro Arg Cys Gly Gln Gly Leu Arg Cys Tyr Pro His Pro Gly
65                  70                  75                  80

Ser Glu Leu Pro Leu Gln Ala Leu Val Met Gly Glu Gly Thr Cys Glu
                85                  90                  95

Lys Xaa Arg Xaa Ala Glu Tyr Gly Ala Ser Pro Glu Gln Val Ala Asp
            100                 105                 110

Asn Gly Asp Asp His Ser Glu Gly Gly Leu Val Glu Asn His Val Asp
        115                 120                 125

Ser Thr Met Asn Met Leu Gly Gly Gly Ser Ala Gly Arg Lys Pro
    130                 135                 140

Leu Lys Ser Gly Met Lys Glu Leu Ala Val Phe Arg Glu Lys Val Thr
145                 150                 155                 160

Glu Gln His Arg Gln Met Gly Lys Gly Gly Lys His His Leu Gly Leu
                165                 170                 175

Glu Glu Pro Lys Lys Leu Arg Pro Pro Ala Arg Thr Pro Cys Gln
            180                 185                 190

Gln Glu Leu Asp Gln Val Leu Glu Arg Ile Ser Thr Met Arg Leu Pro
        195                 200                 205

Asp Glu Arg Gly Pro Leu Glu His Leu Tyr Ser Leu His Ile Pro Asn
210                 215                 220

Cys Asp Lys His Gly Leu Tyr Asn Leu Lys Gln Cys Lys Met Ser Leu
225                 230                 235                 240

Asn Gly Gln Arg Gly Glu Cys Trp Cys Val Asn Pro Asn Thr Gly Lys
                245                 250                 255

Leu Ile Gln Gly Ala Pro Thr Ile Arg Gly Asp Pro Glu Cys His Leu
            260                 265                 270

Phe Tyr Asn Glu Gln Gln Glu Ala Arg Gly Val Xaa Thr Gln Arg Met
        275                 280                 285

Gln
```